(12) United States Patent
Zhang et al.

(10) Patent No.: US 9,085,602 B1
(45) Date of Patent: Jul. 21, 2015

(54) FACIAL AMPHIPHILES AND METHODS OF USE

(75) Inventors: Qinghai Zhang, San Diego, CA (US); Wen-Xu Hong, San Diego, CA (US); M. G. Finn, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 728 days.

(21) Appl. No.: 12/536,423

(22) Filed: Aug. 5, 2009

Related U.S. Application Data

(60) Provisional application No. 61/087,573, filed on Aug. 8, 2008, provisional application No. 61/222,803, filed on Jul. 2, 2009.

(51) Int. Cl.
*C07J 17/00* (2006.01)
*C07J 51/00* (2006.01)
*C07J 9/00* (2006.01)

(52) U.S. Cl.
CPC .............. *C07J 17/00* (2013.01); *C07J 17/005* (2013.01); *C07J 51/00* (2013.01)

(58) Field of Classification Search
CPC ........... C07J 17/00; C07J 17/005; C07J 51/00
USPC ................. 540/2, 114; 552/506, 542, 549
See application file for complete search history.

(56) References Cited

U.S. PATENT DOCUMENTS

| | | | |
|---|---|---|---|
| 4,612,302 | A | 9/1986 | Szabo et al. |
| 4,684,620 | A | 8/1987 | Hruby et al. |
| 4,853,371 | A | 8/1989 | Coy et al. |

OTHER PUBLICATIONS

Bennet et al., "Self-association of Phenolics and of Bile Acid Derivatives". Nature, vol. 214, pp. 776-780, 1967.*
Plattner et al., "Steroids and sex hormones. CXVI. New glucosides in the steroid series." Helvetica Chimica Acta, vol. 28, pp. 1049-1053, 1945 (English Abstract attached).*
Hjelmeland, Leonard M., "A nondenaturing zwitterionic detergent for membrane biochemistry: Design and synthesis", *Proc. Natl. Acad. Sci. USA*, vol. 77, No. 11 (Nov. 1980), 6368-6370.
Hjelmeland, L. M., "The Design and Synthesis of Detergents for Membrane Biochemistry", *Methods in Enzymology*, vol. 124; Copyright 1986 by Academic Press, Inc., (1986), 135-164.
Zhang, Qinghai, et al., "Designing Facial Amphiphiles for the Stabilization of Integral Membrane Proteins", *Angew. Chem. Int. Ed. 2007*, 46 (Published Online Aug. 9, 2007), 7023-7025.

* cited by examiner

*Primary Examiner* — Barbara P Badio
(74) *Attorney, Agent, or Firm* — Schwegman Lundberg & Woessner, P.A.

(57) ABSTRACT

The invention provides amphiphilic compounds with hydrophobic and hydrophilic faces. The compounds can be readily prepared from steroids such as cholic acid or deoxycholic acid, which provide hydrophobic skeletons with structures similar to that of the lipid cholesterol. The compounds of the invention can be used to aid the solubilization, isolation, purification, stabilization, crystallization, and/or structural determination of membrane proteins, and to prepare micelles for delivery of a bioactive agent, such as a drug or a gene, to a subject.

7 Claims, 5 Drawing Sheets

FACIAL AMPHIPHILES AND METHODS OF USE

RELATED APPLICATIONS

This application claims priority under 35 U.S.C. §119(e) to U.S. Provisional Patent Application Nos. 61/087,573, filed Aug. 8, 2008 and 61/222,803, filed Jul. 2, 2009, both of which are incorporated herein by reference in their entirety.

GOVERNMENT SUPPORT

This invention was made with government support under Grant No. GM073197 awarded by the National Institutes of Health. The United States Government has certain rights in the invention.

BACKGROUND OF THE INVENTION

Integral membrane proteins (IMPs) are essential for cell function and comprise more than 50% of human drug targets. However, they are difficult to solubilize and purify from cell membranes while maintaining their natively folded structures and functions. IMPs are notoriously difficult to handle because of their instability and their tendency to lose function outside the lipid bilayer. Detergents, structurally similar to cellular lipids with an alkyl chain at one end and a polar head group at the other, are indispensable for the solubilization and purification of IMPs. However, IMPs tend to denature or aggregate in the presence of common detergents, which presents a significant challenge for manipulating the proteins during biochemical assays and structural analysis. The development of new types of amphiphilic molecules that can stabilize IMPs would therefore be of great value for both functional and structural investigation.

Also, only a small number of high resolution crystallographic structures of IMPs are available to date because of the difficulties of their isolation, purification, and crystallization. Numerous detergents are screened when investigators seek to isolate and purify new membrane proteins. The screening remains an expensive and labor-intensive task with a low rate of success. Thus, new detergents for IMPs are needed in the art.

Cholic acid and deoxycholic acid are naturally occurring bile acids that display a degree of facial amphiphilicity due to the orientation of multiple hydroxyl groups on one face of the rigid hydrophobic steroid skeleton. They and their derivatives have broad application in various fields, including in membrane chemistry and biochemistry, as detergents, as well as in molecular recognition studies. Previous attempts to use this motif in membrane biochemistry featured the replacement of carboxylic acid group at one end of cholic acid with other polar head groups to provide, for example, CHAPS (3-[(3-cholamidopropyl)-dimethylammonio]-1-propanesulfonate) and CHAPSO (3-[(3-cholamidopropyl)-dimethylammonio]-2-hydroxy-1-propanesulfonate), which are now widely commercially available. Yet these compounds do not sufficiently alleviate the problems associated with solubilizing and purifying membrane proteins, and other needs in the fields of membrane chemistry and biochemistry. Accordingly, new detergent molecules are clearly needed to aid membrane research endeavors.

SUMMARY

The invention provides a new class of steroid-based facial amphiphiles that can be used to aid the manipulation of membrane proteins. For example, the amphiphiles can be used for the solubilization, isolation, purification, stabilization, crystallization, and/or structural determination of membrane proteins. The compounds of the invention also have advantageous properties useful for other applications, such as for use as detergents, cleaning agents, and delivery systems. For example, the facial amphiphiles can be used to prepare micelles for the delivery of bioactive agents, such as drugs, genes, or other bioactive agents.

Accordingly, the invention provides compounds of Formula I:

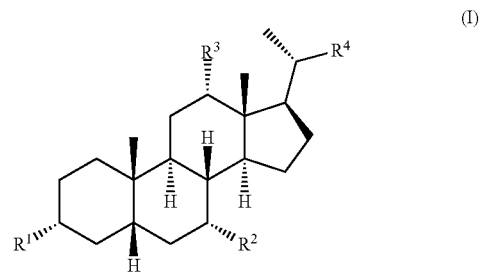

wherein $R^1$, $R^2$ and $R^3$ are each independently H, OH, or —X—R, provided that at least one of $R^1$, $R^2$ and $R^3$ is —X—R;

X is a direct bond or a linker, wherein the linker is a divalent radical of the formula —W-A-W— wherein each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-3, or a direct bond; wherein each R' is independently H, (C$_1$-C$_6$)alkyl, or a nitrogen protecting group; and A is (C$_1$-C$_{20}$)alkyl, (C$_2$-C$_{16}$)alkenyl, (C$_2$-C$_{16}$)alkynyl, (C$_3$-C$_8$)cycloalkyl, (C$_6$-C$_{10}$)aryl, —(OCH$_2$—CH$_2$)$_n$— where n is 1 to about 20, —C(O)NH(CH$_2$)$_n$ wherein n is 1 to about 6, —OP(O)(OH)O—, —OP(O)(OH)O(CH$_2$)$_n$ wherein n is 1 to about 6, —OP(O)(OH)OCH$_2$CH(OH)CH$_2$—, —N$^+$(Me)$_2$(CH$_2$), wherein n is 1 to about 6; or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with a (C$_3$-C$_8$)cycloalkyl, heterocycle, or (C$_6$-C$_{10}$)aryl group;

R is a polar group, wherein the polar group is a monosaccharide, a disaccharide, an amino acid, a peptide, —CO$_2$H, —SH, —S(O)OH, —S(O)$_2$OH, —OS(O)$_2$OH, —P(OH)$_2$, —P(O)OH$_2$, —OP(O)(OH)OH, —N$^+$H$_3$, —N$^+$(Me)$_3$, —N$^+$(Me)$_2$-O$^-$, —(OCH$_2$CH$_2$)$_n$—OH where n is 1 to about 20, or —(OCH$_2$CH$_2$)$_n$—O(alkyl) where n is 1 to about 20; and $R^4$ is (C$_1$-C$_{20}$)alkyl, wherein the alkyl is straight, branched, cyclic, or a combination thereof.

As is readily understood by one of skill in the art, in some embodiments Formula I can be a cation. In other embodiments, Formula I can be an anion. Formula I can also be a salt, for example, when a group attached to Formula I includes a charged atom.

In some embodiments, all R groups can be the same. In other embodiments, the R groups will differ from each other. In some embodiments, X can be a direct bond and R can be directly attached to Formula I, for example, through an oxygen of the polar group.

In one embodiment each R is glucose or maltose. In another embodiment, one R can be glucose and another R can maltose. Additional variations include other polar groups, such as monosaccharides, disaccharides, PEG, and the like, to provide numerous other compounds of the invention. In each instance, the R group can be bonded directly to Formula I, or it can be linked to Formula I through a linker. The linker can be an oxygen-alkyl linker such as an ethylene glycol linker (e.g., —O—$(CH_2)_n$— wherein n is 1 to about 20, or —O—$CH_2$—$CH_2$—), wherein the terminal carbon of the linker can bond directly to a polar group, such as an anomeric oxygen of the saccharide, or another available hydroxyl moiety. Other linkers known in the art, such as those described herein, may also be employed.

In some embodiment, $R^1$ can be H or OH, $R^2$ can be H or OH, and $R^3$ can be H or OH. In certain embodiments, $R^4$ is propyl.

In some embodiments, at least one of $R^1$, $R^2$ and $R^3$ is —X—R wherein X is a direct bond and R is a monosaccharide, a disaccharide, or —$(OCH_2CH_2)_n$—OH where n is 1 to about 10, or —X—R is —$OCH_2CH_2$O-monosaccharide, —$OCH_2CH_2$O-disaccharide, —$OCH_2CH_2$O—P(O)(OH)O—$CH_2CH_2$OH, —$OCH_2CH_2$O—P(O)(OH)O—$CH_2CH_2$—$N^+(Me)_3$, or —$OCH_2CH_2$O—P(O)(OH)O—$CH_2CH_2$—$N^+(Me)_2O^-$. In other embodiments, two or three of $R^1$, $R^2$ and $R^3$ include a polar group. Accordingly, in some embodiments, X is —O—$CH_2$—$CH_2$—; and in other embodiments, the group X can be a direct bond. The compound can be any compound of Formula I described herein.

The invention further provides compositions that include a compound of the invention and a membrane protein, such as an integral membrane protein. The compositions can include a plurality of compounds of the invention in the form of micelles, wherein the micelles optionally encapsulate a polypeptide, a protein, and/or one or more other types of molecules.

Accordingly, the invention provides a method of solubilizing a membrane protein comprising contacting the membrane protein with a plurality of compounds described herein, in an aqueous solution, thereby forming a solubilized aggregation of the compounds and the membrane protein. The invention also provides a method of stabilizing a membrane protein comprising contacting the membrane protein with a plurality of compounds described herein, in an aqueous solution, thereby forming an aggregation of the compounds and the membrane protein. The invention further provides a method of extracting a protein from a lipid bilayer comprising contacting the lipid bilayer with a plurality of compounds described herein in an aqueous solution to form a mixture, optionally in the presence of a buffer, thereby forming an aggregation of the compounds and the membrane protein extracted from the lipid bilayer, and separating the aggregation from the mixture.

Therefore, the invention provides novel compounds, intermediates for the synthesis of the compounds, as well as methods of preparing the compounds described herein. The invention also provides compounds that are useful as intermediates for the synthesis of other valuable compounds. The invention further provides methods of using the compounds, for example, to aid the solubilization, isolation, purification, stabilization, crystallization, and/or structural determination of membrane proteins. The compounds of the invention can be used alone, or in combination with lipids or known detergents.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 2 (d) illustrates ATP hydrolysis by NBD (solid triangle) and MsbA (solid square, in compound 1), indicated by the decrease in absorbance of NADH at 340 nm. UDM is undecyl-β-D-maltoside.

DETAILED DESCRIPTION

Figure 1:
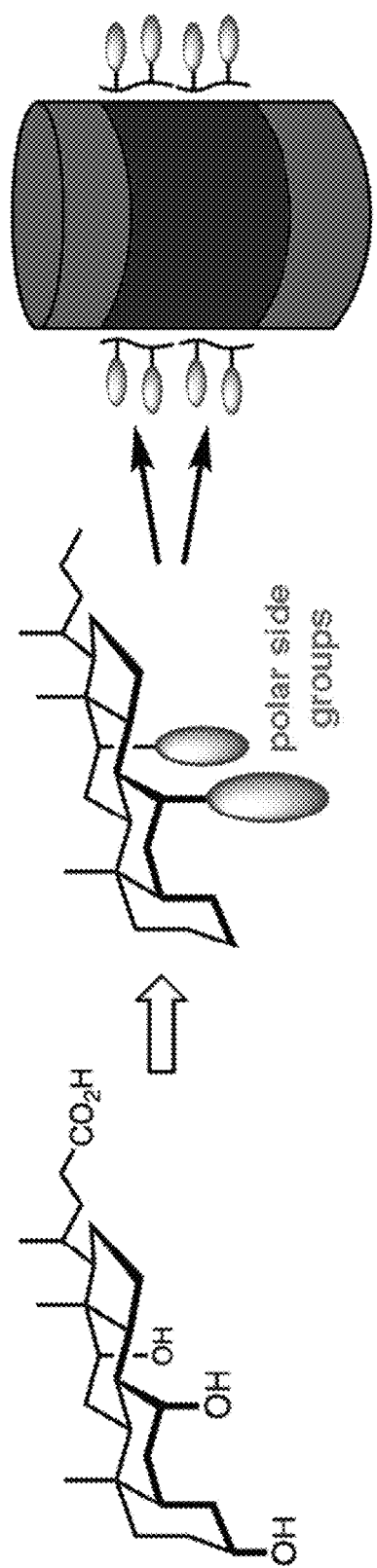
FIG. 1 illustrates facial amphiphiles stabilizing a membrane protein, according to an embodiment of the invention.

Cholate has a long history in membrane biochemistry, but its use is restricted to environments with pH>7.5 due to the necessary ionization of the pendant carboxylic acid for suitable detergent activity. Replacement of the carboxylate group of cholate with other polar head groups to give, for example, the zwitterionic CHAPS (3-[(3-cholamidopropyl)-dimethylammonio]-1-propanesulfonate) and CHAPSO (3-[(3-cholamidopropyl)-dimethylammonio]-2-hydroxy-1-propanesulfonate) extends the utility of the cholate skeleton. These structures are mostly used in protein reconstitution due to their high critical micelle concentrations (CMCs). In spite of more than a decade of effort, such steroid-based amphiphiles have yet to replace traditional detergents in the crystallization of an IMP for X-ray analysis.

The three hydroxyl groups in cholate and its derivatives provide only a small degree of facial amphiphilicity, leaving the very polar carboxylate or the zwitterionic end unit to provide the main driving force for aqueous solubility in the same manner as in classical detergents. A different design of amphiphiles derived from cholic acid is described herein. It has now been demonstrated that molecules based on this design are able to maintain the stability of IMPs. Such stabilization has not been achieved thus far with known surfactants or other cholate derivatives.

Scheme A.

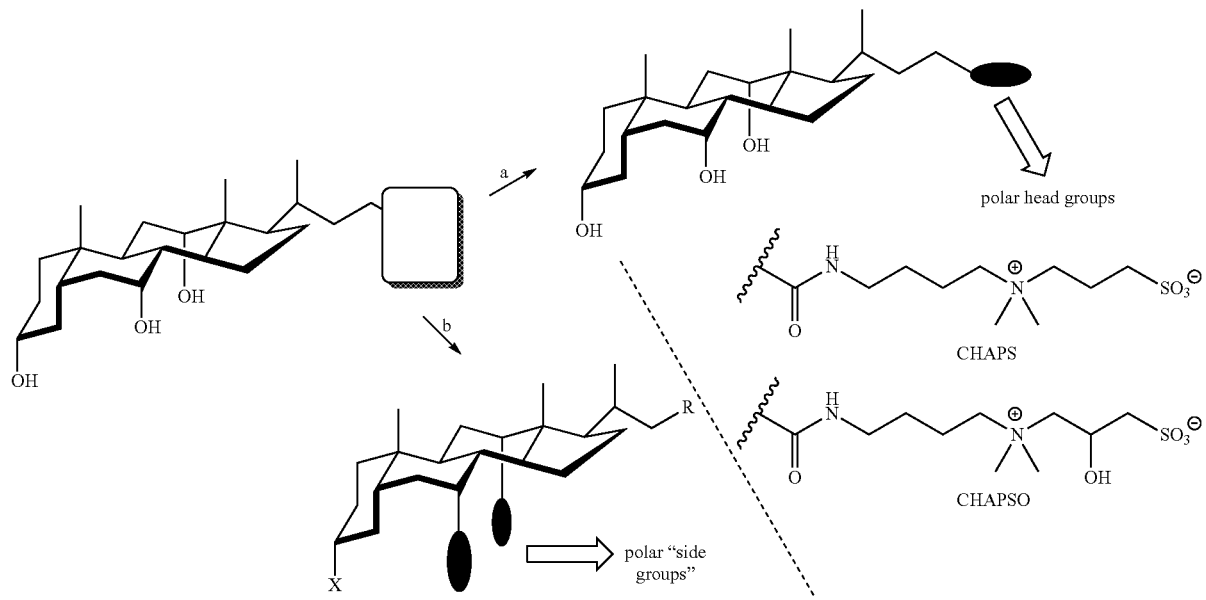

where X is H, OH or other polar groups; and R is a straight, branched, or cyclic alkyl group.

Departing from the canonical "polar head, nonpolar tail" design of detergents, the invention provides molecules that exhibit "facial" amphiphilicity. One scaffold for the compounds of the invention is cholate, which projects three hydroxyl groups from the same face of its steroid backbone (Scheme A). Scheme A illustrates amphiphile designs derived from cholic acid: (a) traditional "polar head, nonpolar tail" structures; and (b) the facial motif approach of the present invention (e.g., to provide the Classes A-C amphiphiles, described below). Class D and E amphiphiles are derived from deoxycholic acid (containing 3α and 12α —OH groups) based on the same design principle.

Amphiphiles of the invention can be prepared by converting hydroxyl groups of one face of a steroid precursor to polar groups. The polar groups can be attached to the steroid backbone either directly through one or more of the hydroxyl oxygens, through linking groups, such as poly(ethylene glycol) moieties, or a combination thereof. Other amphiphiles can be prepared by removing any one of the hydroxyl groups (3α, 7α, or 12α), and converting one or both of the remaining hydroxyl groups to polar groups, linked either directly, or through one or more linking groups.

The invention deviates from the structure of most other steroid-based facial amphiphiles in at least two aspects. See Scheme A, path b. To provide one class of amphiphiles of the invention, first the terminal carboxylate of cholate was removed, leaving a short alkyl chain that mimics the structure of cholesterol. Second, uncharged polar groups were attached to the parallel hydroxyl groups in the center of the cholic acid skeleton. The amphiphiles can pack face-to-face when self-assembling, thus providing a novel and highly effective detergent that can be used for the isolation, purification, characterization, and identification of IMPs.

Definitions

As used herein, certain terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14th Edition, by R. J. Lewis, John Wiley & Sons, New York, N.Y., 2001.

References in the specification to "one embodiment", "an embodiment", "an example embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect such aspect, feature, structure, moiety, or characteristic in connection with other embodiments, whether or not explicitly described.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X.

The term "about" can refer to a variation of +5%, 10%, or 20% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment. In addition, unless indicated otherwise herein, a recited range (e.g., weight percents or carbon groups) includes each specific value, integer, decimal, or identity within the range.

The phrase "one or more" is readily understood by one of skill in the art, particularly when read in context of its usage. For example, the phrase 'one or more substituents' on a phenyl ring refers to one to five, or one to up to four, for example if the phenyl ring is disubstituted.

As used herein, "contacting" refers to the act of touching, making contact, or of bringing to immediate or close proximity, including at the molecular level, for example, to bring about a chemical reaction or physical change, e.g., in a solution or other reaction mixture.

An "effective amount" generally means an amount which provides the desired effect.

Specific values listed below for radicals, substituents, and ranges, are for illustration only; they do not exclude other defined values or other values within defined ranges for radicals and substituents.

The term "alkyl" refers to a branched or unbranched hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl (iso-propyl), 1-butyl, 2-methyl-1-propyl (isobutyl), 2-butyl (sec-butyl), 2-methyl-2-propyl (t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be a monovalent hydrocarbon radical, as described and exemplified above, or it can be a divalent hydrocarbon radical (i.e., an alkylene).

The term "cycloalkyl" refers to cyclic alkyl groups of, for example, from 3 to 10 carbon atoms having a single cyclic ring or multiple condensed rings. Cycloalkyl groups include, by way of example, single ring structures such as cyclopropyl, cyclobutyl, cyclopentyl, cyclooctyl, and the like, or multiple ring structures such as adamantyl, and the like. The cycloalkyl group can be monovalent or divalent, and can be optionally substituted, for example, by one or more alkyl groups. The cycloalkyl group can optionally include one or more cites of unsaturation, for example, the cycloalkyl group can include one or more carbon-carbon double bonds, such as, for example, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, and the like.

The term "alkenyl" refers to a partially unsaturated alkyl group (i.e. an alkyl that includes at least one carbon-carbon, sp$^2$ double bond). The alkenyl group can include 2 to about 16 carbon atoms, 2 to 10 carbon atoms, preferably 2 to 6 carbon atoms, and more preferably from 2 to 4 carbon atoms. Examples include, but are not limited to, ethylene or vinyl, allyl, cyclopentenyl, and 5-hexenyl. The alkenyl can be unsubstituted or substituted, for example, by one or more alkyl groups. The alkenyl can be a substituent (monoradical) or an internal group (an alkenylene).

The term "alkynyl" refers to an alkyl group having a point of complete unsaturation (i.e. a carbon-carbon, sp triple bond). The alkynyl group can have 2 to about 16 carbon atoms, 2 to 10 carbon atoms, preferably 2 to 6 carbon atoms, and more preferably from 2 to 4 carbon atoms. This term is exemplified by groups such as ethynyl, 1-propynyl, 2-propynyl, 1-butynyl, 2-butynyl, 3-butynyl, 1-hexynyl, 2-hexynyl, 3-hexynyl, and the like. The alkynyl can be unsubstituted or substituted, for example, by one or more alkyl groups. The alkynyl can be a substituent (monoradical) or an internal group (an alkynylene).

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 18 carbon atoms, for example, about 6-10 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, for example, by one or more alkyl groups.

The term "heterocycle" refers to a saturated or partially unsaturated ring system, containing at least one heteroatom selected from the group oxygen, nitrogen, silicon, and sulfur, and optionally substituted with one or more suitable groups as defined for the term "substituted". A heterocycle can be a monocyclic, bicyclic, or tricyclic group. A heterocycle group also can contain an oxo group (=O) or a thioxo (=S) group attached to the ring. Non-limiting examples of heterocycle groups include 1,3-dihydrobenzofuran, 1,3-dioxolane, 1,4-dioxane, 1,4-dithiane, 2H-pyran, 2-pyrazoline, 4H-pyran, chromanyl, imidazolidinyl, imidazolinyl, triazolyl, indolinyl, isochromanyl, isoindolinyl, morpholinyl, piperazinyl, piperidinyl, pyrazolidinyl, pyrazolinyl, pyrrolidine, pyrroline, quinuclidine, tetrahydrofuranyl, and thiomorpholine. Divalent heterocycles can be used in the linkers of the compounds of the invention. In some embodiments, a heterocycle can be a heteroaryl.

The term "heteroaryl" refers to a monocyclic, bicyclic, or tricyclic ring system containing one, two, or three aromatic rings and containing at least one nitrogen, oxygen, or sulfur atom in an aromatic ring, and that can be unsubstituted or substituted, for example, with one or more, and in particular one to three, substituents, as described in the definition of "substituted". Typical heteroaryl groups contain 2-20 carbon atoms in addition to the one or more hetoeroatoms. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, chromenyl, cinnolinyl, dibenzo[b,d]furanyl, furazanyl, furyl, imidazolyl, imidizolyl, indazolyl, indolisinyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrimidinyl, pyrrolyl, quinazolinyl, quinolyl, quinoxalinyl, thiadiazolyl, thianthrenyl, thiazolyl, thienyl, triazolyl, tetrazolyl, and xanthenyl. In one embodiment the term "heteroaryl" denotes a monocyclic aromatic ring containing five or six ring atoms containing carbon and 1, 2, 3, or 4 heteroatoms independently selected from non-peroxide oxygen, sulfur, and N(Z) wherein Z is absent or is H, O, alkyl, aryl, or ($C_1$-$C_6$) alkylaryl. In some embodiments, heteroaryl denotes an ortho-fused bicyclic heterocycle of about eight to ten ring atoms derived therefrom, particularly a benz-derivative or one derived by fusing a propylene, trimethylene, or tetramethylene diradical thereto.

Compounds of Formula I can include a linker between the steroid skeleton and the polar group. Linkers can separate the residue of a compound of Formula I and a polar group by a suitable distance, such as by about 5 angstroms to about 200 angstroms. Other suitable linkers include linkers that separate the residue of a compound of Formula I and a saccharide by about 5 angstroms to about 100 angstroms. The linker can be a divalent radical of the formula —W-A-W— wherein W is —N(R')C(=O)—, —C(=O)N(R')—, —OC(=O)—, —C(=O)O—, —O—, —S—, —S(O)—, —S(O)$_2$—, —N(R')—, —C(=O)—, a direct bond, or absent; wherein each R' is independently H, (C$_1$-C$_6$)alkyl, or a nitrogen protecting group; and A can be (C$_1$-C$_{20}$)alkyl, (C$_2$-C$_{16}$)alkenyl, (C$_2$-C$_{16}$)alkynyl, (C$_3$-C$_8$)cycloalkyl, (C$_6$-C$_{10}$)aryl, —(OCH$_2$—CH$_2$)$_n$— where n is 1 to about 20, —C(O)NH(CH$_2$)$_n$ wherein n is 1 to about 6, —OP(O)(OH)O—, —OP(O)(OH)O(CH$_2$)$_n$ wherein n is 1 to about 6, —OP(O)(OH)OCH$_2$CH(OH)CH$_2$—, —N$^+$(Me)$_2$(CH$_2$)$_n$ wherein n is 1 to about 6, or (C$_1$-C$_{20}$)alkyl, (C$_2$-C$_{16}$)alkenyl, (C$_2$-C$_{16}$)alkynyl, or —(OCH$_2$—CH$_2$)$_n$— interrupted between two carbons, or between a carbon and an oxygen, with one, two, or three (C$_3$-C$_8$)cycloalkyl, heterocycle, or (C$_6$-C$_{10}$)aryl groups; and A or W is linked to a saccharide or other polar group described herein. The group A can also be a polysaccharide or a peptide.

The term "residue" refers to an atom or group of atoms that are part of a larger molecule. For example, while an amino acid is a compound, an amino acid residue is the compound linked to another molecule through a covalent bond, such as by the formal removal of a hydrogen from an amino terminus or a carboxy terminus of the amino acid, to form a direct bond with the other molecule. A residue can also refer to a portion of a molecule used to link one molecule to another molecule to form a conjugate. Typical residues of an amino acid include its amino residue and its carboxylic acid residue. Appropriate residues can often be condensed to form linkages. For example, an amino residue and a carboxylic acid residue can be condensed to form a peptide bond. A typical residue of a saccharide includes any one of its hydroxyl groups, and in several embodiments, the anomeric hydroxyl.

Compounds of Formula I with attached polar groups (e.g., glycosides, hydroxyl groups, PEG groups, amino acid groups, etc.) can be formed by reacting an appropriately functionalized polar group (e.g., functionalize with a leaving group) with a hydroxyl group of the appropriate Formula I precursor under appropriate reaction conditions (e.g., basic or acidic, depending on the reactivity of the functionalized polar group). A polar group, as used herein, can refer to a monosaccharide, a disaccharide, or any other polar group described herein.

The term "polar group" refers to a group having a permanent electric dipole moment. Polar groups are well known in the art of membrane solubilization. Polar groups can be neutral, anionic, cationic, or zwitterionic. Suitable polar groups can include, but are not limited to, hydroxyl groups, carboxylic acid groups, thiols, —S(O)OH, —S(O)$_2$OH, —OS(O)$_2$OH, —P(OH)$_2$, —P(O)OH, —OP(O)OH$_2$, —N$^+$H$_3$, —N$^+$(Me)$_3$, —N$^+$(Me)$_2$-O$^-$, —(OCH$_2$CH$_2$)$_n$—OH where n is 1 to about 20, —(OCH$_2$CH$_2$)$_n$—O(alkyl) where n is 1 to about 20, a saccharide, an amino acid, or a peptide. The polar group can be one of the aforementioned groups, or the polar group can terminate in one of the aforementioned groups, and include one or more linking groups as defined herein, including —O—, —NH—, —C(O)NH—, —C(O)NH(CH$_2$)$_n$ wherein n is 1 to about 6, —OP(O)(OH)O—, —OP(O)(OH)O(CH$_2$)$_n$— wherein n is 1 to about 6, —OP(O)(OH)OCH$_2$CH(OH)CH$_2$—, or —N$^+$(Me)$_2$(CH$_2$)$_n$ wherein n is 1 to about 6. When any group includes the variable "n", for example, where n can be 1 to about 6, each n can independently be 1, 2, 3, 4, 5, or 6, or any integer in the recited range.

A saccharide can be a polar group. The term "saccharide" refers to a sugar or sugar moiety, such as a monosaccharide or a disaccharide. Typical monosaccharides include allose, altrose, glucose, mannose, gulose, idose, galactose, or talose. Typical disaccharides include sucrose, lactose, maltose, trehalose, and cellobiose. Disaccharides can have any suitable linkage between the first and the second unit of the disaccharide. Other suitable saccharides include glucuronic acid, sorbase, ribose, and the like. A saccharide can include hydroxyl protecting groups such as, but not limited to, acetyl groups, benzyl groups, benzylidene groups, silyl groups, methoxy ether groups, or combinations thereof. The saccharide groups can also be in pyranose form, furanose form, or linear form. The saccharides can be linked to Formula I via their anomeric oxygen, or to any other available hydroxyl group. Depending on the context, as would be understood by one of skill in the art, the saccharide can include the oxygen that links it to another group, or exclude the oxygen that links it to another group.

An amino acid can be a polar group. The term "amino acid" refers to a natural amino acid residue (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as an unnatural amino acid (e.g. phosphoserine; phosphothreonine; phosphotyrosine; hydroxyproline; gamma-carboxyglutamate; hippuric acid; octahydroindole-2-carboxylic acid; statine; 1,2,3,4,-tetrahydroisoquinoline-3-carboxylic acid; penicillamine; ornithine; citruline; α-methyl-alanine; para-benzoylphenylalanine; phenylglycine; propargylglycine; sarcosine; tert-butylglycine; and 2,5-diaminohexanedioic acid) residue having one or more open valences. The term also comprises natural and unnatural amino acids bearing amino protecting groups (e.g. acetyl, acyl, trifluoroacetyl, or benzyloxycarbonyl), as well as natural and unnatural amino acids protected at carboxy with protecting groups (e.g. as a (C$_1$-C$_6$) alkyl, phenyl or benzyl ester or amide). Other suitable amino and carboxy protecting groups are known to those skilled in the art (see for example, T. W. Greene, *Protecting Groups In Organic Synthesis*; Wiley: New York, Third Edition, 1999, and references cited therein; D. Voet, *Biochemistry*, Wiley: New York, 1990; L. Stryer, *Biochemistry*, (3rd Ed.), W.H. Freeman and Co.: New York, 1975; J. March, *Advanced Organic Chemistry, Reactions, Mechanisms and Structure*, (2nd Ed.), McGraw Hill: New York, 1977; F. Carey and R. Sundberg, *Advanced Organic Chemistry, Part B: Reactions and Synthesis*, (2nd Ed.), Plenum: New York, 1977; and references cited therein). Specific useful protecting groups include benzyl, acetyl, trifluoroacetyl, benzoyl, benzyloxycarbonyl, and silicon protecting groups such as trimethylsilyl, t-butyldimethylsilyl, and diphenylmethylsilyl.

A peptide can be a polar group. The term "peptide" describes a sequence of 2 to 25 amino acids (e.g. as defined herein) or peptidyl residues. The sequence may be linear or cyclic. For example, a cyclic peptide can be prepared or may result from the formation of disulfide bridges between two cysteine residues in a sequence. A peptide can be linked to the remainder of a compound of formula I through the carboxy terminus, the amino terminus, or through any other convenient point of attachment, such as, for example, through the sulfur of a cysteine. Preferably a peptide comprises 3 to 25, or 5 to 21 amino acids. Peptide derivatives can be prepared as disclosed in U.S. Pat. No. 4,612,302 (Szabo et al.); U.S. Pat. No. 4,853,371 (Coy et al.); or U.S. Pat. No. 4,684,620 (Hruby et al.).

A poly(ethylene glycol) can be a polar group. The term "poly(ethylene glycol)" or "PEG" refers to the group —$(OCH_2CH_2)_n$OH wherein n is 2 to about 1,000, or a derivative thereof. It can be attached to a compound of Formula I through a terminal hydroxyl group of the PEG, or through another group that has replaced a terminal oxygen atom or hydroxyl group. In various embodiments, the molecular weight of the PEG chain can be about 100 to about 200,000, or about 250 to about 100,000. In certain embodiments, the PEG group can have a molecular weight of about 500 to about 20,000; about 2,000 to about 15,000; about 3,500 to about 12,000; or about 3,000 to about 9,000. In other embodiments, the PEG groups can have a molecular weight of about 4,000 or about 7,000. In yet other embodiments, "n" of a PEG group (the number of repeating units) can be about 2, 3, 4, 5, 6, 7, 8, 9, 10, 11, 12, 13, 14, 15, 16, 17, 18, 19, 20, 25, 30, 40, or 50. The PEG group can be capped at its terminal end with a protecting group, such as an acetyl group or an alkyl group, for example, a methyl or an ethyl group.

As to any of the compounds described herein, it will be appreciated that the compounds of the invention may include asymmetrically substituted carbon atoms, and may be isolated in optically active or racemic forms. It is well known in the art how to prepare optically active forms, such as by resolution of racemic forms or by synthesis from optically active starting materials. All chiral, diastereomeric, racemic forms and all geometric isomeric forms of a structure are part of this invention.

One diastereomer may display superior activity compared with another. When required, separation of the racemic material can be achieved by high pressure liquid chromatography (HPLC) using a chiral column or by a resolution using a resolving agent such as camphonic chloride as in Thomas J. Tucker, et al., *J. Med. Chem.* 1994, 37, 2437-2444. A chiral compound may also be directly synthesized using a chiral catalyst or a chiral ligand; see, for example, Mark A. Huffman, et al., *J. Org. Chem.* 1995, 60, 1590-1594.

Facial Amphiphiles of the Invention

The new design of steroid-based facial amphiphiles features concurrent modification of both the carboxylic acid and hydroxyl groups, for example, of cholic acid and deoxycholic acid (e.g., Structural Classes A-E, described below). The removal of the carboxylic acid group leads to a short flexible alkyl chain appended to the rigid steroid cycles. The length of the alkyl chain can be increased through coupling to other alkyls (e.g., to form an alkyl group of up to about 20 carbon atoms in length). The alkyl chain may contain branches and/or cycloalkyl groups. Also, the hydroxyl groups can be covalently attached, directly or through a short linker (e.g., oxygen, nitrogen, ethylene glycol, ($C_1$-$C_4$)alkyl, etc.), to other polar groups to install polar components of the amphiphile "underneath" the nonpolar steroid plane (or slightly concave face of the steroid framework).

The polar groups cover a substantial area under the steroid skeleton, creating a "sandwich" or "facial" amphiphilic structure that is distinct from the polar-head/nonpolar-tail design of most standard detergents. The polar groups can be neutral, zwitterionic, or charged. The 3α-OH group in cholic acid can be selectively protected and/or removed, leaving the two central 7α- and 12α-OH groups intact, which leads to the synthesis of facial amphiphiles with two polar groups (Classes A and B, with or without the 3α-OH) or three polar groups (Class C) polar heads. Similarly, Classes D and E can be prepared from deoxycholic acid by selective installation of a new polar group at the various hydroxyls, as appropriate. The classes can be further varied by modifying the carboxylic acid moiety of cholic acid or deoxycholic acid so that an alkyl chain of a desired length can be appended to this moiety of the amphiphile. The non-polar group can be a straight chain, branched, or cyclic alkyl group, and the group can optionally be substituted with other non-polar groups, such as phenyl groups.

Class A. 3-Deoxy Amphiphilies:

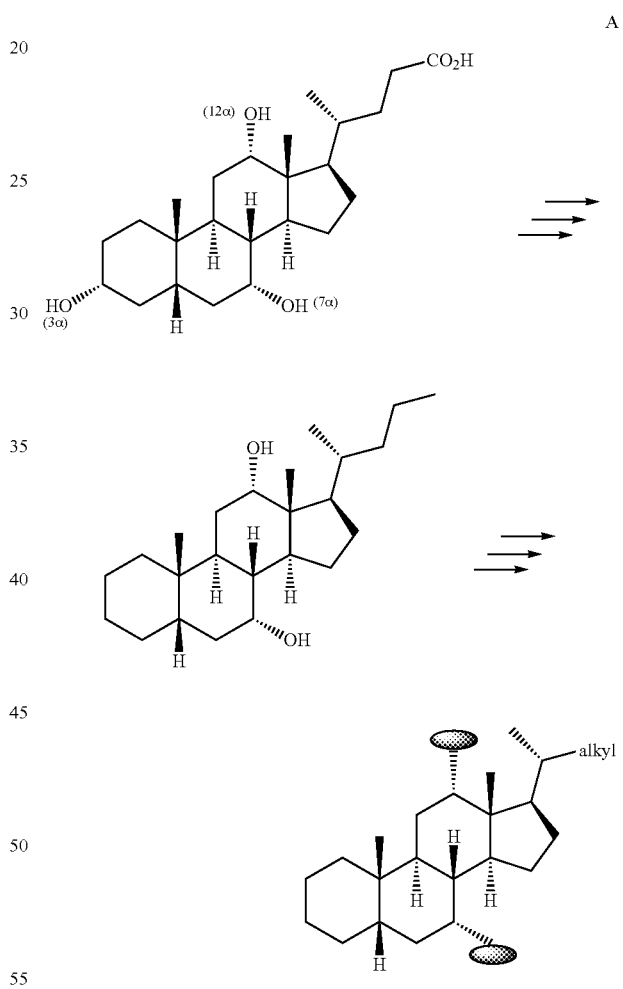

wherein ● represents a polar group attached to the 7α and 12α positions of the cholic acid backbone through hydroxyl group moieties or through a linker. Each polar group ● referred to in any class can be the same or different than other polar groups on the amphiphile. In some embodiments, the polar group can be hydroxyl. In other embodiments, the polar group will be a polar group other than hydroxyl. In some embodiments, the polar groups can be a combination of hydroxyl groups and/or other polar groups. Specific examples of Class A amphiphiles include the following compounds:

13
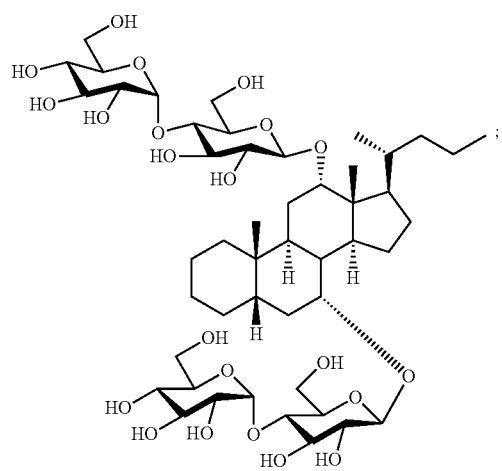
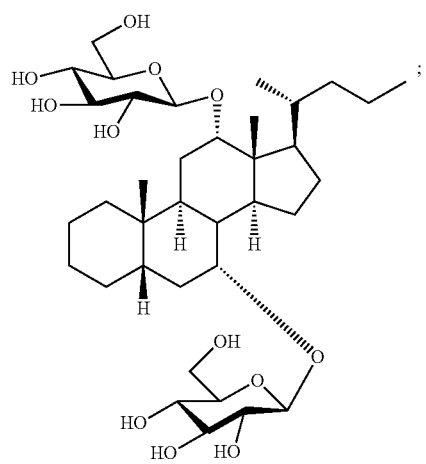
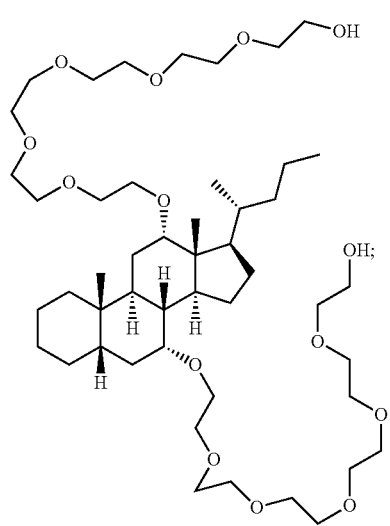
14
A1
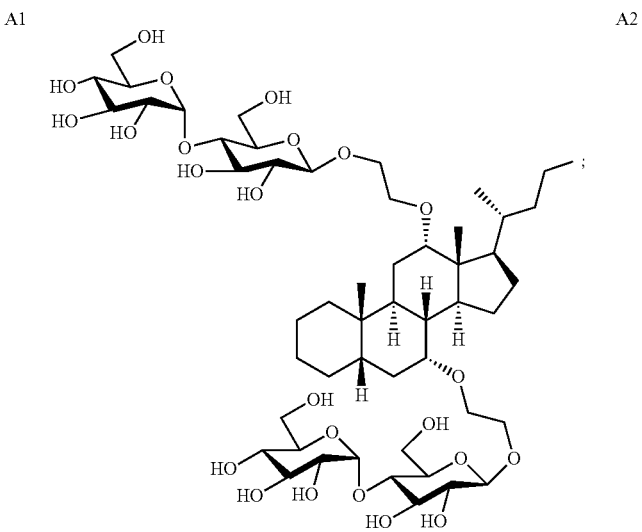
A2
A3
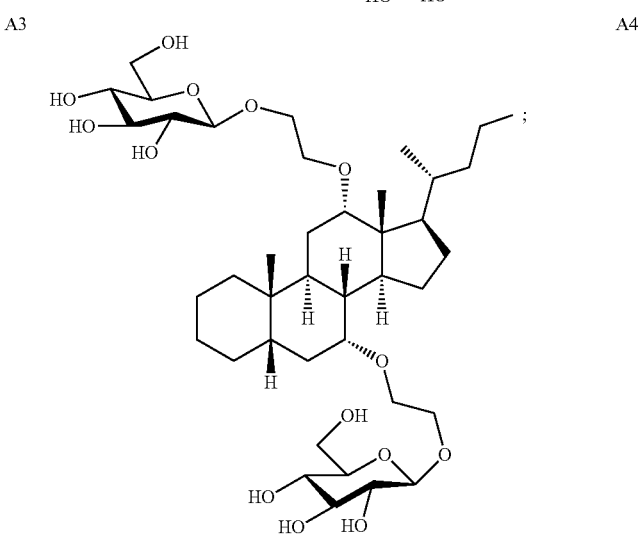
A4
A5
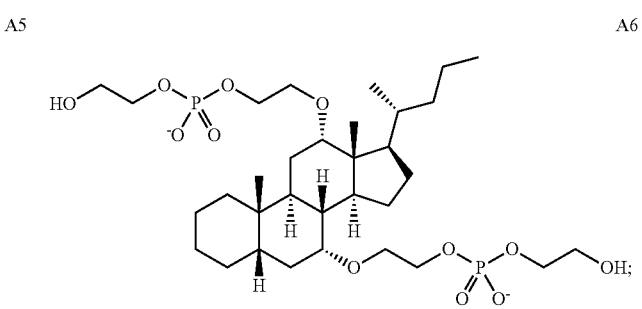
A6

Class B. 3-Hydroxy Amphiphiles:
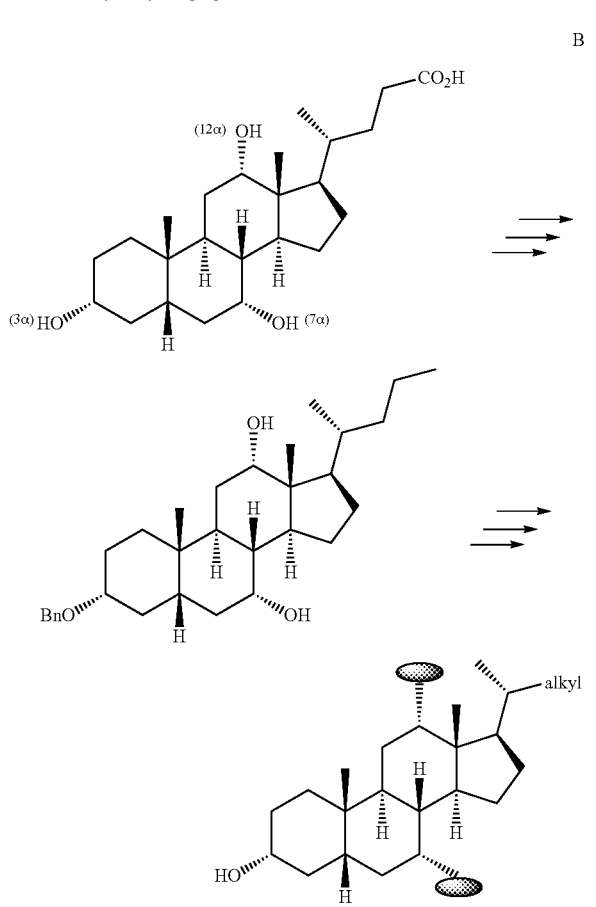
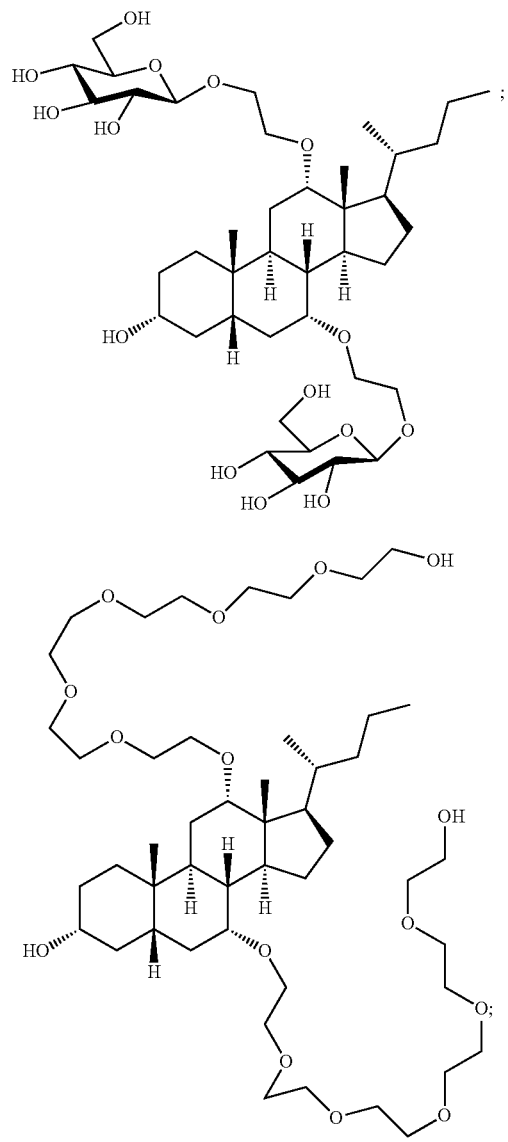
wherein ⬤ represents a polar group attached to the 7α and 12α positions of the cholic acid backbone through hydroxyl group moieties or through a linker. Specific examples of Class B amphiphiles include the following compounds:
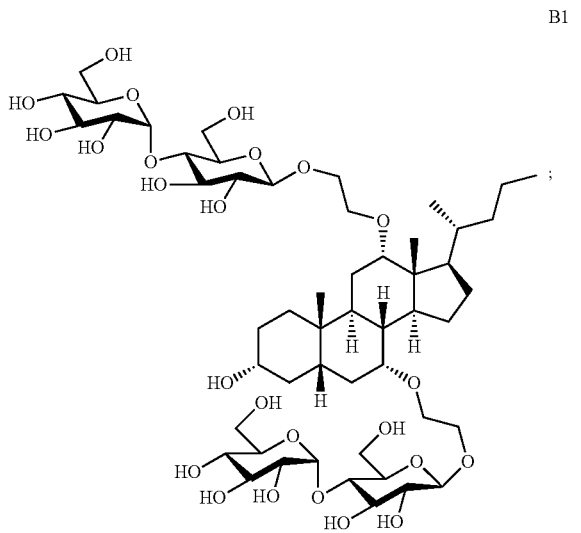
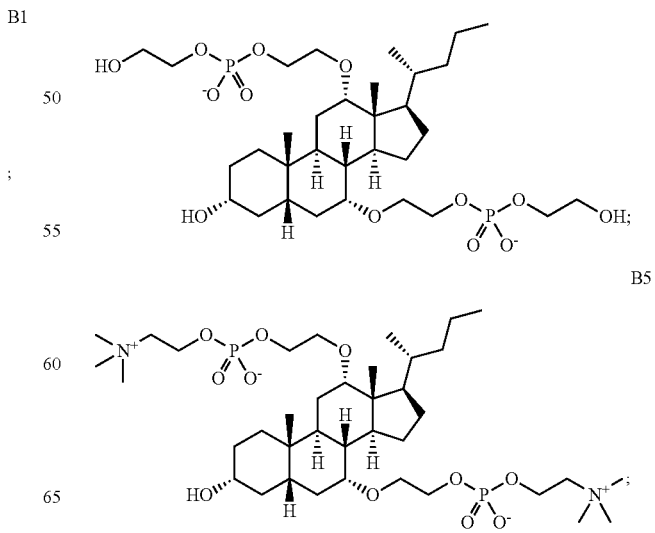

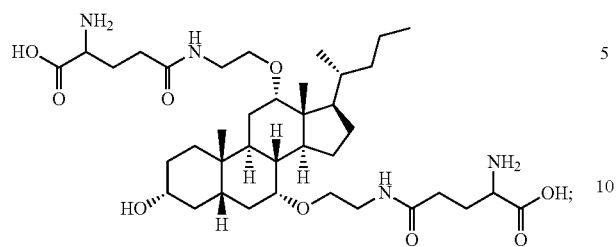
B6
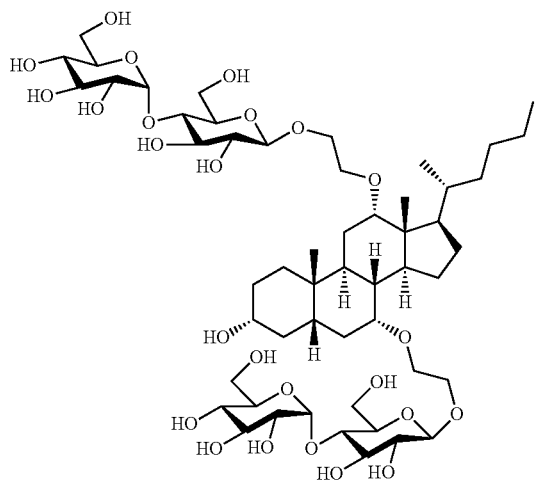
B9
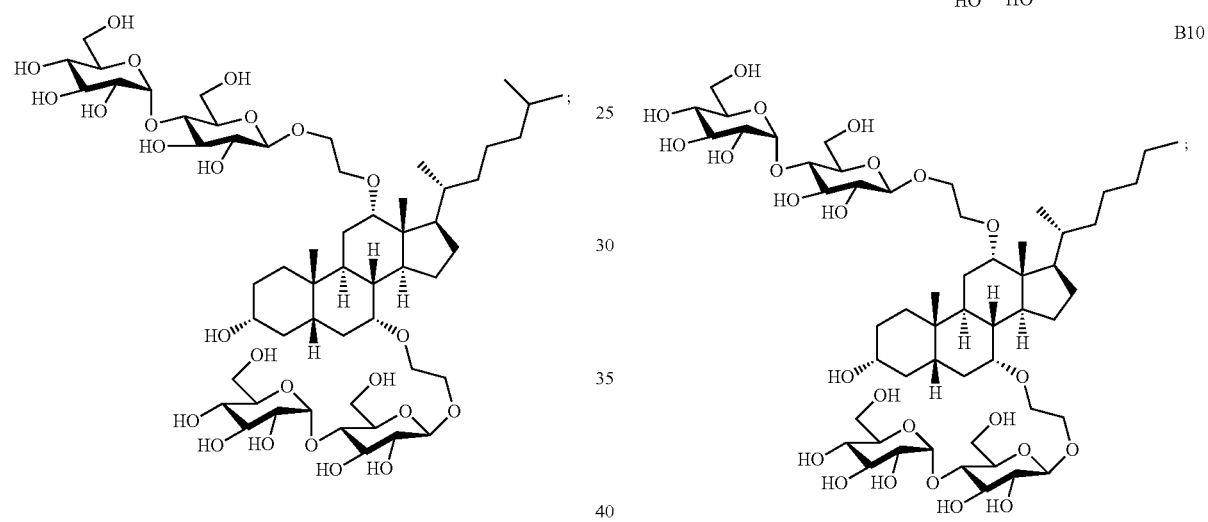
B7
B10
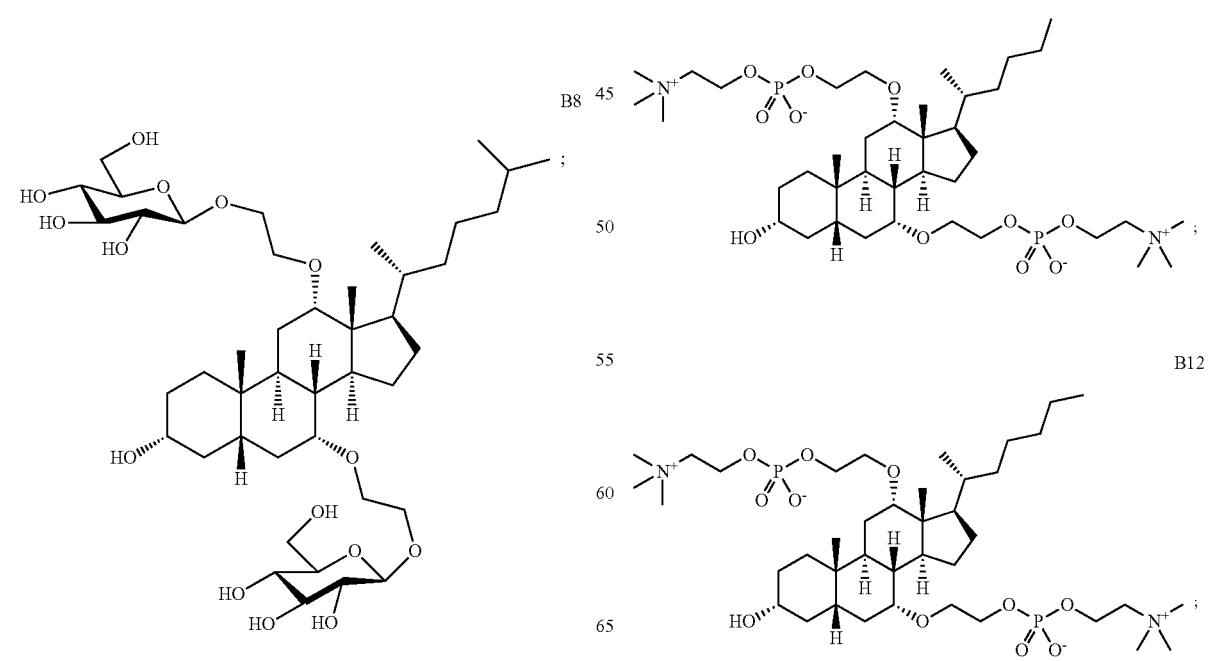
B8
B11
B12

-continued
B13
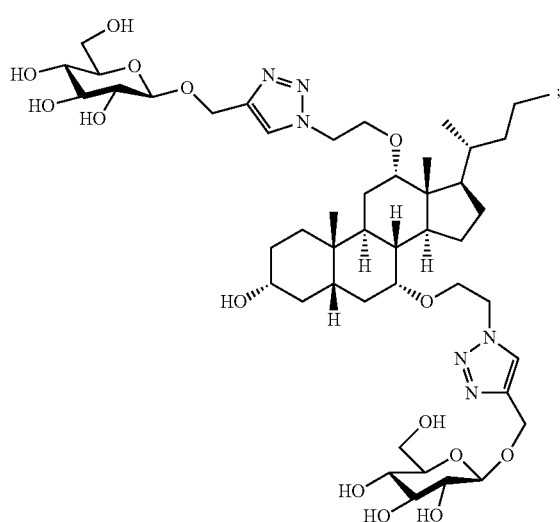
B14
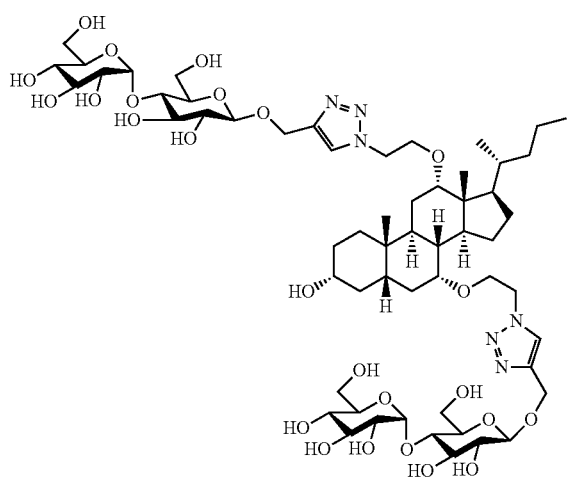
B15
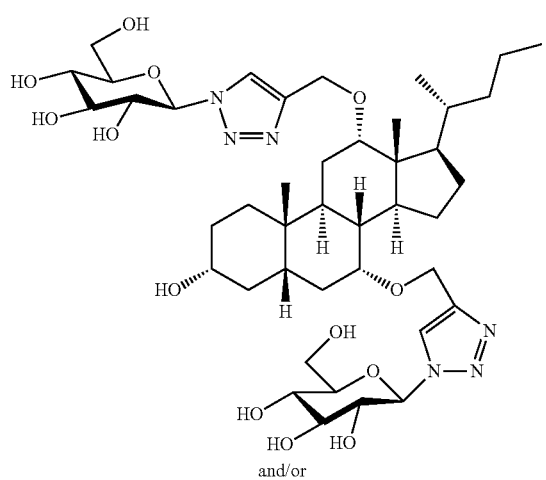
and/or
-continued
B16
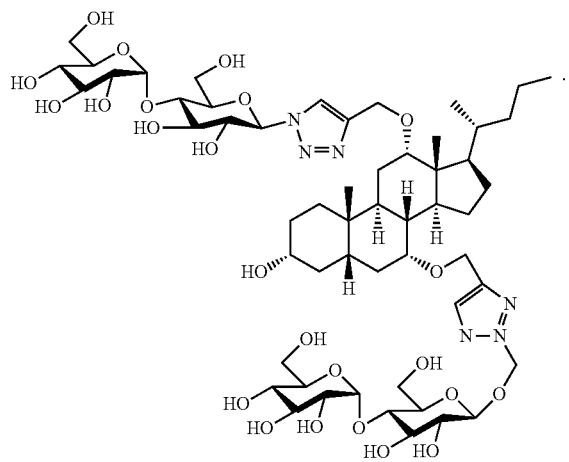
Class C. Tri-polar Amphiphiles:
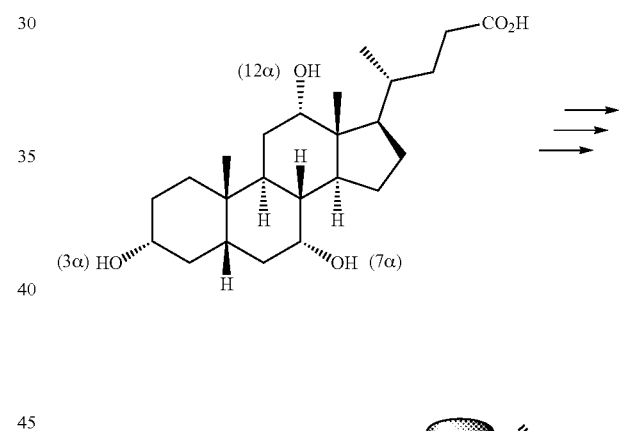
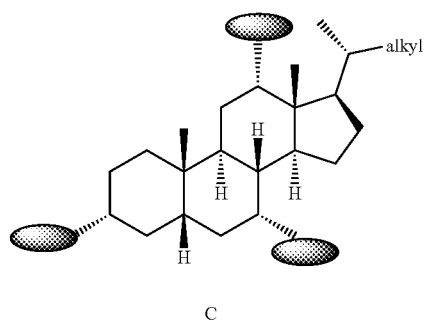
C
wherein ⬭ represents a polar group attached to the 3α, 7α and 12α positions of the cholic acid backbone through hydroxyl group moieties or through a linker. Specific examples of Class C amphiphiles include the following compounds:

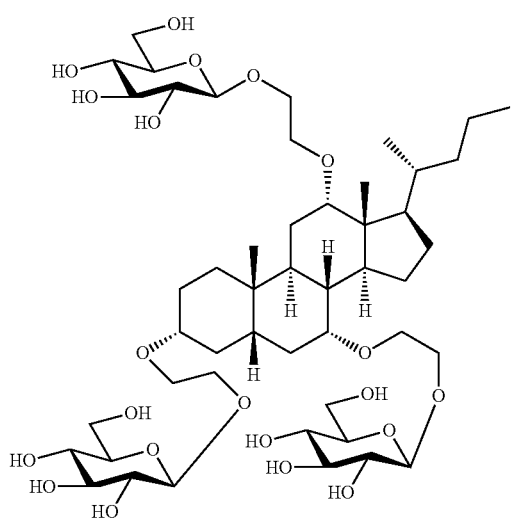
C1
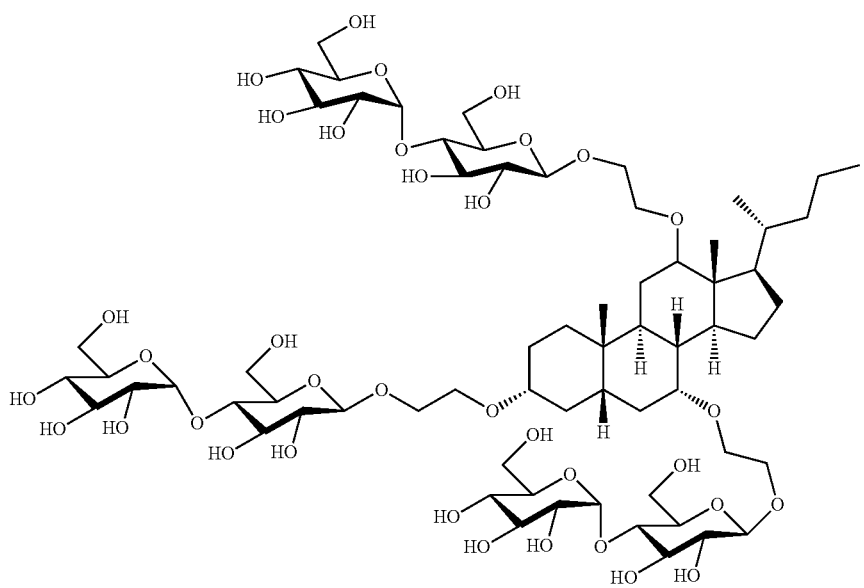
C2
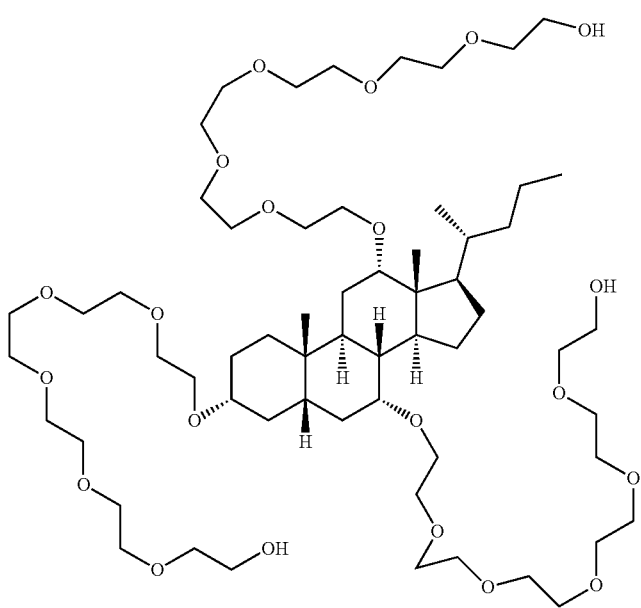
C3

-continued
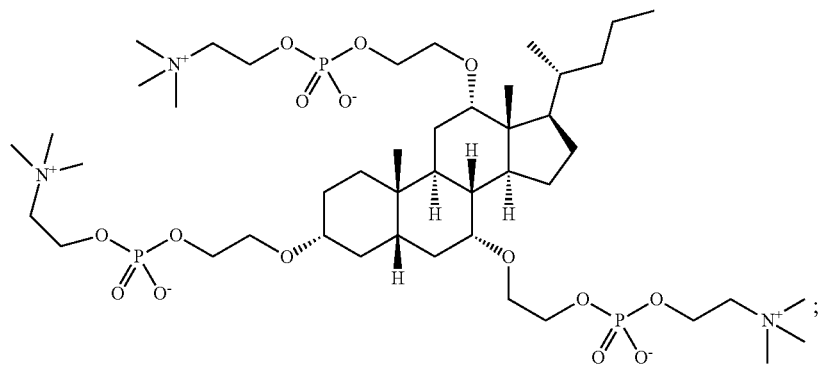
C4
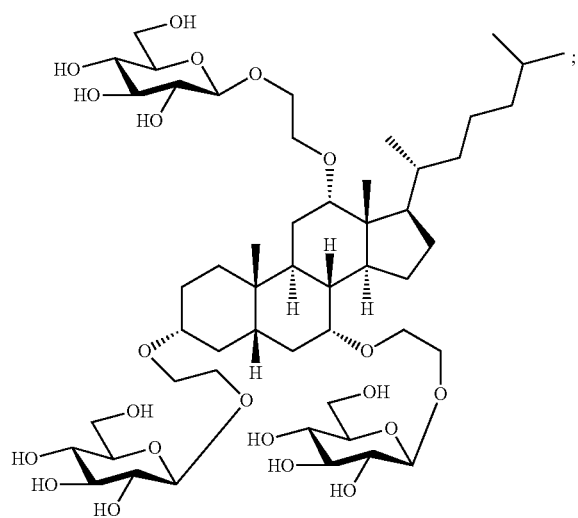
C5
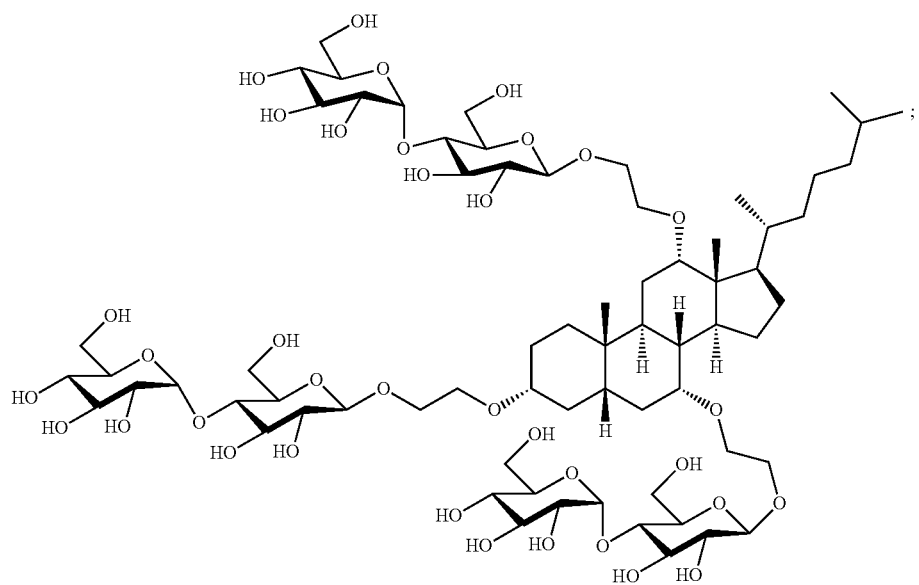
C6

-continued
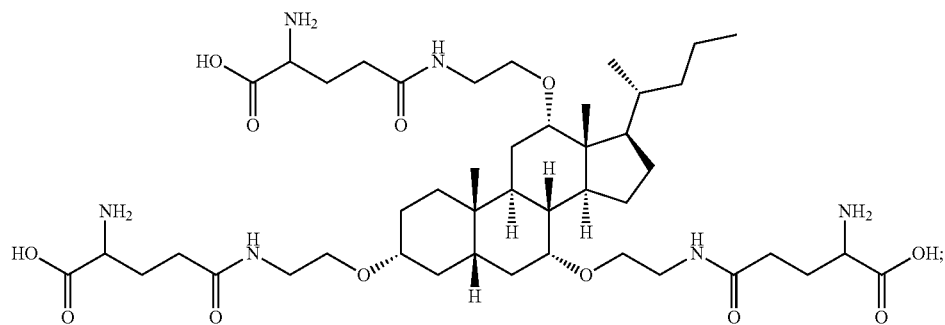
C7
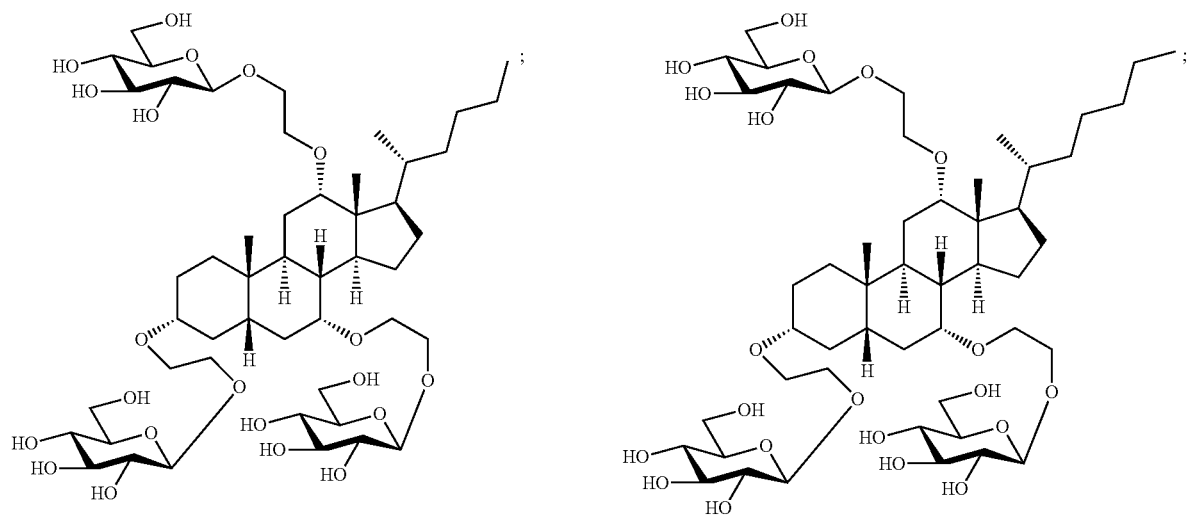
C8
C9
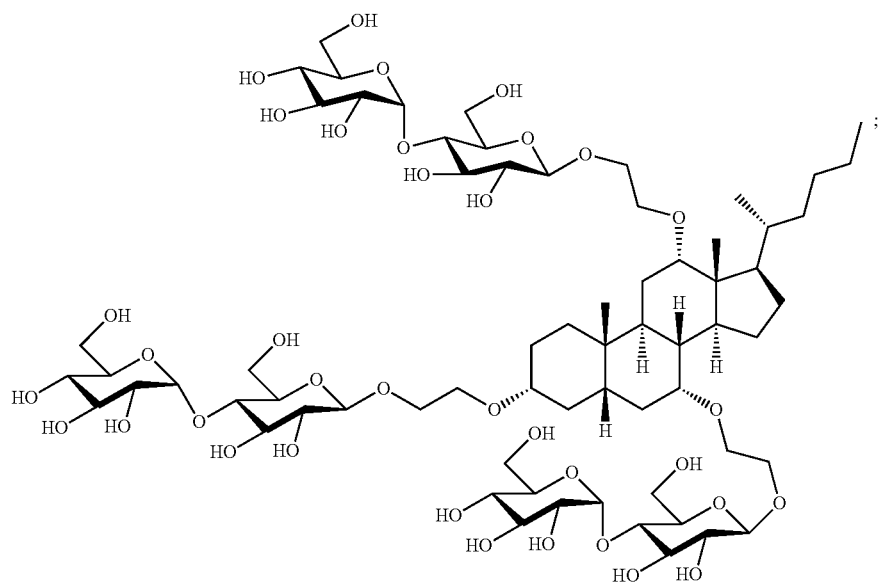
C10

-continued
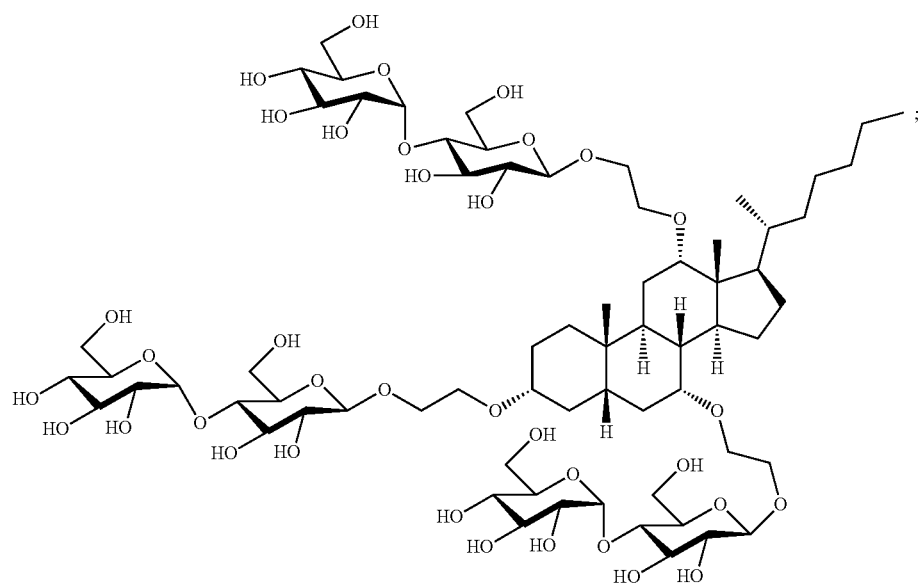
C11
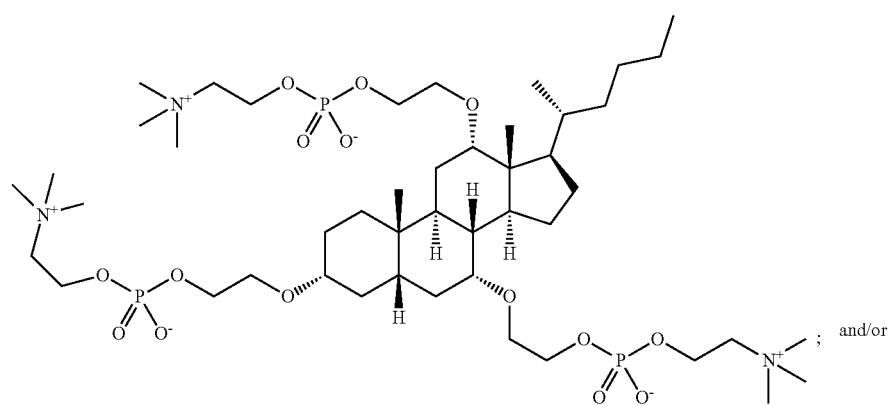
C12
; and/or
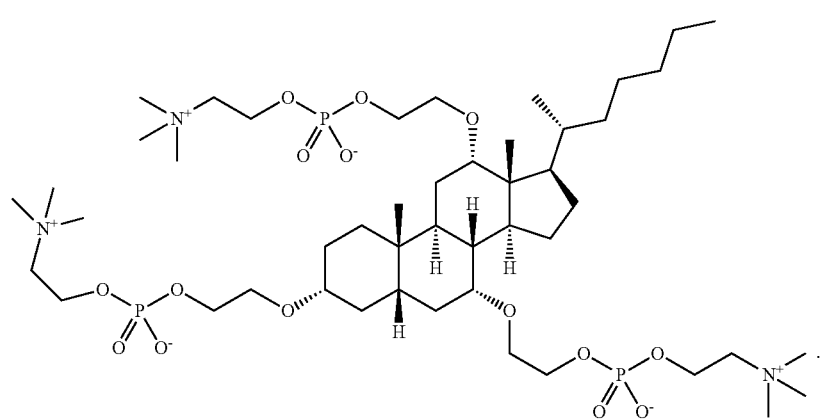
C13

Class D. 3-Hydroxy-7-Deoxy Amphiphiles:

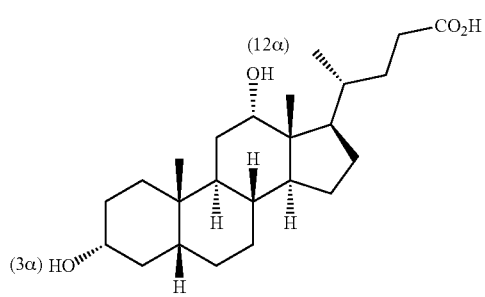

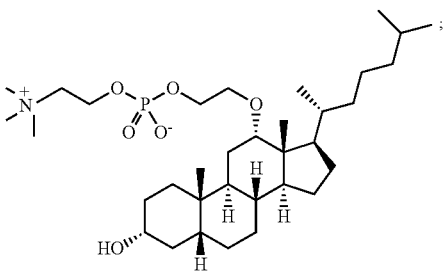

-continued and/or

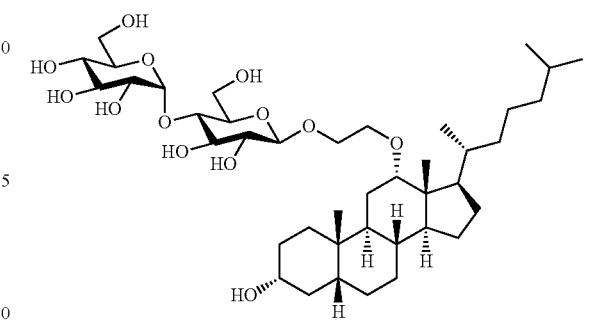

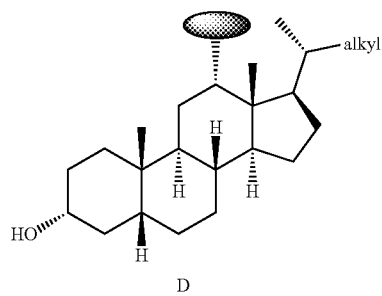

D wherein ▨ represents a polar group attached to the 7α positions of the deoxycholic acid backbone through hydroxyl group moieties or through a linker. Specific examples of Class D amphiphiles include the following compounds:

D1

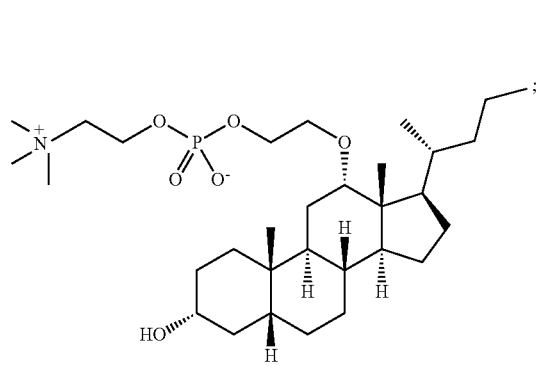

Class E. 7-Deoxy Amphiphiles:

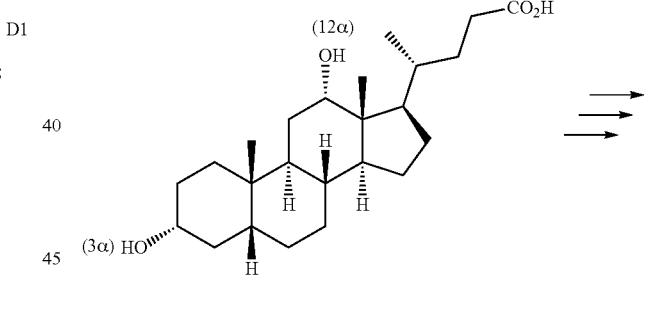

D2

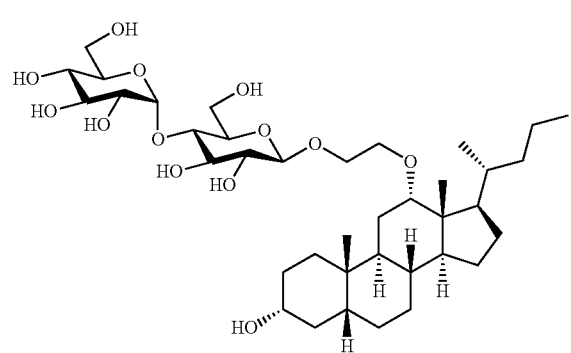

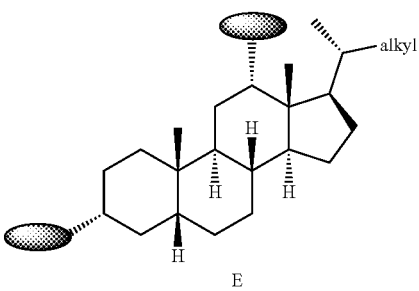

E wherein ▨ represents a polar group attached to the 3α and 12α positions of the deoxycholic acid backbone through hydroxyl group moieties or through a linker. Specific examples of Class E amphiphiles include the following compounds:

31 32
E1
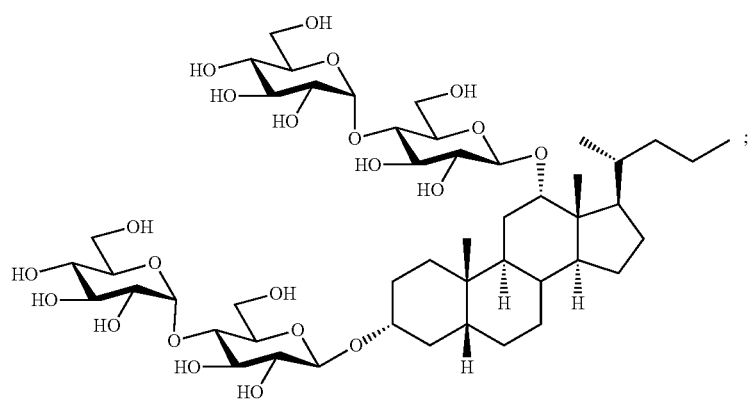
E2
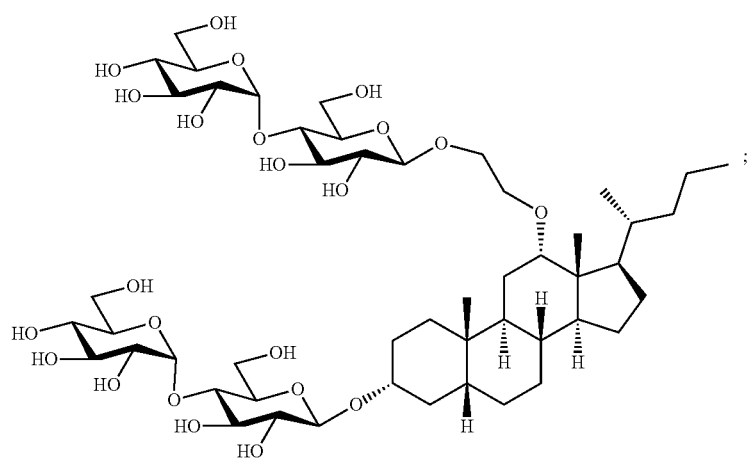
E3
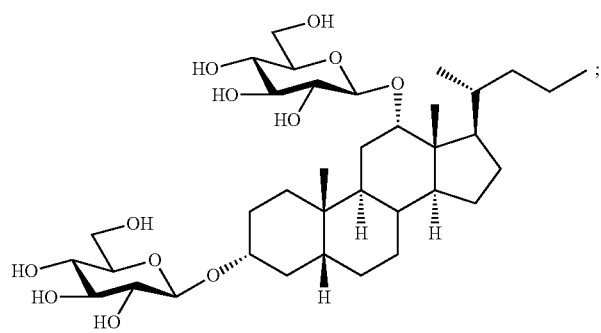
E4
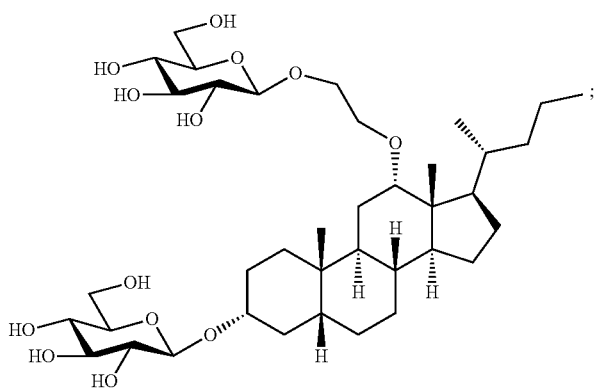

-continued

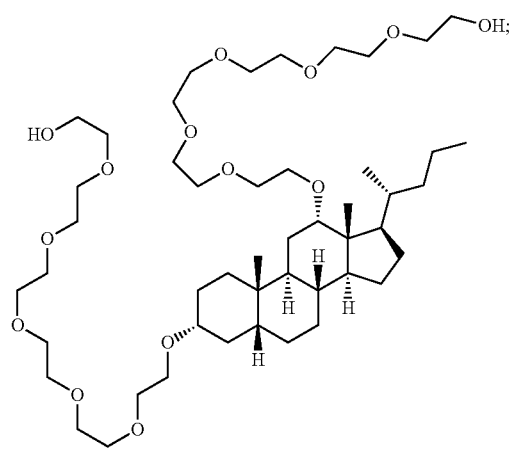
E5

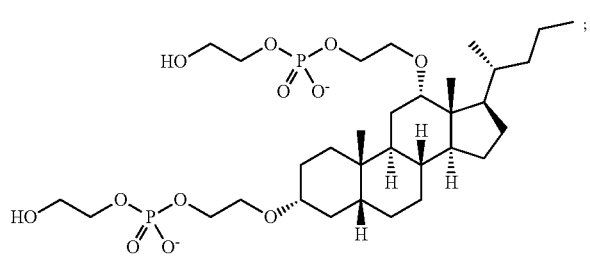
E6

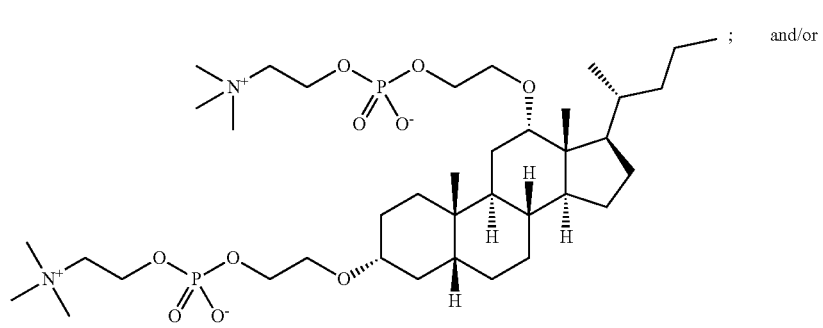
E7 ; and/or

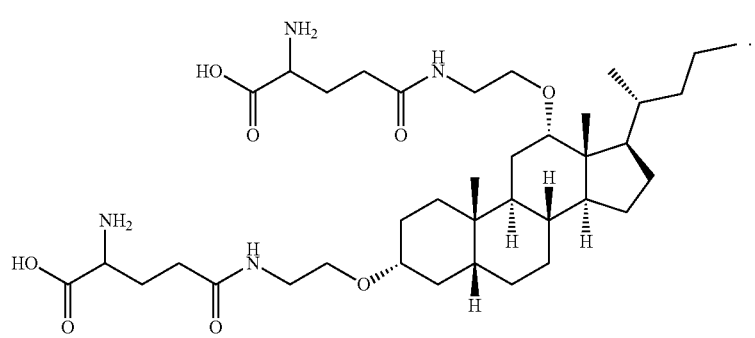
E8

Other polar groups that can be attached to the 3α, 7α, and/or 12α positions of the cholate backbone include the groups illustrated in Table 1, according to various embodiments. As would be readily recognized by one skilled in the art, certain anionic or cationic groups may become neutral under certain conditions, for example, at an appropriate pH, or in the presence of a suitable counterion.

TABLE 1

Polar Groups

⬭ = Polar groups (structure shown below), attached to 3α, 7α and/or 12α positions through hydroxyl groups or a linker;
R = the remainder of a compound of formula I Anionic 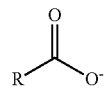

TABLE 1-continued

Polar Groups

⬭ = Polar groups (structure shown below), attached to 3α, 7α and/or 12α positions through hydroxyl groups or a linker;
R = the remainder of a compound of formula I

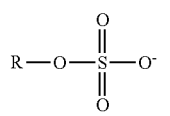

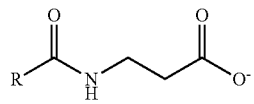

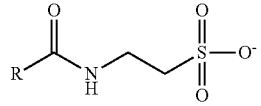

TABLE 1-continued

Polar Groups
⬛ = Polar groups (structure shown below), attached to 3α, 7α and/or 12α positions through hydroxyl groups or a linker; R = the remainder of a compound of formula I $$R-O-\overset{O^-}{\underset{\underset{O}{\|}}{P}}-O\diagup\diagdown OH$$
$$\phantom{R-O-P-O}OH$$

$$R-O-\overset{O^-}{\underset{\underset{O}{\|}}{P}}-O\diagup\diagdown OH$$

Cationic $$R-\overset{|}{\underset{|}{N^+}}-$$

Zwitterionic $$R-\overset{|}{\underset{|}{N^+}}\diagdown\diagup\overset{O}{\underset{}{\|}}\diagdown O^-$$

$$R-\overset{|}{\underset{|}{N^+}}\diagdown\diagup\diagdown SO_3^-$$

$$R-O-\overset{O^-}{\underset{\underset{O}{\|}}{P}}-O\diagdown\diagup\overset{|}{\underset{|}{N^+}}-$$

$$R-O-\overset{O^-}{\underset{\underset{O}{\|}}{P}}-O\diagdown\diagup\overset{+}{NH_3}$$

$$R-\overset{+}{\underset{|}{N}}-\overset{-}{O}$$

Nonionic        $R-(OCH_2CH_2)_n-OH$ sugars
peptides

The new steroid-based facial amphiphiles can stabilize integral membrane proteins (IMPs) in functional states and in protein structural characterization. The amphiphiles can extract proteins from lipid bilayers and provide substantially increased protein stability compared to conventional detergents. Data shows that membrane proteins can be crystallized in the presence of the facial amphiphiles of the invention. Suitable data has been obtained at 2 Å resolution. The facial amphiphiles can also be used for small angle X-ray scattering (SAXS) studies. Such studies are difficult, if not impossible, with the known detergents. The facial amphiphiles of the invention can further be used for membrane protein research including, but are not limited to, solution NMR studies, micelle preparation (detergent-lipid mixtures), and biochemical and biophysical assay development.

The facial amphiphiles described herein are structurally distinct from the classical head-to-tail detergents, including the previously known steroid-based amphiphiles. In comparison with cholate and related known facial amphiphiles, the newly designed molecules have increased facial amphiphilicity and a flexible alkyl chain that better mimics the cholesterol molecular structure. Compounds of the invention can provide a more membrane-like environment than classical detergents when complexed with membrane proteins. They can impart surprisingly significant stability when used to solubilize integral membrane proteins. The compounds have large and relatively flat hydrophobic surfaces, and promote the formation of stable and small membrane protein-detergent complexes, which are favorable for myriad applications. Consistent with these advantages, experimental data show that the amphiphiles are useful in both small angle X-ray scattering and in crystallization trials.

The modest cost of preparation of the new detergents is also a favorable compared to known detergents used in the art. Cholic acid and deoxycholic acid are inexpensive starting materials for the synthesis of the described molecules. Preparation of the compounds of the invention has been accomplished on a large scale in several cases. The compounds can be used alone, or in combination with lipids or known detergents, such as CHAPS and CHAPSO, or other detergents described by Hjelmeland in *Methods of Enzymology*, Vol. 124, page 135-164, which is incorporated herein by reference.

Compounds of the invention have solubilized several membrane proteins with substantially improved stability relative to cholate and other conventional detergents. See FIG. 1, which schematically illustrates facial amphiphiles stabilizing a membrane protein, according to an embodiment of the invention. The facial amphiphiles have also been used for membrane protein crystallization and for small-angle X-ray scattering studies, significantly aiding the crystallization and characterization compared to known detergents.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Preparation of Amphiphiles, Classes A-E

General procedure. NMR spectra were recorded on Bruker DRX-500, AMX-500 or AMX-300 instruments. IR spectra were recorded on a Perkin-Elmer 1600 series FT-IR spectrometer. High-resolution mass spectra (HRMS) were recorded on a VG ZAB-ZSE mass spectrometer using MALDI (matrix-assisted laser-desorption ionization) or ESI (electrospray ionization).

Facial amphiphile A1 was prepared with a D-maltoside unit attached to each of the 7α and 12α hydroxyl groups of the cholate skeleton. A convenient synthesis was developed by direct glycosylation of readily available dihydroxy cholane (prepared in 70% yield from cholic acid in 3 steps without column purification) as outlined in Scheme 1.

Scheme 1.
Synthesis of Di-β-D-Maltoside Cholane A1

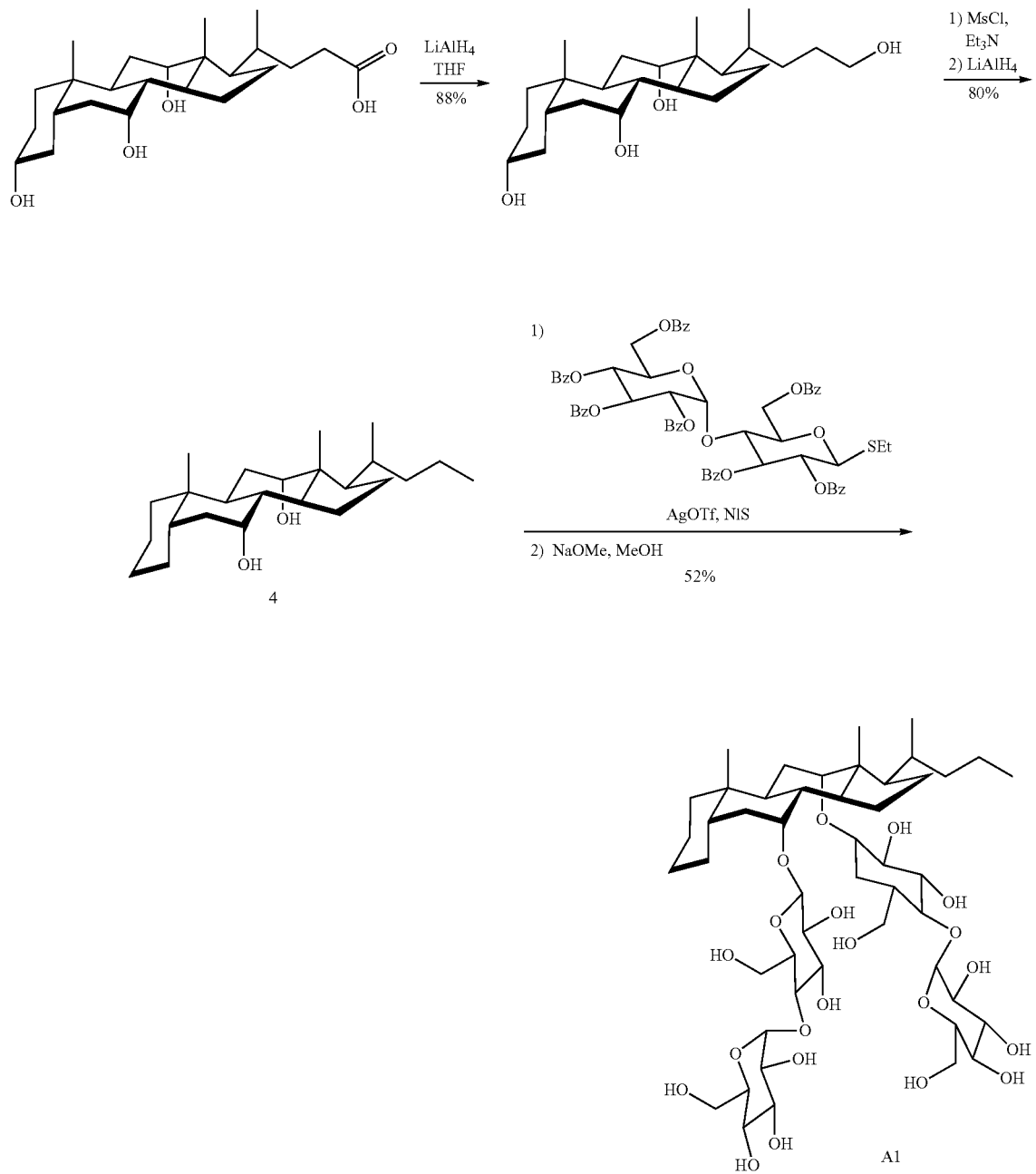

3α,7α,12α,24-Tetrahydroxycholane

To a suspension of LiAlH₄ (3.85 g, 100 mmol) in dry THF (100 mL) at 0° C. was added dropwise a solution of cholic acid (15.03 g, 35 mmol) in dry THF (200 mL) with vigorous stirring under nitrogen atmosphere. The reaction mixture was then heated to reflux with stirring for overnight. Upon completion, the reaction was carefully quenched with saturated aqueous NH₄Cl solution at RT. Then the mixture was acidified with 1N HCl to pH 1~2. The precipitate was collected via filtration and washed with water and acetone to give the product (12.1 g, 88%) as a white solid.

7α,12α-Dihydroxycholane (1)

To a solution of 3α,7α,12α,24-tetrahydroxycholane (17.4 g, 44.2 mmol) and triethylamine (11.8 g, 116.6 mmol) in dry THF (300 mL) was added dropwise a solution of methanesulfonyl chloride (11.1 g, 97.2 mmol) in dry THF (100 mL) at 0° C. Then the reaction mixture was slowly warmed up to RT. After 30 minutes, the reaction was quenched with saturated aqueous NH₄Cl solution. The organic solvents were removed under vacuum and the left aqueous solution was extracted with ethyl acetate. The combined organic portions were washed with brine and then dried over anhydrous $Na_2SO_4$. The filtered solution was concentrated under vacuum to give the product 7α,12α-Dihydro-3α,24-dimethylsulfonate-cholane (25.6 g, 95%) which was directly dissolved in dry THF for the next step.

A solution of $LiAlH_4$ (6.0 g, 158 mmol) in dry THF (300 mL) was added dropwise to the above obtained THF solution of 7α,12α-dihydro-3α,24-dimethylsulfonate-cholane at 0° C. The reaction mixture was heated to reflux with stirring for overnight. Then the reaction was quenched with saturated aqueous $NH_4Cl$ solution at RT. The organic solvents were evaporated under vacuum and the left aqueous solution was acidified with 1N HCl to pH 1. The white precipitate formed was collected via filtration, washed with water and acetone to give the crude product, and then crystallized in dichloromethane and methanol to afford the pure compound 7α,12α-dihydrocholane (12.8 g, 80% over two steps). Mp: 182-184° C.; $[\alpha]_D^{25}=-333.3$ (CHCl$_3$, c=0.84); IR (film) $V_{max}$=3380, 2919, 2857, 2360, 2341, 1653, 1450, 1376, 1192, 1085, 1027, 984, 909 cm$^{-1}$; $^1$H NMR (300 MHz, CDCl$_3$) δ=4.01 (brs, 1H), 3.85 (brs, 1H), 2.20-1.80 (m, 5H), 1.78-1.00 (series of multiplet, 23H), 0.98 (d, J=6.3 Hz, 3H), 0.90-0.85 (m, 6H), 0.70 (s, 3H) ppm; $^{13}$C NMR (125 MHz, CDCl$_3$ and CD$_3$OD): δ 72.8, 68.1, 47.0, 45.9, 42.8, 41.2, 39.1, 37.8, 37.1, 35.2, 34.5, 29.9, 27.7, 27.2, 27.2, 26.0, 22.8, 22.7, 20.7, 18.9, 16.9, 13.8, 11.9 ppm; HR-MS: calcd for $C_{24}H_{42}O_2Na^+$ [M+Na$^+$]: 385.3077. found 385.3057.

7α,12α-Di-(O-β-D-maltosyl)-cholane (A1)

A mixture of 7α,12α-dihydroxy-cholane (210 mg, 0.58 mmol), 1-thio-ethyl-hepta-o-benzoyl-β-D-maltose (2.1 g, 2.08 mmol) and 4 Å molecule sieves (800 mg) in dry CH$_2$Cl$_2$ (50 mL) was stirred at RT for 30 minutes. The reaction mixture was then cooled to −15° C., to which was added crystallized N-iodosuccinimide (500 mg, 2.22 mmol) and silver trifluorosulfonate (100 mg, 0.39 mmol). The reaction mixture was slowly warmed up to RT with stirring. The reaction was monitored by TLC. Upon completion, the reaction was quenched with triethylamine. The mixture was filtered and the filtrate was concentrated under vacuum.

The residue was submitted to column chromatography on silica gel to separate the crude mono- and di-glycosylation products. The mono-glycosylation products can be recovered for complete glycosylation. The combined di-glycosylation products were directly dissolved in methanol (30 mL), and to this solution was added sodium methoxide (300 mg) with stirring. The reaction was stirred at room temperature overnight.

The solvent was removed under vacuum and the residue was subjected to column chromatography on silica gel to give compound A1 (305 mg, 52%) as a solid. Mp: 188-190° C.; $[\alpha]_D^{25}$=95.0 (MeOH, c=1.00); IR (film) $V_{max}$=3351, 2920, 2361, 2340, 1646, 1375, 1146, 1073, 1019, 607 cm$^{-1}$; $^1$H NMR (500 MHz, CD3OD) δ=5.18 (d, J=4.0 Hz, 1H), 5.17 (d, J=4.0 Hz, 1H), 5.56 (s, 1H), 4.37 (d, J=8.0 Hz, 1H), 4.36 (d, J=8.0 Hz, 1H), 3.93-3.73 (m, 9H), 3.71-3.59 (m, 8H), 3.53-3.43 (m, 4H), 3.39-3.23 (m, 8H), 2.31-1.09 (m, 25H), 1.03 (d, J=6.5 Hz, 3H), 0.92 (s, 3H), 0.86 (t, J=7.0 Hz, 3H), 0.71 (s, 3H) ppm; $^{13}$C NMR (125 MHz, CD$_3$OD): 106.6, 102.8, 102.7, 100.9, 86.3, 81.7, 81.5, 78.1, 78.0, 76.6, 76.5, 75.2, 75.1, 75.0, 74.9, 74.7, 74.1, 71.5, 62.9, 62.8, 62.7, 62.6, 47.8, 47.0, 44.9, 43.3, 40.8, 39.6, 39.2, 37.7, 36.8, 31.2, 30.7, 29.3, 28.9, 28.2, 24.2, 24.1, 22.7, 20.3, 18.5, 15.0, 13.0 ppm; HR-MS: calcd for $C_{48}H_{82}O_{22}Na^+$ [M+Na$^+$]: 1033.5190. found 1033.5196.

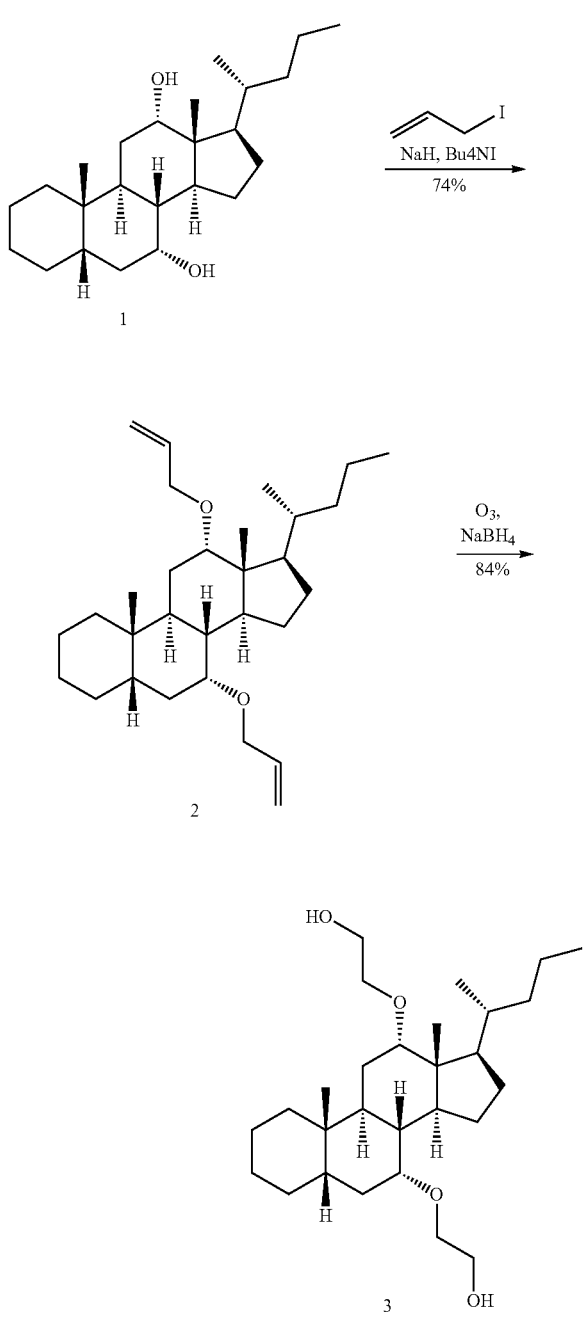

The facial amphiphiles A1 and A3 were both synthesized from the intermediate 1. Compounds A2 and A4 were synthesized from the intermediate 3.

7α,12α-Di-(2-propenyloxy)-cholane (2)

To a solution of dihydroxycholane 1 (4.0 g, 11.1 mmol) in 200 mL THF was added sodium hydride (4.42 g, 110.5 mmol) at 0° C. The reaction mixture was warmed up to room temperature and then stirred for 1 hour. Allyl iodide (9.23 g, 55.3 mmol) and tetrabutylammonium iodide (12.3 g, 33.2 mmol) were added to the reaction mixture which was then heated to reflux for overnight. The reaction was quenched with saturated NH₄Cl solution at room temperature and then extracted with EtOAc. The combined organic layers were washed with brine and then dried over anhydrous Na₂SO₄. The filtered organic portion was concentrated under vacuum to give the product 2 (3.6 g, 74%) which was directly used for the next steps.

were washed with brine and dried over Na₂SO₄. The filtered solvent was purified by column to afford 3 (3.1 g, 84%)

Data for compound 3: $^1$H NMR (300 MHz, CDCl₃) δ=3.80-3.55 (m, 6H), 3.76-3.70 (m, 1H), 3.34-3.14 (m, 3H), 2.25-1.0 (m, 28H), 0.92-0.86 (m, 9H), 0.68 (s, 3H) ppm; ESI-MS: calcd for $C_{28}H_{50}O_4Na^+$ [M+Na⁺]: 473. found 473.

Preparation of Compound A1:

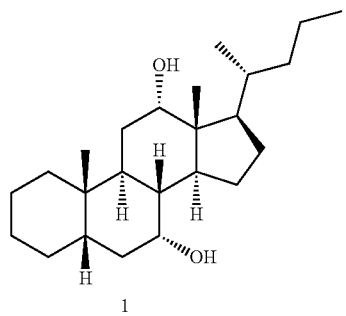
1

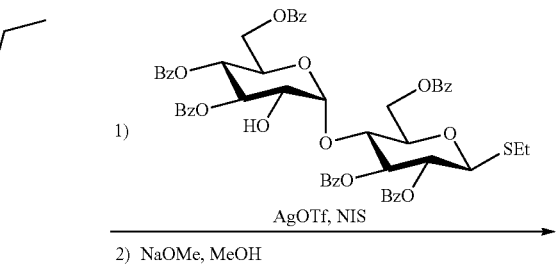
1)
2) NaOMe, MeOH

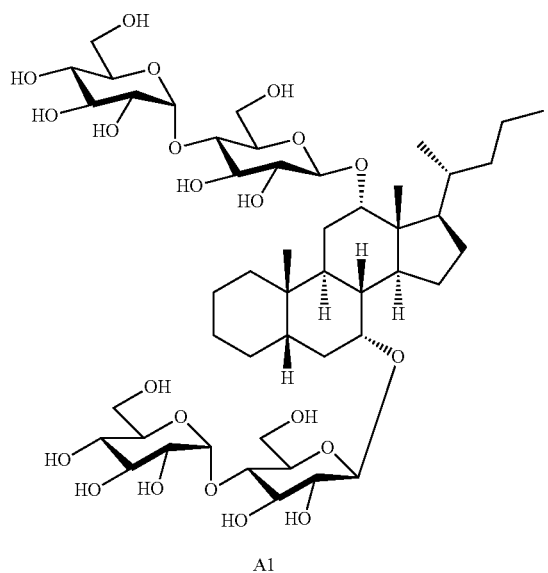
A1

Data for compound 2: $^1$H NMR (300 MHz, CDCl₃) δ=6.05-5.80 (m, 2H), 5.35-5.00 (m, 4H), 4.13-4.10 (m, 2H), 3.90-3.62 (m, 2H), 3.55 (brs, 1H), 3.31 (brs, 1H), 2.20-1.04 (m, 24H), 0.91-0.86 (m, 9H), 0.66 (s, 3H) ppm; $^{13}$C NMR (300 MHz, CDCl₃) δ=136.4, 115.4, 81.2, 75.6, 69.4, 69.3, 46.8, 46.5, 43.9, 42.9, 40.0, 38.5, 37.9, 35.8, 35.6, 29.3, 29.2, 28.3, 28.0, 27.9 ppm, ESI-MS: calcd for $C_{30}H_{50}O_2Na^+$ [M+Na⁺]: 465. found 465.

7α,12α-Di-(2-hydroxyethoxy)-cholane (3)

To a solution of the above residue (2) in a mixture of 200 mL CH₂Cl₂ and 100 mL methanol was bubbled ozone (−78° C.) until a blue color persisted. Excess ozone was removed with oxygen flow in a dry-ice/acetone bath for 15 minutes. Methyl sulfide (2.4 mL) was added. After 15 minutes, the mixture was treated with NaBH₄ (1.21 g, 32 mmol) in 5% NaOH aqueous solution (10 mL)/methanol (10 mL) and allowed to room temperature. The reaction was quenched with saturated NH₄Cl solution. The organic solution was evaporated under vacuum and the left aqueous solution was extracted with ethyl acetate. The combined organic layers 7α,12α-Di-(O-β-D-maltosyl)-cholane (A1) was prepared according to the procedure described above.

Preparation of Compound A3:

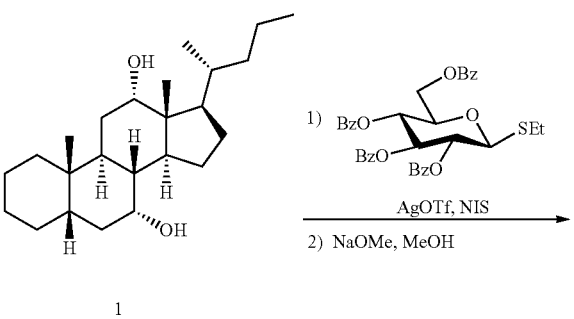
1
1)
2) NaOMe, MeOH

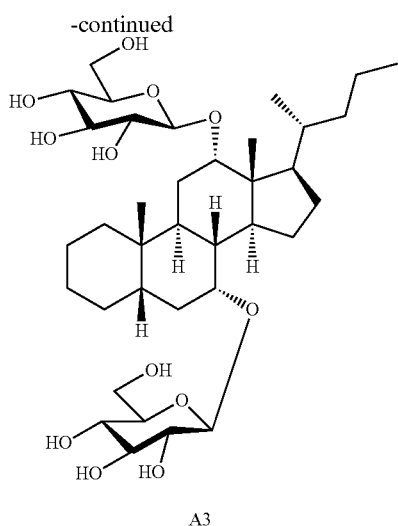

7α,12α-Di-(O-β-D-glucosyl)-cholane (A3)

A mixture of compound 1 (315 mg, 0.87 mmol), 1-thio-ethyl-tetra-o-benzoyl-β-D-glucoside (2.22 g, 3.48 mmol) and 4 Å molecule sieves (500 mg) in dry $CH_2Cl_2$ (100 mL) was stirred at room temperature for 30 minutes. The reaction mixture was then cooled to −15° C., to which was added crystallized N-iodosuccinimide (783 mg, 2.22 mmol) and silver trifluorosulfonate (148 mg, 0.66 mmol). The reaction mixture was slowly warmed up to room temperature with stirring for 3 hours. The reaction was quenched with triethylamine. The mixture was filtered and the filtrate was concentrated under vacuum. The residue was submitted to column chromatography on silica gel to purify the di-glycosylation product, which was then dissolved in methanol (30 mL) and to this solution was added sodium methoxide (1000 mg) with stirring. The reaction was stirred at room temperature for overnight. The solvent was removed under vacuum and the residue was subjected to column chromatography on silica gel to give compound A3 (209 mg, 35% over 2 steps) $^1$H NMR (500 MHz, CD3OD) δ=4.44 (d, J=8.0 Hz, 1H), 4.34 (d, J=8.0 Hz, 1H), 4.05-3.60 (m, 8H), 3.42-3.25 (m, 6H), 2.31-1.09 (m, 25H), 1.10 (d, J=6.5 Hz, 3H), 0.96 (s, 3H), 0.94 (t, J=7.0 Hz, 3H), 0.79 (s, 3H) ppm; $^{13}$C NMR (125 MHz, $CD_3OD$): 105.7, 99.8, 85.2, 77.4, 77.2, 76.7, 76.6, 74.6, 74.4, 73.7, 71.4, 71.2, 62.6, 62.3, 46.9, 46.07, 43.9, 42.3, 39.8, 38.6, 38.1, 36.6, 35.8, 30.2, 29.6, 28.3, 28.0, 27.3, 23.1, 23.1, 21.6, 19.3, 17.5, 14.0, 12.0 ppm.

Preparation of Compound A2:

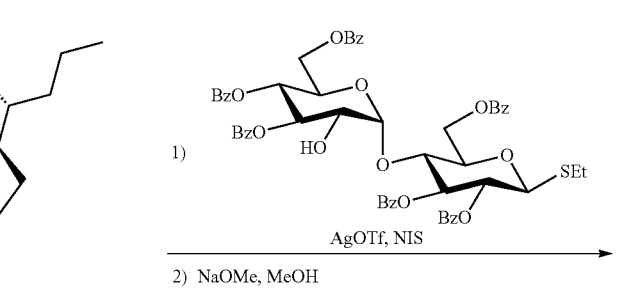

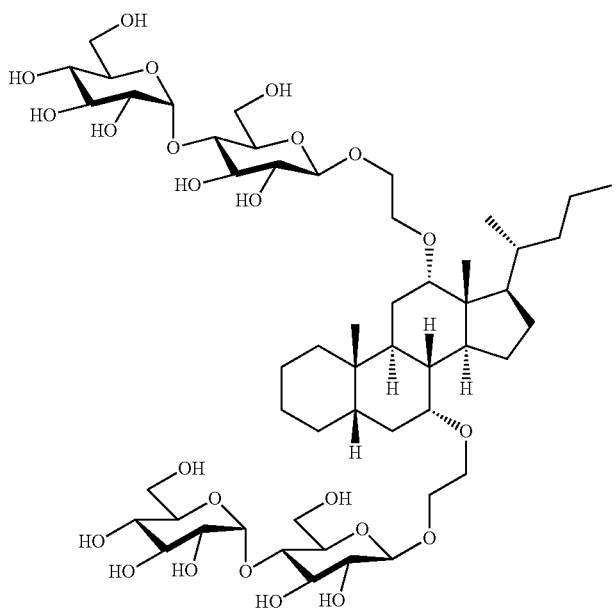

7α,12α-Di-((O-β-D-maltosyl)-2-hydroxyethoxy)-cholane (A2)

The procedure is analogous to the preparation of A1, using compound 3 as starting material (72% over two steps).

Data for compound A2: $^1$H NMR (400 MHz, MeOD) δ=5.16 (d, J=3.6 Hz, 1H), 5.15 (d, J=3.6 Hz, 1H), 4.41 (d, J=8.0 Hz, 2H), 4.03-3.23 (m, 39H), 2.28-1.00 (m, 24H), 0.98 (d, J=14.4 Hz, 3H), 0.95 (s, 3H), 0.88 (t, J=7.2 Hz, 3H), 0.70 (s, 3H) ppm. $^{13}$C NMR (100 MHz, MeOD): δ=104.2, 104.1, 102.9, 102.8, 83.1, 81.3, 81.2, 77.7, 76.5, 74.7, 74.1, 71.4, 69.9, 69.6, 68.7, 62.7, 47.4, 45.1, 44.1, 40.9, 39.6, 38.7, 36.9, 36.4, 30.4, 29.4, 28.7, 24.3, 24.3, 24.2, 22.8, 20.4, 18.6, 15.1, 13.1 ppm. HR-ESI: $C_{52}H_{90}NaO_{24}^+$: 1121.5714. found: 1121.5696, IR=3374, 2934, 1107 cm$^{-1}$.

Preparation of Compound A4:

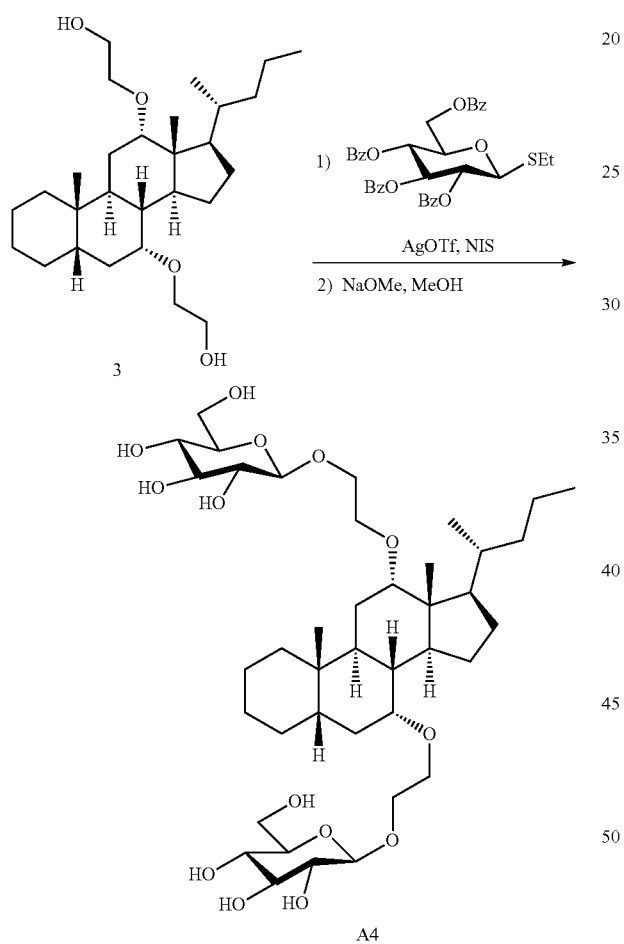

7α,12α-Di-((O-D-glucosyl)-2-hydroxyethoxy)-cholane (A4)

The procedure is analogous to the preparation of A3, using compound 3 as starting material (49% over two steps).

Data for compound A4: $^1$H NMR (400 MHz, MeOD) δ=4.37 (d, J=8.0 Hz, 1H), 4.37 (d, J=7.6 Hz, 1H), 4.07-3.93 (m, 2H), 3.89-3.65 (m, 10H), 3.57 (s, 1H), 3.48-3.17 (m, 12H), 2.26-1.03 (m, 24H), 0.96 (d, J=6.4 Hz, 3H), 0.93 (s, 3H), 0.89 (t, J=6.8 Hz, 3H), 0.71 (s, 3H) ppm. $^{13}$C NMR (100 MHz, MeOD): δ=104.4, 104.2, 83.3, 78.0, 77.9, 77.9, 75.2, 71.6, 69.9, 69.6, 68.9, 68.8, 62.8, 47.9, 47.5, 45.1, 44.1, 40.9, 39.6, 36.9, 36.4, 30.4, 30.0, 29.4, 28.9, 24.3, 24.3, 24.2, 20.4, 18.6, 15.0, 13.1 ppm HR-ESI: $C_{40}H_{71}O_{14}^+$: 775.4838. found: 775.4843, IR=3379, 2927, 2866, 1076, 1033, 667 cm$^{-1}$.

Preparation of Compound A5:

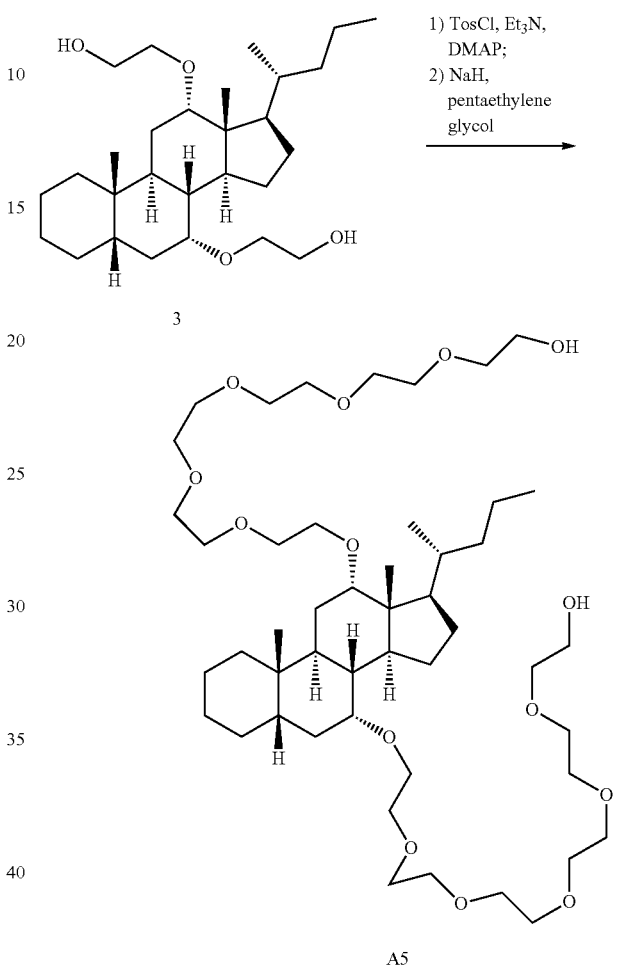

7α,12α-Di-(hexaoxyethylene)-cholane (A5)

To a solution of compound 3 (2.0 g, 4.44 mmol) in dichloromethane (45 mL) in was added triethyl amine (1.36 g, 13.32 mmol), p-toluenesulfonyl chloride (2.10 g 11.1 mmol) and 4-(dimethylamino)pyridine (53 mg, 0.45 mmol) at 0° C. The reaction mixture was warmed to room temperature and stirred for 2 hours. Then the reaction was quenched with saturated NH$_4$Cl solution and the aqueous layer was extracted with EtOAc. The combined organic layers were washed with brine and dried over Na$_2$SO$_4$. The filtrate was concentrated under vacuum, and the crude residue (3.18 g) was used directly for the next step without further purification Sodium hydride (60% dispersion in mineral oil, 1.78 g, 44.5 mmol) was added slowly to a solution of pentaethylene glycol (10.5 g, 44.5 mmol) in anhydrous THF (50 mL) at 0° C. Then the solution was heated to reflux for 30 minutes, to which a solution of above tosylate in anhydrous THF (20 mL) was added and the reaction mixture was refluxed for overnight. After cooled to room temperature, the reaction was quenched with saturated NH$_4$Cl aqueous solution. The aqueous layer was extracted with EtOAc and the combined organic layers were washed with brine and dried over $Na_2SO_4$. The filtered solvent was evaporated and the residue was purified by column to afford A5 (3.1 g, 79% over two steps)

Data for A5: $^1$H NMR (300 MHz, $CDCl_3$) δ=3.71-3.54 (m, 44H), 3.46 (brs, 1H), 3.25 (brs, 1H), 2.96 (brs, 2H), 2.20-1.02 (m, 23H), 0.88-0.83 (m, 9H), 0.62 (s, 3H) ppm MS: calcd for $C_{48}H_{90}O_{14}Na^+$ [M+Na$^+$]: 913.6. found 913.5.

Preparation of Compound A6:

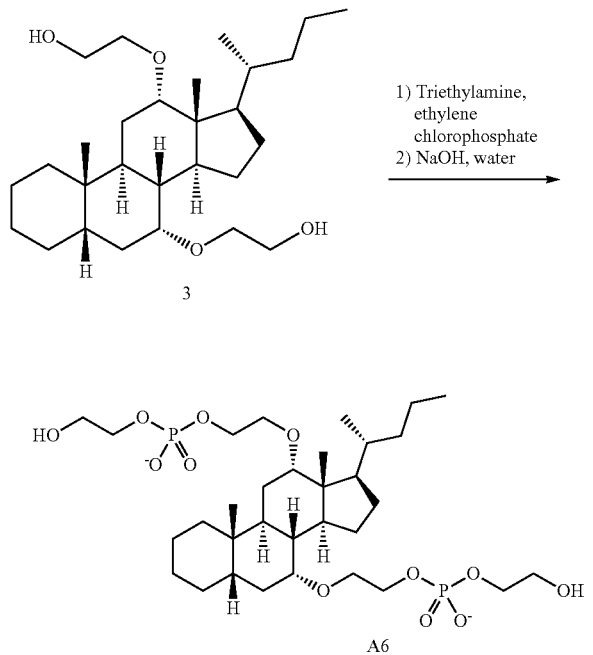

7α,12α-Di-((2-hydroxyethoxy)phosphinyl)-cholane (A6)

To a solution of compound 3 (180 mg, 0.40 mmol) and triethylamine (161 mg, 1.60 mmol) in anhydrous toluene (15 mL) was added dropwise ethylene chlorophosphate (177 mg 1.2 mmol) at 0° C. The reaction was slowly warmed up to room temperature and stirred for another 1 hour. The reaction mixture was filtered and the solid was washed with anhydrous toluene (10 ml). The filtrate was concentrated under vacuum and the crude residue (230 mg) was used directly without further purification.

To a solution of above residue in 1,4-dioxane was added 5 M sodium hydroxide aqueous solution (5 mL). The reaction mixture was heated to 55° C. for 3 hours. The mixture was titrated with 1N HCl aqueous solution to pH=2-3. The mixture was evaporated to remove all solvent and the residue was subjected to column chromatography on silica gel to give A6 (125 mg, 45% over 2 steps)

Data for A6: $^1$H NMR (500 MHz, MeOD) δ=4.11-4.06 (m, 7H), 3.80-3.66 (m, 6H), 3.43-3.38 (brs, 7H), 2.34-2.20 (m, 3H), 2.20-1.02 (m, 23H), 1.03 (d, J=6.5 Hz, 3H), 1.01 (s, 3H), 0.97 (t, J=7.0 Hz, 3H), 0.74 (s, 3H) ppm.

Preparation of Compound A7:

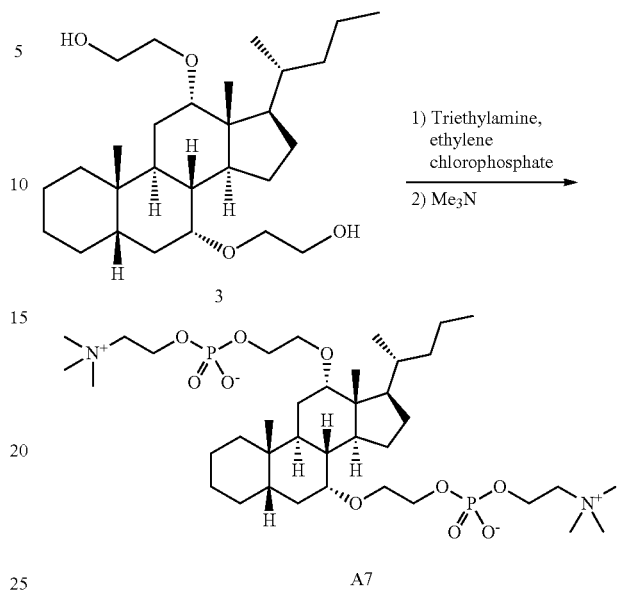

A7: To a solution of compound 3 (2.5 g, 5.55 mmol) and triethylamine (2.24 g, 22.2 mmol) in anhydrous toluene (55 mL) was added ethylene chlorophosphate (2.05 g 13.8 mmol) at 0° C. The reaction was slowly warmed up to room temperature and stirred for 1 hour. The reaction mixture was filtered and the solid was washed with anhydrous toluene (50 ml). The filtrate was concentrated under vacuum and the crude residue (2.7 g) was used directly without further purification.

The above residue was dissolved in anhydrous acetonitrile (100 mL) in a pressure bottle, and the solution was cooled down using a dry ice/acetone bath before trimethylamine (10 mL) was introduced. The reaction was left to proceed in 70° C. for 24 hours and diluted with methanol. The mixture was concentrated under vacuum and the residue was subjected to column chromatography on silica gel to give A7 (2.79 g, 64% over 2 steps).

Data for A7: $^1$H NMR (400 MHz, MeOD) δ=4.28 (m, 4H), 3.79-3.69 (m, 2H), 3.68-3.63 (m, 4H), 3.56 (s, 1H), 3.49-3.39 (m, 1H), 3.37-3.31 (m, 4H), 3.30-3.27 (m, 4H), 3.24 (s, 9H), 3.23 (s, 9H), 2.22-1.01 (m, 23H), 0.95 (d, J=6.4 Hz, 3H), 0.90 (s, 3H), 0.86 (t, J=6.8 Hz, 3H), 0.69 (s, 3H) ppm. $^{13}$C NMR (100 MHz, MeOD): δ=81.8, 76.7, 68.0, 66.3, 66.3, 65.4, 65.3, 65.1, 59.3, 53.7, 53.7, 53.6, 46.4, 43.9, 43.1, 39.8, 38.5, 37.5, 29.1, 28.8, 28.3, 27.7, 27.6, 23.1, 21.6, 13.7, 11.9 ppm HR-ESI: $C_{38}H_{74}N_2NaO_{10}P_2^+$: 803.4711. found: 803.4730, IR=3356, 2927, 2866, 1473, 1074, 1033, 670 cm$^{-1}$.

Preparation of Compound A8:

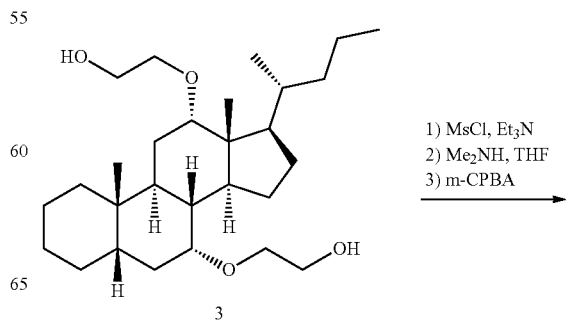

49

-continued

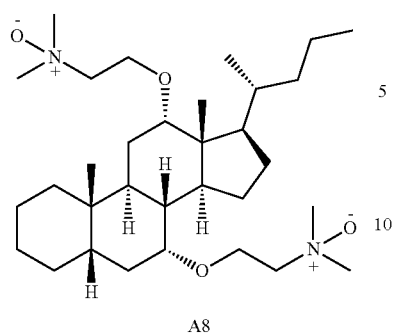

A8

Compound A8:

To a solution of compound 3 (1.0 g, 2.22 mmol) and triethylamine (1.01 g, 9.99 mmol) in anhydrous dichloromethane (30 mL) was added methylsulfonyl chloride (759 mg, 6.66 mmol) at 0° C. The reaction was slowly warmed up to room temperature and stirred for 30 minutes. The reaction mixture was quenched with saturated $NH_4Cl$ aqueous solution and the aqueous layer was extracted with dichloromethane. The combined organic layers were washed with brine, dried over anhydrous $Na_2SO_4$, filtered, and concentrated under vacuum. The residue (1.3 g) was used directly without further purification.

To a solution of above residue in THF (20 mL) was added dimethylamine (40% in water, 10 mL). The reaction mixture was heated to reflux for overnight. The mixture was evaporated to remove organic solvent and the aqueous solution was extracted with dichloromethane. The combined organic layers were washed with brine, dried over anhydrous $Na_2SO_4$, filtered, and concentrated under vacuum. The residue (950 mg) was used directly without further purification.

To a solution of above residue in dichloromethane was added 3-chloroperoxybenzoic acid (balance 3-chlorobenzoic acid and water 70-75%, 1.56 g) at 0° C. The reaction mixture was warmed up to room temperature and stirred for another 30 minutes. The reaction was quenched with 10% $Na_2S_2O_3$ aqueous solution and the aqueous layer was extracted with dichloromethane. The combined organic layers were washed with brine, dried over anhydrous $Na_2SO_4$, filtered, and concentrated under vacuum. The residue was subjected to column chromatography on silica gel to give A8 (667 mg, 56% over 2 steps).

Data for A8: $^1H$ NMR (400 MHz, MeOD) δ=4.10-4.00 (m, 1H), 3.92-3.87 (m, 1H), 3.67-3.28 (m, 8H), 3.17 (s, 3H), 3.15 (s, 3H), 3.13 (s, 3H), 3.11 (s, 3H), 2.11-1.47 (m, 12H), 1.40-0.92 (m, 14H), 0.88 (d, J=6.0 Hz, 3H), 0.87 (s, 3H), 0.79 (t, J=6.8 Hz, 3H), 0.65 (s, 3H) ppm. $^{13}C$ NMR (100 MHz, MeOD): δ=83.5, 79.6, 78.4, 72.2, 71.9, 63.5, 60.2, 60.0, 59.3, 59.1, 47.4, 44.9, 40.8, 39.6, 38.6, 36.9, 36.6, 30.8, 29.7, 29.4, 28.8, 28.6, 24.4, 24.2, 23.8, 23.0, 20.4, 18.7, 15.0, 13.1 ppm. HR-ESI: $C_{32}H_{61}N_2O_4^+$: 537.4626. found: 537.4625. IR: 3395, 2935, 2865, 1653, 1458, 1032, 738 $cm^{-1}$.

50

Preparation of Compounds with Linkers:

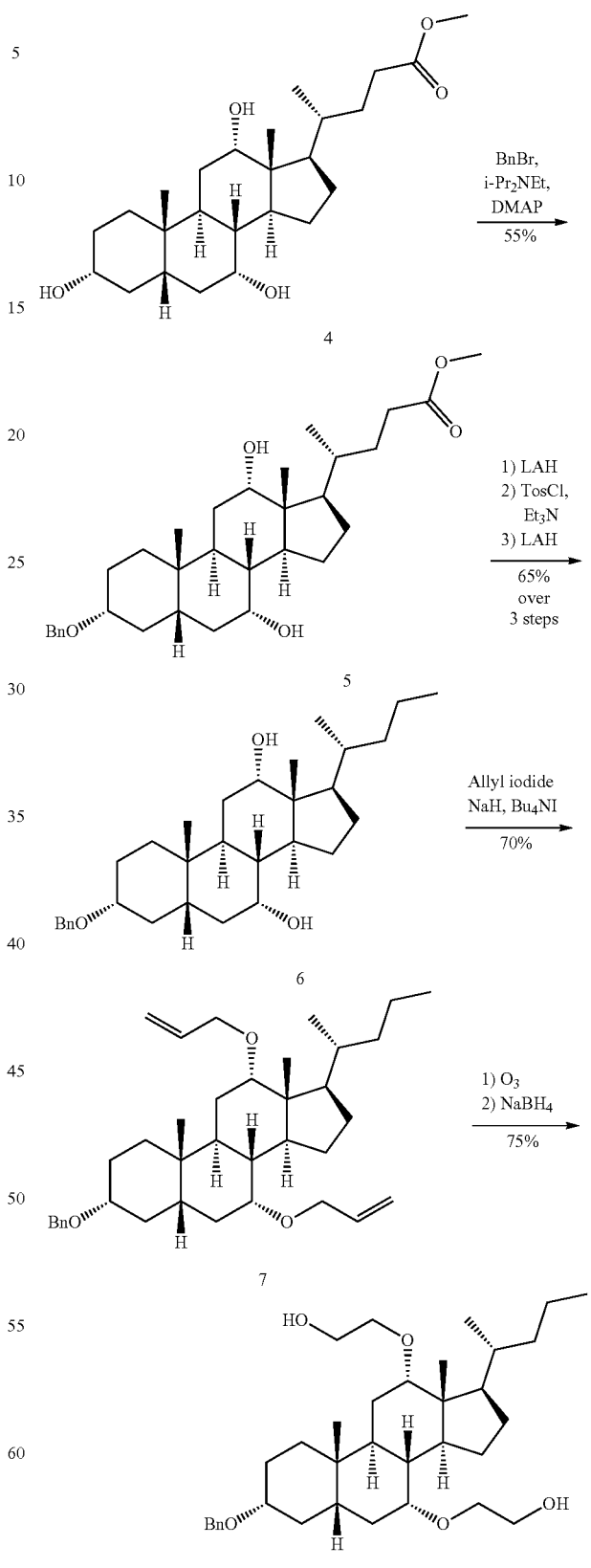

Compound 5:

To a solution of methyl cholate (4) (10 g, 23.7 mmol) in 80 mL diisopropylethyl amine was added benzyl bromide (6.05 g, 35.6 mmol). The reaction mixture was heated to 100° C. and stirred for overnight. The reaction mixture was diluted in water (800 mL) and EtOAc (400 mL). The aqueous layer was extracted with EtOAc and the combined organic layers were washed with water, 1N aqueous HCl solution and brine, and dried over $Na_2SO_4$. The filtrate was concentrated under vacuum and purified over column chromatography on silica to afford 5 (6.82 g, 13.3 mmol).

Data for Compound 5: NMR (400 MHz, CDCl3) δ=7.33-7.26 (m, 5H), 4.55 (dd, J=12, 14.4 Hz, 2H), 3.96 (s, 1H), 3.79 (s, 1H), 3.66 (s, 3H), 3.26-3.19 (m, 1H), 2.41-1.09 (m, 28H), 0.97 (d, J=8 Hz, 3H), 0.88 (s, 3H), 0.68 (s, 3H) ppm.

To a solution of $LiAlH_4$ (358 mg, 9.7 mmol) in dry THF (100 mL) was added dropwise a solution of compound 5 (4.25 g, 8.3 mmol) in dry THF (50 mL) at 0° C. The reaction mixture was heated to reflux for overnight. Then the reaction was quenched with 1N aqueous HCl solution at room temperature. The aqueous layer was extracted with EtOAc and the combined organic layers were washed with brine and dried over $Na_2SO_4$. The filtered solution was concentrated under vacuum, and the residue was dissolved in 100 mL dry $CH_2Cl_2$ for the next step.

To the above solution was added triethyl amine (1.35 g, 13.4 mmol) and p-toluenesulfonyl chloride (1.59 g 8.3 mmol) at 0° C. The reaction mixture was warmed to room temperature and stirred for 2 hours. Then the reaction was quenched with saturated $NH_4Cl$ solution and the aqueous layer was extracted with EtOAc. The combined organic layers were washed with brine and dried over $Na_2SO_4$. The filtrate was concentrated under vacuum, and the residue (4.84 g) was used directly for the next step without further purification.

The above residue was dissolved in dry THF (50 mL) and added slowly to a solution of $LiAlH_4$ (300 mg, 7.89 mmol) in THF at 0° C. The reaction mixture was heated to reflux for overnight. Then the reaction was quenched with 1N aqueous HCl solution at room temperature. The aqueous layer was extracted with EtOAc and the combined organic layers were washed with brine and dried over $Na_2SO_4$. The filtered organic portion was concentrated under vacuum to give compound 6 (2.53 g, 65% over 3 steps) which was used directly for the next step without purification.

Data of compound 6: NMR (500 MHz, CDCl3) δ=7.42-7.31 (m, 5H), 4.63 (s, 2H), 4.60 (s, 1H), 3.83 (s, 1H), 3.34-3.27 (m, 1H), 2.40-1.12 (m, 26H), 1.48 (d, J=6.5 Hz, 3H), 0.97-0.94 (m, 6H), 0.76 (s, 3H) ppm.

Compound 7:

To a solution of 6 (4.0 g, 8.54 mmol) in 100 mL THF was added sodium hydride (1.5 g, 37.5 mmol) at 0° C. The reaction mixture was warmed to room temperature and then stirred for 1 hour. Allyl iodide (3.08 g, 18.4 mmol) and tetrabutylammonium iodide (4.1 g, 11.0 mmol) were added to the reaction mixture and the reaction was heated to reflux for overnight. The reaction was quenched with saturated $NH_4Cl$ solution and then extracted with EtOAc. The combined organic layers were washed with brine and then dried over anhydrous $Na_2SO_4$. The filtered organic portion was concentrated under vacuum. The residue was purified over silica gel column to give 7 (3.3 g, 70%)

Data of Compound 7: NMR (300 MHz, CDCl3) δ=7.34-7.23 (m, 5H), 6.01-5.85 (m, 2H), 5.33-5.06 (m, 4H), 4.54 (dd, J=12.3, 13.8 Hz, 2H), 4.11-4.04 (m, 2H), 3.81-3.68 (m, 2H), 3.54 (s, 1H), 3.32 (d, J=3.0 Hz, 1H), 3.24-3.14 (m, 1H), 2.38-0.96 (m, 24H), 0.91-0.83 (m, 9H), 0.65 (s, 3H) ppm.

Compound 8: To a solution of 7 (3.3 g, 6.0 mmol) in 100 mL $CH_2Cl_2$ and 50 mL methanol was bubbled ozone (−78° C.) through until a blue color persisted. Excess ozone was removed with oxygen flow in a dry-ice/acetone bath for 15 minutes. Then the mixture was treated with $NaBH_4$ (1.21 g, 32 mmol) in 5% aqueous NaOH solution (10 mL) and methanol (10 mL) and allowed to room temperature. The reaction was quenched with saturated $NH_4Cl$ solution. The organic solution was evaporated under vacuum and the left aqueous solution was extracted with ethyl acetate. The combined organic layers were washed with brine and dried over $Na_2SO_4$. The filtered solvent was purified by column to afford 8 (2.5 g, 75%)

Data of Compound 8: NMR (400 MHz, CDCl3) δ=7.27-7.20 (m, 5H), 4.74 (s, 2H), 3.77-3.56 (m, 6H), 3.56 (s, 1H), 3.27-3.13 (m, 4H), 2.21-0.91 (m, 26H), 0.85 (d, J=6.8 Hz, 3H), 0.83 (s, 3H), 0.79 (t, J=6.8 Hz, 3H), 0.61 (s, 3H) ppm.

Preparation of Compound B1:

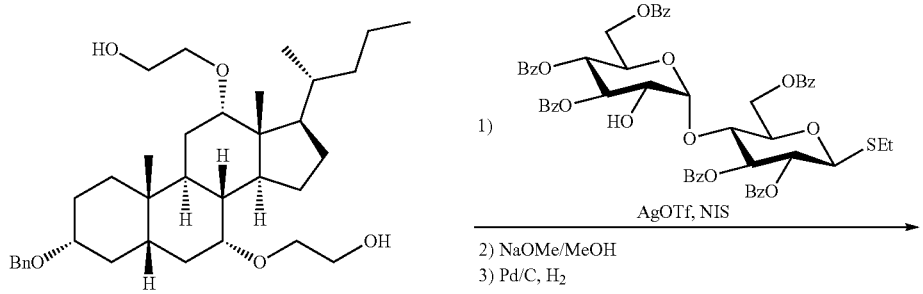

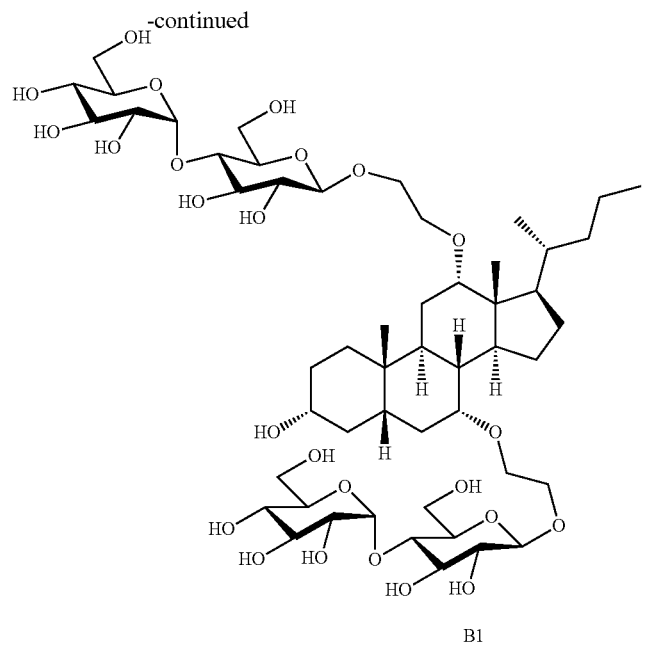

B1

3α-hydroxyl-7α,12α-Di-((O-β-D-maltosyl)-2-hydroxyethoxy)-cholane (B1)

The procedure for the first two steps is analogous to the preparation of A1, using compound 8 as starting material. The glycosylated intermediate was dissolved in MeOH (100 mL) and the solution was purged with hydrogen. 10% Pd on activated carbon (100 mg) was added to the mixture, and the reaction was stirred under hydrogen for overnight. The mixture was filtered and the filtrate was evaporated, and the residue was subjected to column chromatography on silica gel to give B1 (702 mg, 50% over 3 steps)

Data for B1: $^1$H NMR (400 MHz, MeOD) δ=5.16 (d, J=2.8 Hz, 2H), 4.48 (d, J=8.0 Hz, 1H), 4.39 (d, J=7.6 Hz, 1H), 4.06-3.20 (m, 45H), 2.35-1.08 (m, 25H), 0.94 (d, J=6.8 Hz, 3H), 0.91 (s, 3H), 0.87 (t, J=7.2 Hz, 3H), 0.69 (s, 3H) ppm. $^{13}$C NMR (100 MHz, MeOD): δ=104.1, 103.9, 103.0, 102.9, 83.1, 81.4, 77.7, 76.5, 75.1, 74.7, 74.1, 73.0, 71.5, 69.9, 69.5, 69.4, 68.8, 62.8, 62.2, 48.4, 47.9, 47.4, 44.2, 43.4, 41.0, 39.6, 36.9, 35.6, 31.5, 29.8, 29.5, 28.7, 24.2, 23.4, 20.6, 18.6, 15.0, 13.0 ppm HR-ESI: $C_{52}H_{91}O_{25}^+$: 1114.5771. found: 1115.5834, IR=3371, 2928, 2866, 2359, 1372, 1075, 1035 cm$^{-1}$.

Preparation of Compound B2:

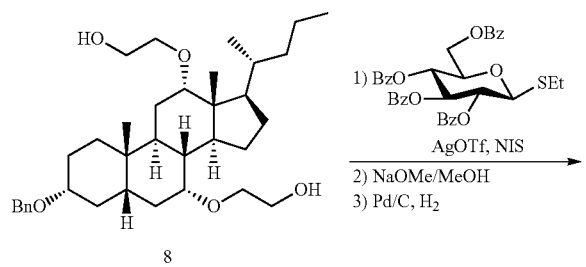

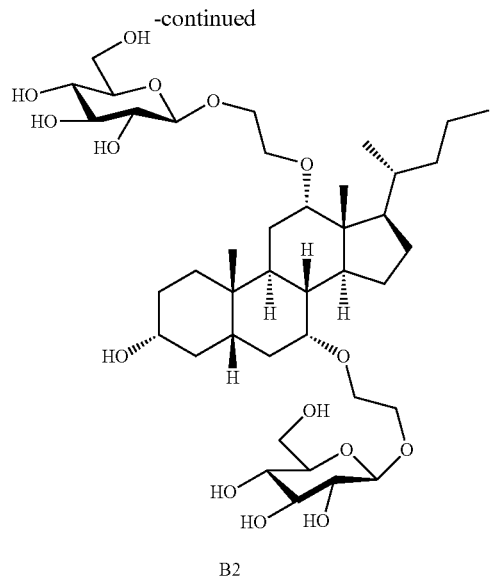

B2

3α-hydroxyl-7α,12α-Di-((O-D-glucosyl)-2-hydroxyethoxy)-cholane (B2)

The procedure for the first two steps is analogous to the preparation of A3, using compound 8 as starting material. The benzyl protection group was removed using a procedure similar to the last step in the preparation of B1. Compound B2 was obtained in 45% yield over 3 steps.

Data for B2: $^1$H NMR (400 MHz, MeOD) δ=4.44 (d, J=7.6 Hz, 1H), 4.36 (d, J=7.6 Hz, 1H), 4.02-3.98 (m, 2H), 3.90-3.65 (m, 8H), 3.55 (s, 1H), 3.45-3.28 (m, 12H), 3.22 (t, J=8.0 Hz, 2H), 2.33-1.01 (m, 24H), 0.95 (d, J=6.4 Hz, 3H), 0.92 (s, 3H), 0.88 (t, J=6.8 Hz, 3H), 0.70 (s, 3H) ppm. $^{13}$C NMR (100 MHz, MeOD): δ=103.0, 102.9, 81.9, 76.8, 76.7, 76.6, 74.0, 74.9, 71.7, 70.5, 68.6, 68.3, 68.1, 67.6, 61.6, 61.5, 43.0, 42.2, 39.7, 38.4, 35.7, 34.4, 28.3, 22.1, 19.1, 17.4, 13.8, 11.8 ppm. HR- ESI: $C_{40}H_{71}O_5^+$: 791.4787. found: 791.4771, IR=3325, 2927, 2860, 2485, 2217, 2071, 1637, 1448, 1371, 1162, 1074, 978 cm$^{-1}$.

Preparation of Compound B3:

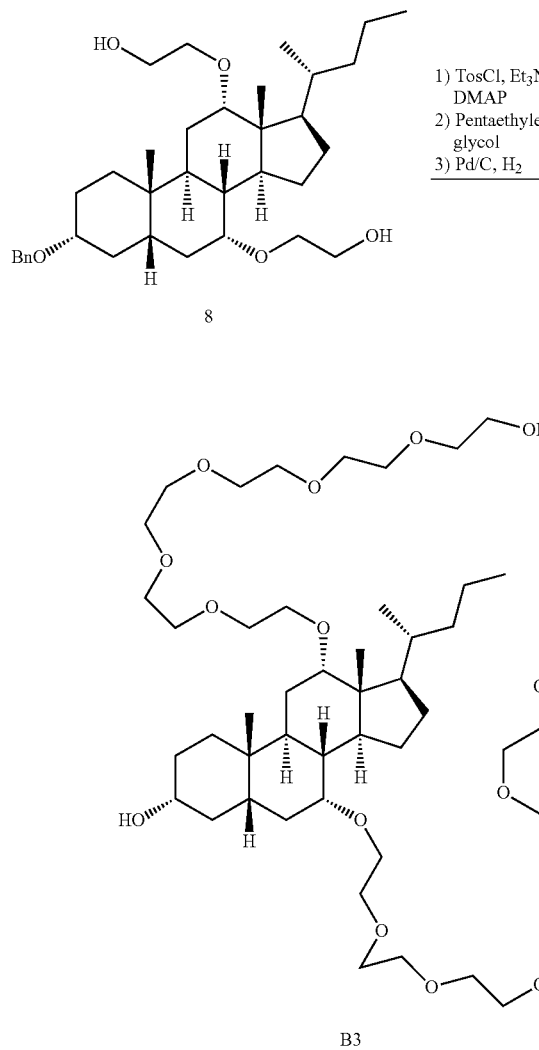

B3:

The procedure for the first two steps is analogous to the preparation of A5, using compound 8 as starting material. Benzyl group was finally removed using a procedure similar to the last step in the preparation of B1. Compound B3 was obtained in 87% yield over 3 steps.

Data for B3: $^1$H NMR (400 MHz, MeOD) δ=3.72-3.61 (m, 46H), 3.58-3.556 (m, 4H), 3.44-3.30 (m, 3H), 2.27-1.05 (m, 24H), 0.98 (d, J=7.2 Hz, 3H), 0.93 (s, 3H), 0.89 (t, J=6.8 Hz, 3H) ppm. $^{13}$C NMR (100 MHz, MeOD): δ=82.7, 77.7, 73.7, 72.8, 72.0, 71.8, 71.7, 71.6, 71.5, 71.4, 69.1, 62.2, 47.9, 47.4, 44.0, 43.3, 41.0, 39.7, 39.3, 36.9, 36.4, 35.7, 31.6, 29.7, 29.3, 28.8, 24.2, 24.1, 23.4, 20.3, 18.5, 15.0, 13.0 ppm. HR-ESI: $C_{48}H_{90}O_{15}Na^+$: 929.6172. found: 929.6183, IR=3420, 2964, 2495, 2072, 1467, 1349, 1296, 1120, 1097, 960 cm$^{-1}$.

Preparation of Compound B4:

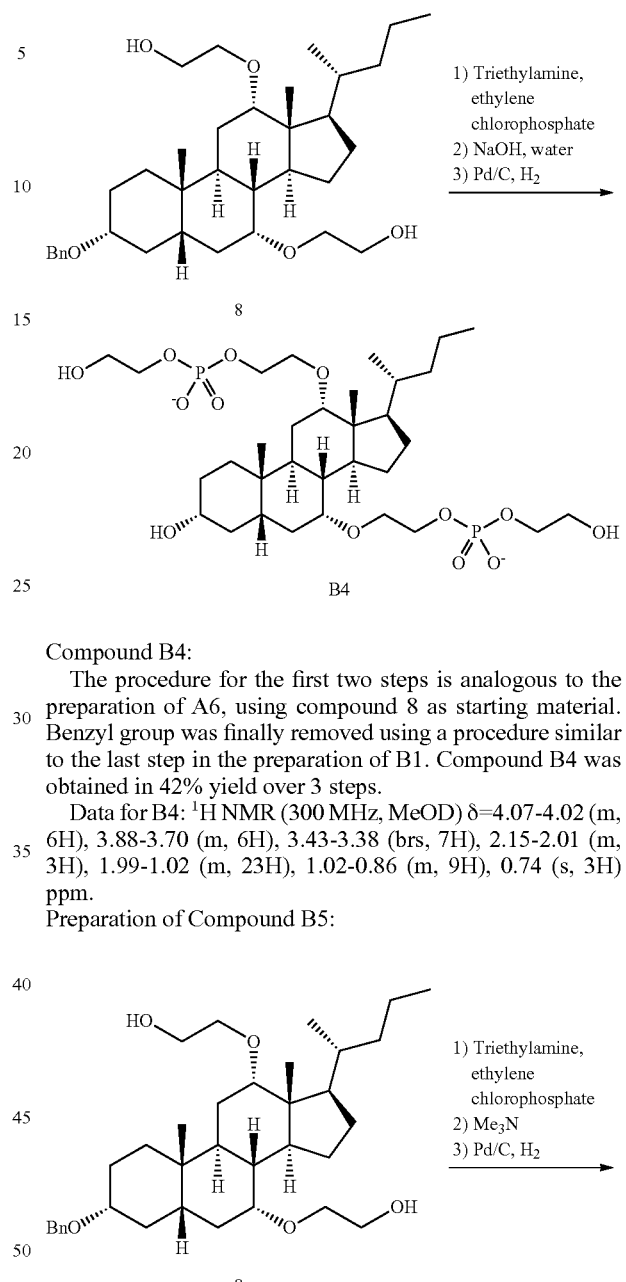

Compound B4:

The procedure for the first two steps is analogous to the preparation of A6, using compound 8 as starting material. Benzyl group was finally removed using a procedure similar to the last step in the preparation of B1. Compound B4 was obtained in 42% yield over 3 steps.

Data for B4: $^1$H NMR (300 MHz, MeOD) δ=4.07-4.02 (m, 6H), 3.88-3.70 (m, 6H), 3.43-3.38 (brs, 7H), 2.15-2.01 (m, 3H), 1.99-1.02 (m, 23H), 1.02-0.86 (m, 9H), 0.74 (s, 3H) ppm.

Preparation of Compound B5:

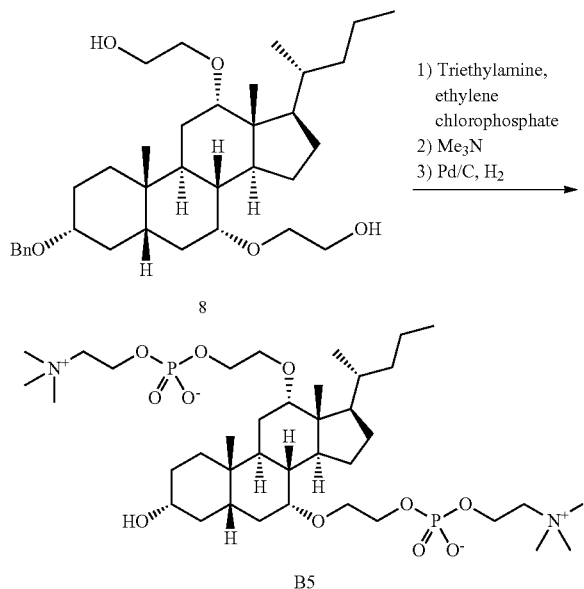

B5:

The procedure for the first two steps is analogous to the preparation of A7, using compound 8 as starting material. Benzyl group was finally removed using a procedure similar to the last step in the preparation of B1. Compound B5 was purified by reverse-phase HPLC (65% yield over 3 steps).

Data for B5: $^1$H NMR (400 MHz, MeOD) δ=4.29 (s, 4H), 3.98-3.92 (m, 4H), 3.72-3.61 (m, 6H), 3.40-3.30 (m, 4H), 3.18 (s, 9H), 3.17 (s, 9H), 2.22-0.96 (m, 24H), 0.91 (d, J=7.6 Hz, 3H), 0.85 (s, 3H), 0.80 (t, J=6.8 Hz, 3H), 0.64 (s, 3H) ppm. $^{13}$C NMR (100 MHz, MeOD): δ=82.6, 77.6, 72.9, 69.2, 69.1, 68.8, 67.4, 37.1, 67.0, 66.9, 66.8, 60.9, 60.9, 54.9, 54.8, 44.2, 43.4, 40.9, 39.7, 39.6, 36.9, 36.5, 31.5, 29.4, 28.9, 24.1, 23.3, 20.6, 18.6, 14.9, 13.1 ppm. HR-ESI: $C_{38}H_{75}N_2O_{11}P_2^+$: 797.4841. found: 797.4860, IR=3322, 2930, 2867, 2481, 2221, 2071, 1688, 1471, 1377, 1230, 1085, 1059 cm$^{-1}$.

Preparation of 3α,7α,12α-trihydroxyl-cholestane

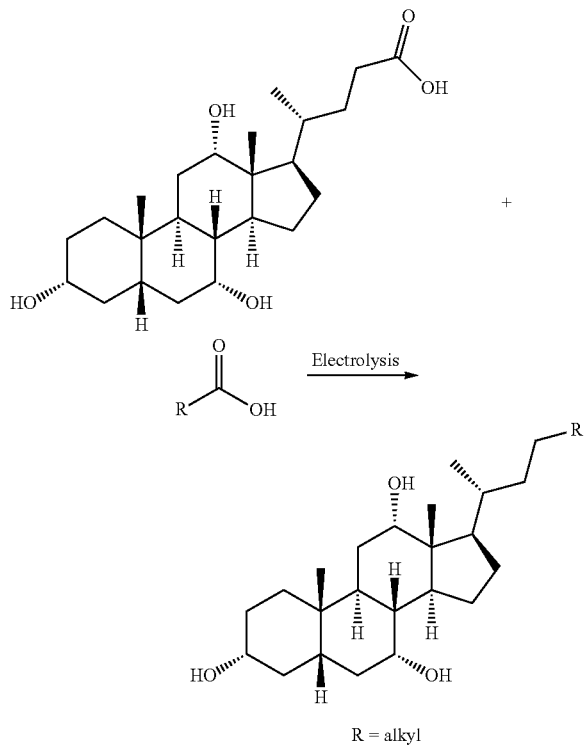

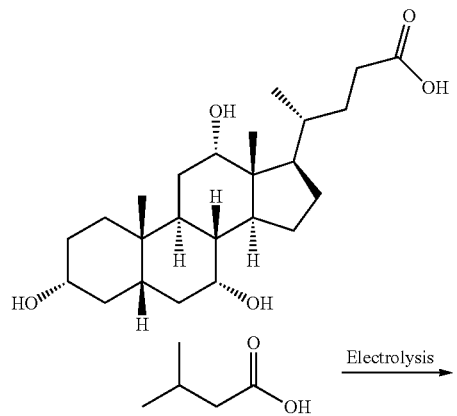

Electrolysis

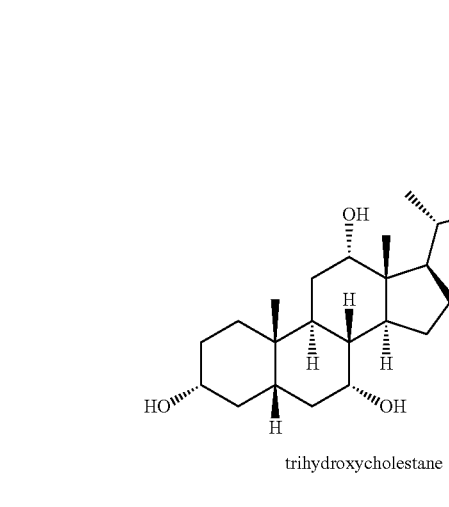

3α,7α,12α-trihydroxyl-cholestane

The product was synthesized by the electrochemical oxidative decarboxylation of carboxylic acids (Kolbe electrolysis) according to a literature procedure (Bergström, S. and Krabisch, L., Acta Chem. Scand. 1957, 11, 1067). To a solution of cholic acid (10 g, 24.5 mmol) and isovaleric acid (70 mL, 644 mmol) in methanol (400 mL) was added sodium methoxide (2.5 g). The solution was placed in a beaker surrounded by ice. The electrolysis was run for 24 hours with 1.0 A between platinum electrodes. After work up, the product was crystallized from acetone (6.2 g, 60%).

R = alkyl

Other 3α,7α,12α-trihydroxyl-cholane compounds with different terminal alkyl chains were prepared similarly through the electrolysis reaction of cholic acid and the other alkyl carboxylic acid.

Preparation of B7:

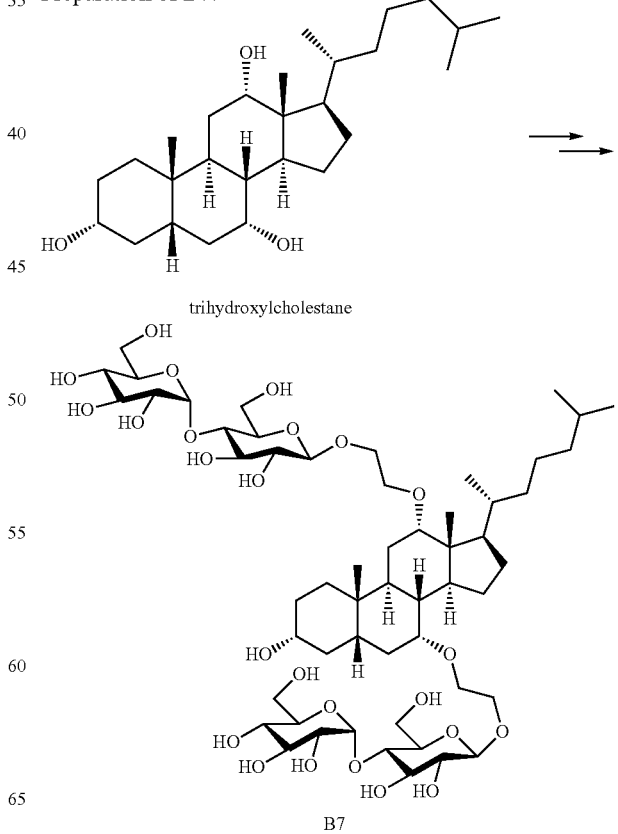

trihydroxylcholestane

B7

B7 was prepared by a procedure analogous to the preparation of B1, using trihydroxycholestane as starting material.

Preparation of Tri-Linker Intermediates:

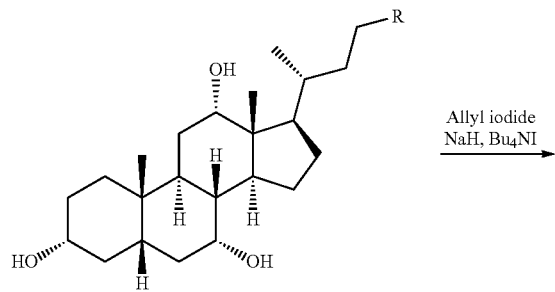

Allyl iodide
NaH, Bu₄NI
→

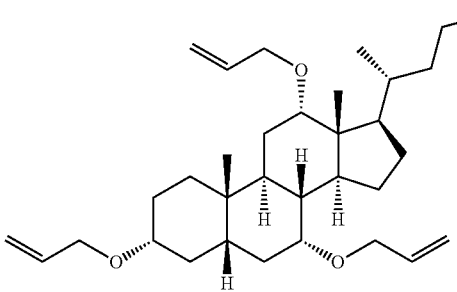

Compound 9:
NMR (500 MHz, CDCl3) δ=5.93-5.89 (m, 3H), 5.29-5.12 (m, 6H), 4.08-4.05 (m, 2H), 4.00 (d, J=5.5 Hz, 2H), 3.54 (brs, 1H), 3.32 (brs, 1H), 3.18-3.10 (m, 1H), 2.30-1.03 (m, 23H), 0.90 (d, J=7.0 Hz, 3H), 0.89 (s, 3H), 0.86 (t, J=7.0 Hz, 3H), 0.66 (s, 3H). $^{13}$C NMR (125 MHz, CDCl3): δ=136.5, 136.3, 116.6, 115.8, 81.2, 79.5, 75.3, 69.8, 69.7, 69.1, 47.0, 46.7, 43.0, 42.5, 40.2, 38.7, 36.0, 35.8, 35.4, 29.3, 28.4, 28.1, 27.9, 23.7, 23.4, 19.7, 18.2, 15.0, 13.0 ppm.

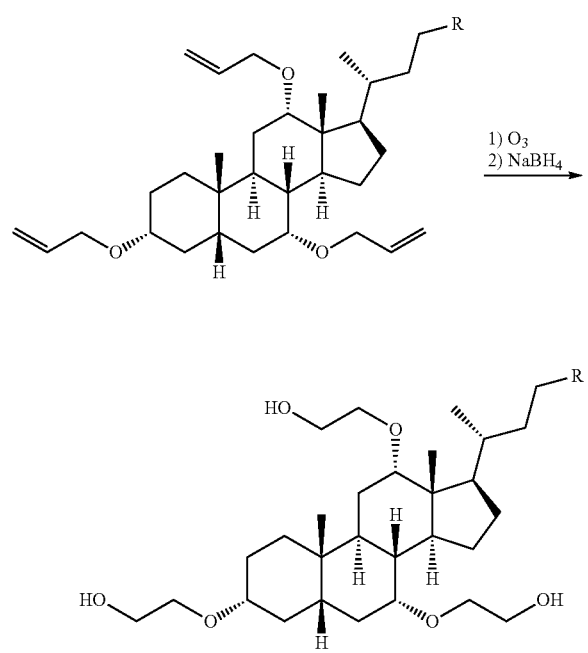

1) O₃
2) NaBH₄
→

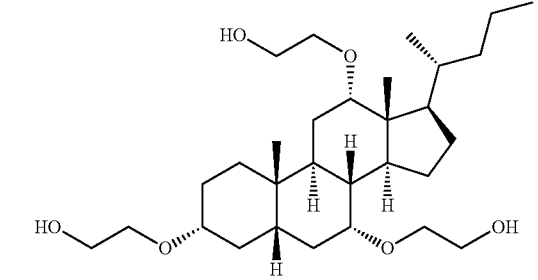

The procedure is analogous to the preparation of compound 3, using a starting material of trihydroxycholane prepared through Kolbe electrolysis as described above.

Compound 10:
$^1$H NMR (500 MHz, CDCl₃) δ=3.75-3.67 (m, 8H), 3.64-3.62 (m, 1H), 3.57-3.53 (m, 3H), 3.36-3.32 (m, 2H), 3.21 (brs, 1H), 3.14 (brs, 1H), 3.05 (brs, 3H), 2.25-1.05 (m, 23H), 0.90 (d, J=6.5 Hz, 3H), 0.89 (s, 3H), 0.85 (t, J=7.0 Hz, 3H), 0.67 (s, 3H) ppm; ESI-MS: calcd for C₃₀H₅₄O₆Na⁺ [M+Na⁺]: 533.4. found 533.5.

Preparation of Compound C1:

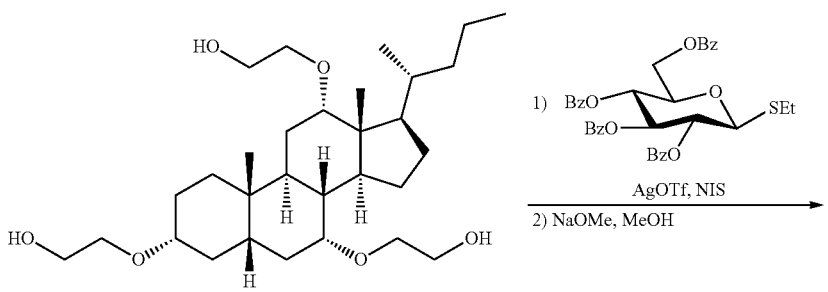

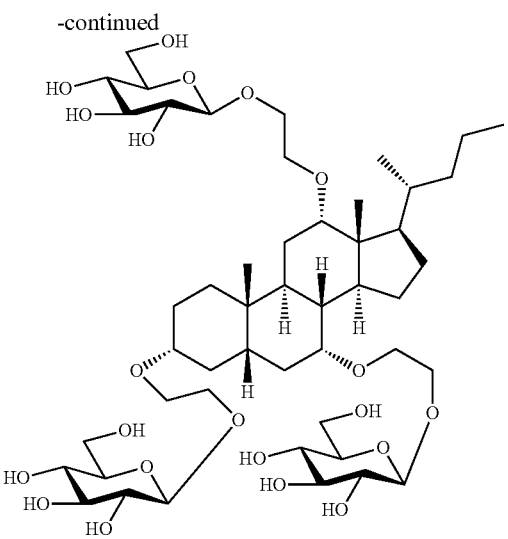
C1
C1:
The preparatory procedure is analogous to the preparation of A3, using compound 10 as starting material (66% after 2 steps).
Data for C1: $^1$H NMR (400 MHz, MeOD) δ=4.38 (d, J=8.0 Hz, 1H), 4.34 (d, J=7.6 Hz, 1H), 4.31 (d, J=7.6 Hz, 1H), 4.10-3.97 (m, 3H), 3.89-3.84 (m, 3H), 3.80-3.67 (m, 12H), 3.54 (s, 1H), 3.44-3.19 (m, 23H), 2.30-1.04 (m, 24H), 0.94 (d, J=6.4 Hz, 3H), 0.92 (s, 3H), 0.87 (t, J=6.8 Hz, 3H), 0.69 (s, 3H) ppm. $^{13}$C NMR (100 MHz, MeOD): δ=103.3, 103.2, 103.0, 81.8, 80.5, 76.9, 76.8, 76.7, 76.6, 76.3, 74.0, 73.9, 73.8, 70.5, 70.4, 68.9, 68.7, 68.5, 67.9, 67.7, 67.1, 61.7, 61.6, 46.7, 43.0, 42.1, 39.7, 38.4, 35.7, 35.1, 35.0, 34.7, 28.5, 28.3, 23.0, 22.2, 19.1, 17.4, 13.8, 11.8 ppm. HRESI: $C_{48}H_{84}O_{21}Na^+$: 1019.5397. found: 1019.5400, IR=3361, 2929, 2868, 2490, 2072, 1458, 1368, 1163, 1076, 983, 618 cm$^{-1}$.
Preparation of Compound C2:
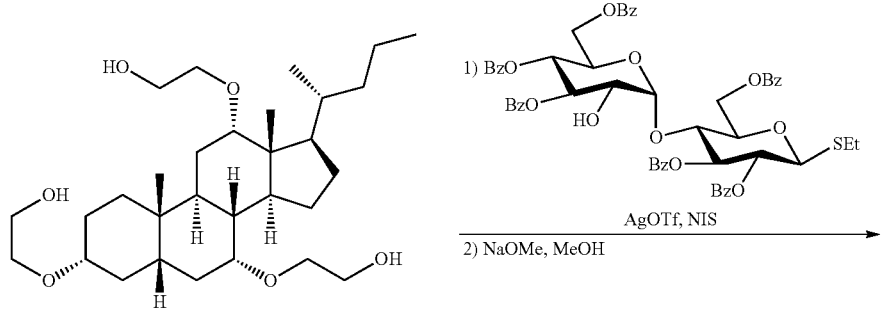
10

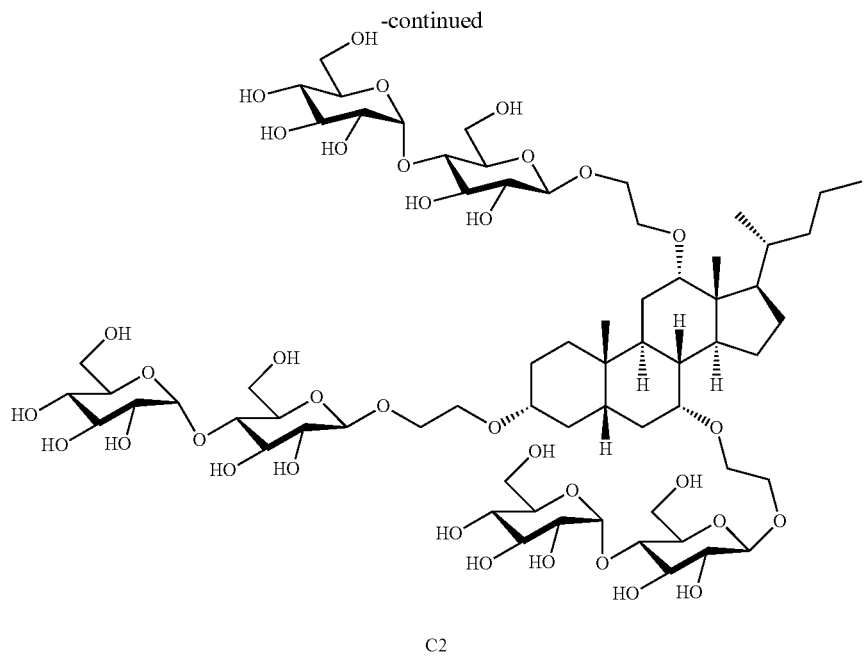

C2

C2:
The procedure is analogous to the preparation of A2, using compound 10 as starting material (74% after 2 steps).

Data for C2: $^1$H NMR (400 MHz, MeOD) δ=5.19-5.16 (m, 3H), 4.39 (d, J=8.0 Hz, 1H), 4.38 (d, J=8.0 Hz, 1H), 4.34 (d, J=8.0 Hz, 1H), 4.04-3.52 (m, 40H), 3.46-3.17 (m, 23H), 2.33-1.00 (m, 24H), 0.94 (d, J=6.4 Hz, 3H), 0.91 (s, 3H), 0.87 (t, J=6.8 Hz, 3H), 0.69 (s, 3H) ppm. $^{13}$C NMR (100 MHz, MeOD): δ=104.4, 102.9, 102.9, 83.5, 82.9, 82.9, 81.7, 81.3, 81.2, 81.2, 77.9, 77.8, 76.6, 75.1, 74.8, 74.2, 71.6, 69.9, 68.3, 62.8, 48.4, 47.9, 47.5, 43.3, 40.9, 39.6, 36.9, 36.7, 35.9, 23.4, 20.4, 18.7, 15.0, 13.0 ppm. HR-ESI: $C_{66}H_{114}NaO_{36}^+$: 1505.6982. found: 1505.6971, IR=3351, 2930, 2496, 2238, 2072, 1368, 1119, 1035, 983 cm$^{-1}$.

Preparation of Compound C3:

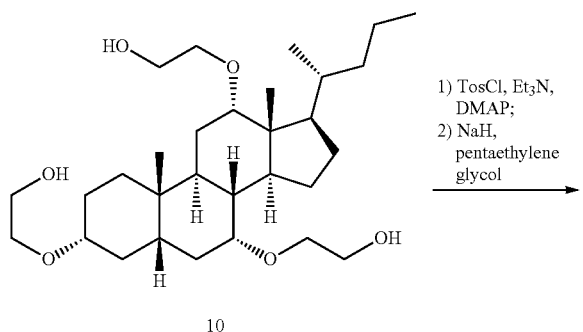

1) TosCl, Et$_3$N, DMAP;
2) NaH, pentaethylene glycol

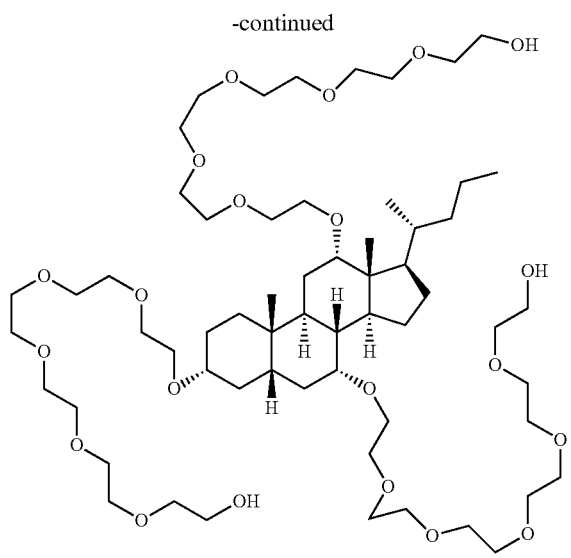

C3

C3:
The procedure is analogous to the preparation of A5, using compound 10 as starting material (88% over 2 steps).

Data for compound C3: $^1$H NMR (400 MHz, MeOD) δ=3.74-3.62 (m, 66H), 3.58-3.55 (m, 8H), 3.47-3.35 (m, 3H), 3.22-3.14 (m, 1H), 2.24-1.02 (m, 24H), 0.97 (d, J=6.4 Hz, 3H), 0.94 (s, 3H), 0.89 (t, J=6.8 Hz, 3H), 0.71 (s, 3H) ppm. $^{13}$C NMR (100 MHz, MeOD): δ=82.6, 81.3, 77.7, 73.7, 72.0, 71.9, 71.8, 71.8, 71.7, 71.6, 71.5, 69.3, 69.2, 68.3, 62.3, 47.9, 47.4, 44.0, 43.3, 41.0, 39.7, 37.0, 36.4, 36.0, 29.8, 29.3, 28.9, 28.6, 24.2, 23.4, 20.4, 18.6, 15.0, 13.0 ppm. HRESI: $C_{60}H_{115}O_{21}^+$: 1171.7925. found: 1171.7935, IR=2864, 2074, 1458, 1348, 1095, 982, 942 cm$^{-1}$.

Preparation of Compound C4:
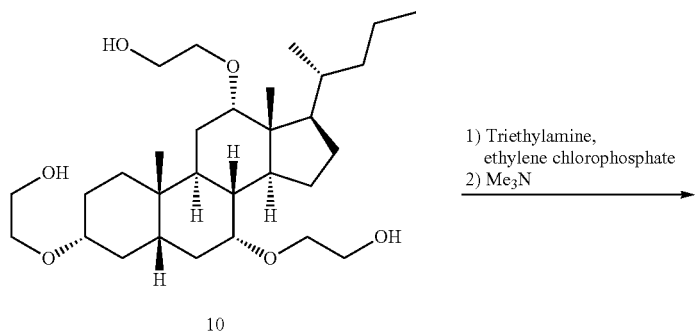
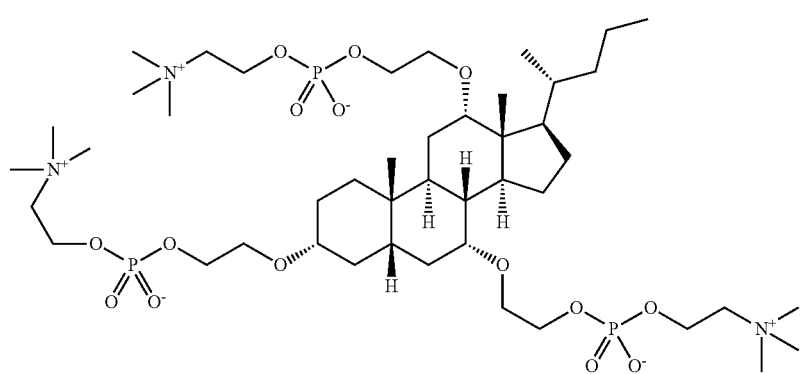
C4:
The procedure is analogous to the preparation of A7, using compound 10 as starting material (45% over 2 steps).
Data for compound C4: $^1$H NMR (400 MHz, MeOD) δ=4.28 (s, 6H), 4.00-3.92 (m, 6H), 3.74-3.63 (m, 10H), 3.56 (s, 1H), 3.48-3.35 (m, 4H), 3.24 (s, 18H), 3.22 (s, 9H), 2.12-1.00 (m, 24H), 0.94 (d, J=6.4 Hz, 3H), 0.90 (s, 3H), 0.85 (t, J=6.8 Hz, 3H), 0.69 (s, 3H) ppm. $^{13}$C NMR (100 MHz, MeOD): δ=83.5, 81.6, 77.8, 69.5, 69.4, 69.1, 69.0, 67.5, 37.4, 66.9, 66.6, 66.5, 66.4, 60.7, 60.6, 54.9, 54.8, 47.7, 44.4, 43.2, 40.9, 39.7, 37.0, 35.9, 29.7, 23.4, 20.7, 18.7, 14.9, 13.1 ppm. HRESI: $C_{45}H_{91}N_3O_{15}P_3^+$: 1006.5657. found: 1006.5636, IR=3160, 2866, 1645, 1490, 1233, 1087, 1061, 957, 794 cm$^{-1}$.
Preparation Compounds 19:
-continued
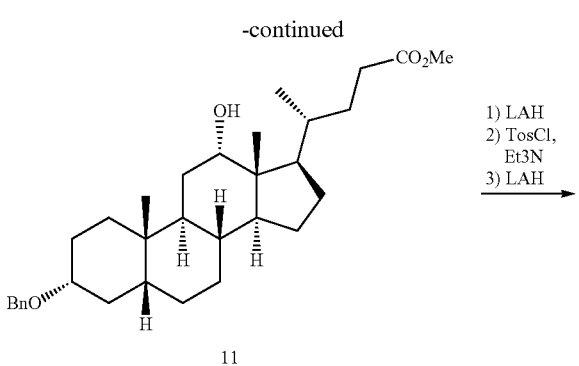
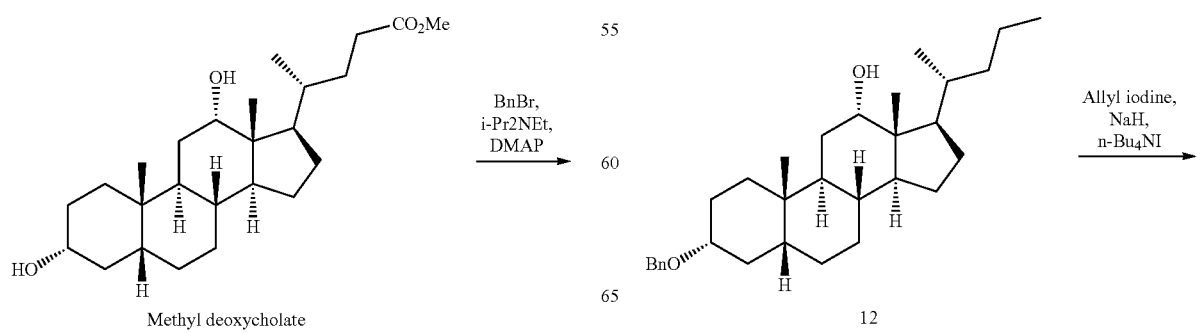

-continued
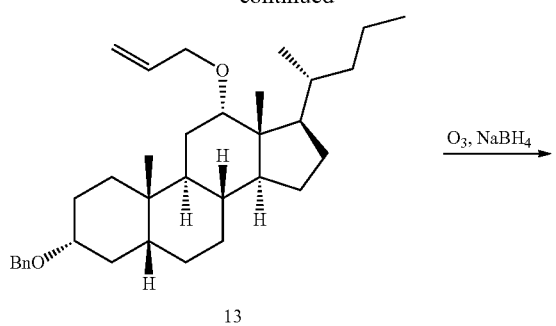
Preparation Compounds D1:
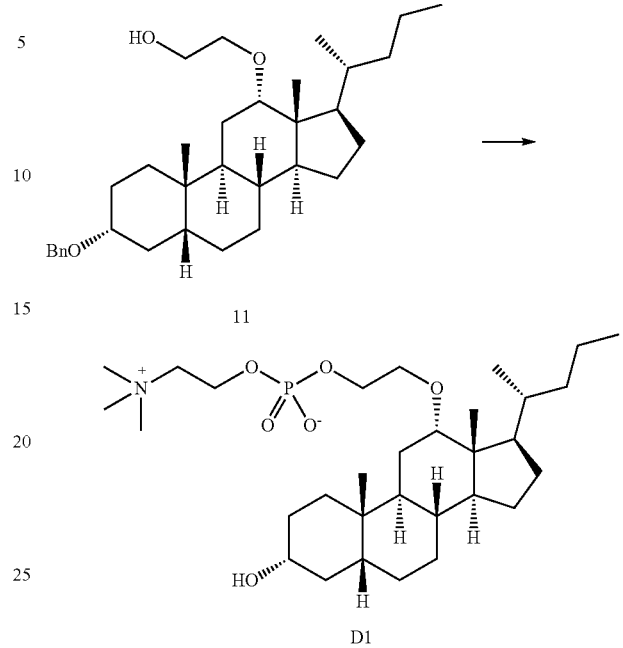
The procedure is analogous to the preparation of compound 8, using methyl deoxycholate as starting material.
The procedure is analogous to the preparation of B5, using compound 14 as starting material.
Preparation Compounds E1:
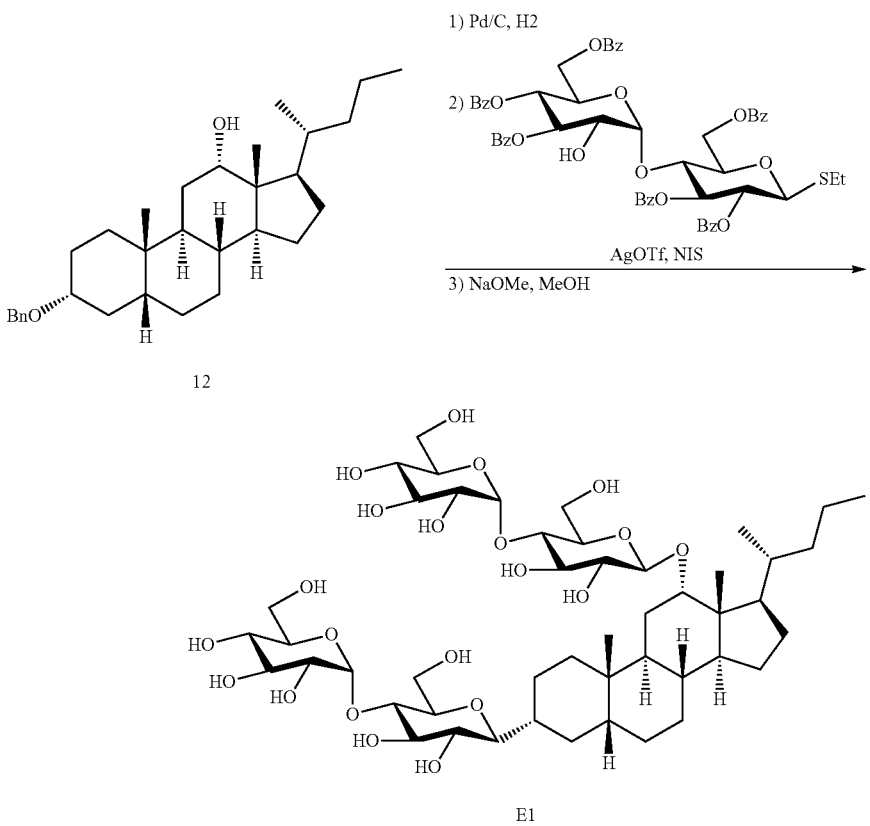

Compound E1:

To a solution of compound 12 (200 mg, 0.44 mmol) in methanol (30 mL) was added 10% Pd on activated carbon (20 mg). The reaction was stirred under hydrogen for 24 hours. The mixture was filtered and the solvent was evaporated under vacuum to give dihydroxy deoxycholane (170 mg) which was used directly without further purification.

The procedure was similar to the preparation of A2 with above residue as starting material.

Data for E1: $^1$H NMR (400 MHz, CD$_3$OD) δ=5.19 (d, J=4.0 Hz, 2H), 4.42 (d, J=7.2 Hz, 1H), 4.37 (d, J=7.2 Hz, 1H) 4.00-3.15 (m, 25H), 2.20-1.02 (m, 22H), 1.03 (d, J=5.2 Hz, 3H), 0.94 (s, 3H), 0.87 (t, J=5.2 Hz, 3H), 0.73 (s, 3H) ppm.

Example 2

Stabilization of Integral Membrane Proteins

Compound A1 has a relatively low CMC of 0.01% (0.1 mM) in water at 25° C., quite close to that of dodecyl-β-D-maltoside (DDM, 0.0087%, 0.17 mM), which is one of the currently most useful detergents for membrane protein purification and crystallization. The CMC values of sodium cholate (0.41-0.60%, 9.5-14 mM), CHAPS (0.49%, 8 mM) and CHAPSO (0.50%, 8 mM) are 80-140 times greater than compound A1, which shows that the newly designed facial amphiphile has a much greater tendency to self-assemble. The hydrodynamic radius of the micelle formed by compound A1 measured at a concentration of 0.03% is 3.0-3.1 nm, which is slightly smaller than that of DDM (3.3-3.4 nm at the same concentration).

Compound A1 was first evaluated for solubilization and stabilization of MsbA from *S. typhimurium* (ST-MsbA), an ATP-binding cassette transporter protein comprised of two transmembrane domains and two nucleotide-binding domains. The purified protein in the candidate detergent was assayed for activity by a standard linked enzyme ATPase assay to probe the protein stability. Undecyl-β-D-maltoside (β-UDM), the detergent used for ST-MsbA purification and crystallization, conferring the highest protein activity in previous experiments, was used as a positive control.

Figure 2:
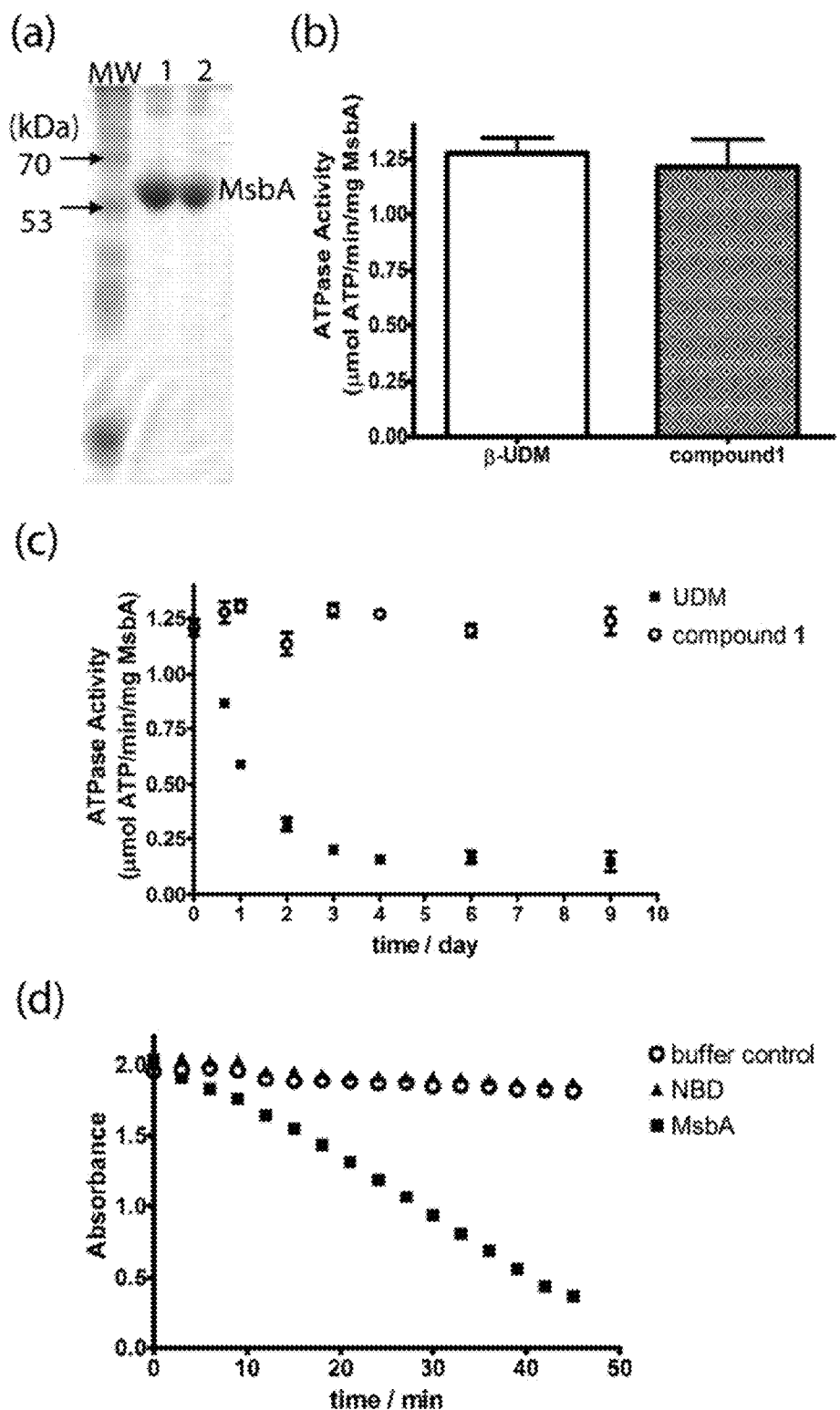
FIG. 2 illustrates: (a) SDS-PAGE showing purity of MsbA extracted from membranes and purified with β-UDM (lane 1) (positive control) and compound 1 (lane 2); (b) ATPase activity of freshly purified MsbA in β-UDM and compound 1; (c) MsbA stability in the presence of β-UDM (solid square) and compound 1 (open circle) at RT, examined by the ATPase activity as a function of time. The data is the average of 3 measurements with standard error bars shown.

Other steroid-based detergents including sodium cholate, CHAPS, and CHAPSO, were found to be very poor (<15%) agents for solubilizing MsbA. In contrast, compound A1 gave equivalently complete solubilization and initial ATPase activity (1.21±0.06 μmol ATP·min$^{-1}$·mg$^{-1}$) as β-UDM (1.19±0.03 μmol ATP·min$^{-1}$·mg$^{-1}$) under the same conditions (see FIGS. 2a and 2b). When the enzymatic activity of the purified protein in β-UDM and compound A1 was followed for more than a week at RT (about 23° C.), the protein solution in the presence of A1 remained clear and equally active, whereas in the presence of β-UDM, MsbA collapsed to form visible aggregates and lost more than 70% of its ATPase activity in 2 days (FIG. 2c). While it is the soluble nucleotide binding domain (NBD) of MsbA that is responsible for ATP hydrolysis, this domain alone showed no ATPase activity (FIG. 2d), suggesting the presence of a correctly folded transmembrane domain is necessary for full catalytic function.

Figure 3:
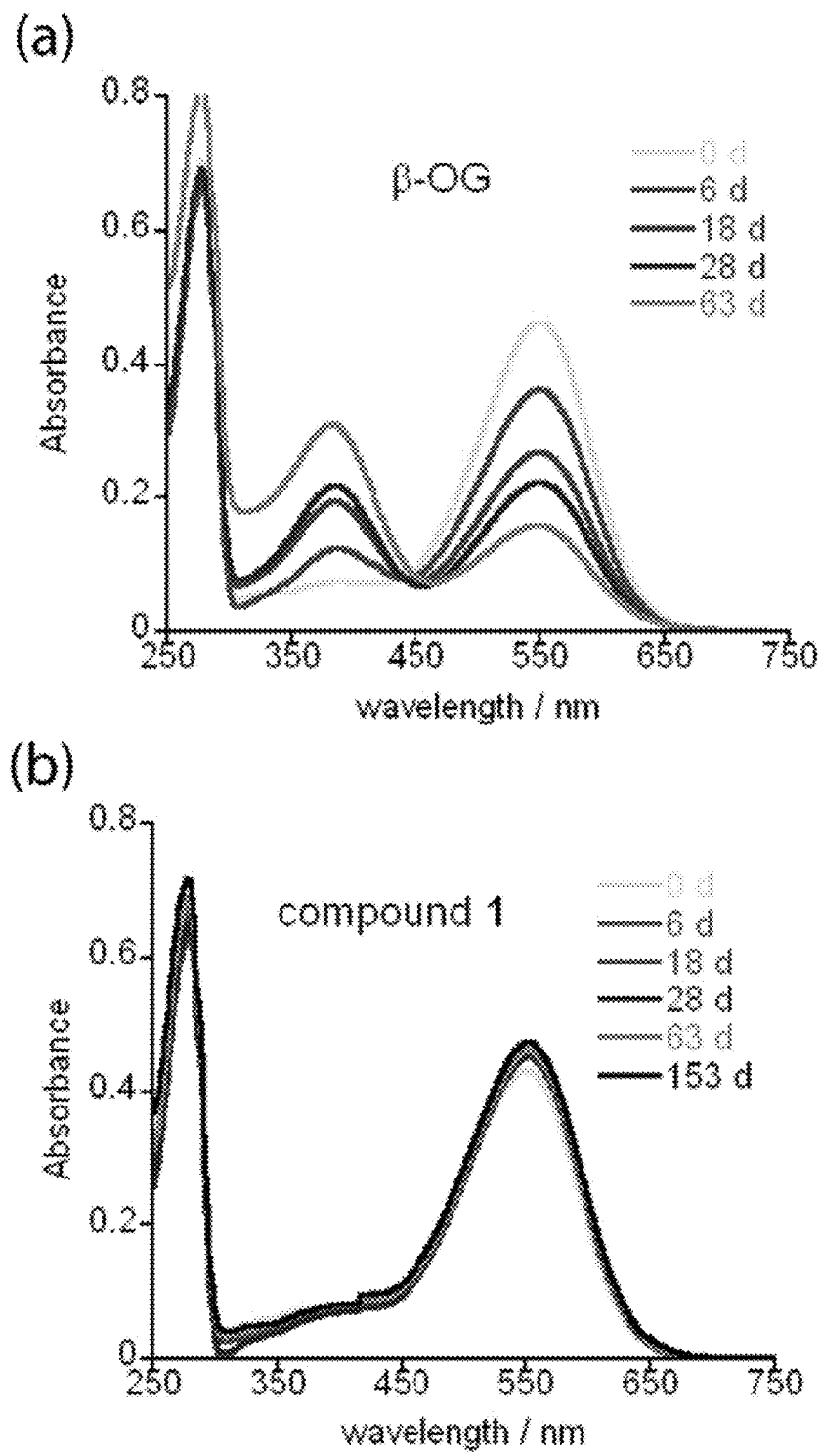
FIG. 3 illustrates an absorbance spectrum of bacteriorhodopsin (BR) (pH 5.6, RT) in (a) octyl-β-D-glucoside (β-OG), and (b) compound 1.

Compound A1 was also investigated for the stabilization of bacteriorhodopsin (BR) isolated from the purple membrane of *Halobacterium halobium*. BR has a characteristic adsorption at visible wavelength ($\lambda_{max}$: ~550 nm in detergents) due to the bound retinal ligand in the interior of the transmembrane region, serving as an excellent system for the testing of designed amphiphiles. BR has been stored in the presence of compound A1 for more than 5 months (pH 5.6, RT) and remained completely stable. In contrast, BR gradually denatured in the presence of octyl-β-D-glucoside (OG), which has been previously used for BR crystallization and consequently, as a standard for stability comparisons of the protein (FIG. 3).

Classical detergents form large protein-detergent complexes, with micellar or prolate monolayer ring arrangements. The structurally unique facial amphiphiles can have binding properties distinct from the classical detergents in segregating the hydrophobic transmembrane surfaces of IMPs. Compound A1 ($C_{48}H_{82}O_{22}$) has about twice the number of sugar and hydrophobic carbons as DDM ($C_{24}H_{46}O_{11}$), and its cholate backbone is presented in a flat and a much larger hydrophobic surface similar to that of cholesterol. The calculated length of the hydrophobic part of A1 is 13.4 Å (by Chem3D, MM2 energy minimization), and therefore two molecules of A1 can bridge most of the 30 Å hydrophobic dimension of a lipid bilayer.

Using a colorimetric assay, it was determined that the maltoside detergent content in MsbA fractions eluted from well-equilibrated chromatography. The concentration of detergents associated with MsbA was obtained by subtracting the baseline detergent concentration from the measured overall detergent concentration. The detergent binding ratio was determined to be 219±13 and 37±4 (mol/mol MsbA) for β-UDM and compound A1, respectively. The much smaller number of facial amphiphiles A1 bound to MsbA indicates that a smaller protein-detergent complex is formed. The larger hydrophobic surface area of the facial amphiphile gives rise to a more efficient stabilizing interaction with the membrane-spanning region of the protein. Therefore, the decarboxylated cholic acid platform provides a versatile and easily accessible platform for generating a new family of detergents useful for the stabilization of IMPs. Many other polar groups besides glycosides can be attached to the α-hydroxyl groups of the cholate skeleton to provide facial amphiphiles with similar properties, and/or alternatively, other advantageous properties for uses described herein.

Critical Micelle Concentration (CMC) Measurement.

Figure 4:
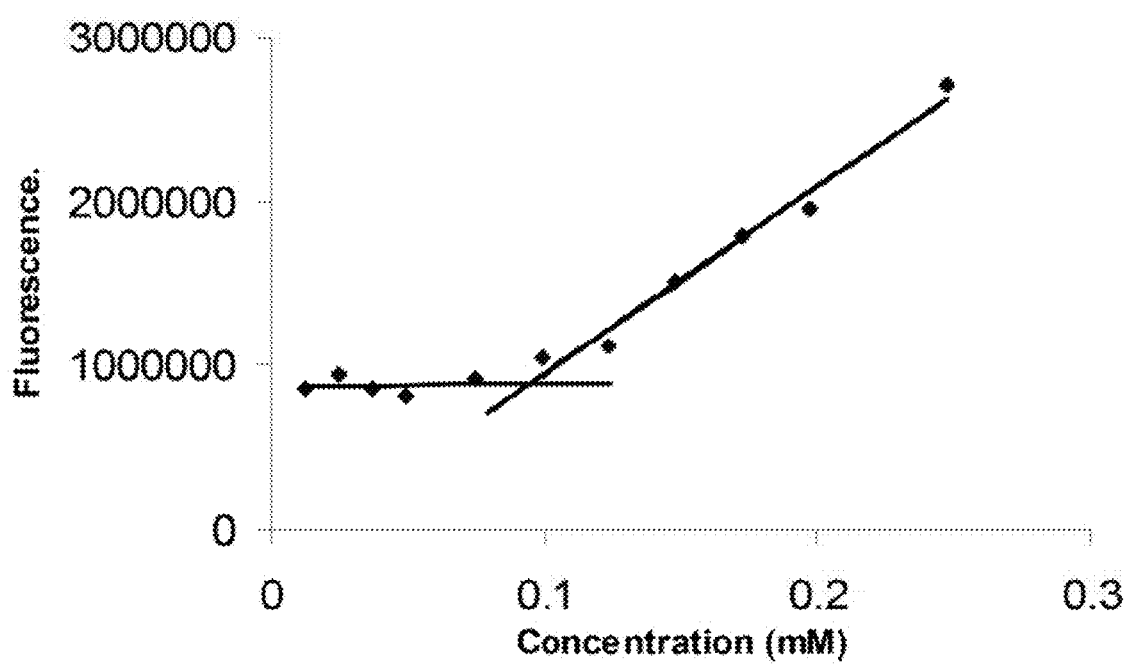
FIG. 4 illustrates CMC determination of compound 1 by 8-anilino-1-naphtalenesulfonic ammonium salt (ANS) binding ($\lambda_{ex}$=405 nm, $\lambda_{em}$=465 nm), according to an embodiment of the invention.

The CMC of compound A1 was determined by using a fluorescence dye binding technique with 8-anilino-1-naphtalenesulfonic ammonium salt (ANS) as the probe molecule. See De Vendittis et al., *Anal. Biochem.* 1981, 115, 278-86. The molecule ANS has a weak fluorescence in detergent concentrations below CMC, but becomes highly fluorescent when incorporated into the hydrophobic micellar environment. Solutions of ANS (10 μM) and A1 at various concentrations in water were prepared. The emission fluorescence intensities at 465 nm were recorded ($\lambda_{ex}$=405 nm) on a DXT880 multiplate spectrofluorimeter (Beckman Coulter). The CMC is defined as the breakpoint in the fluorescence (FIG. 4).

Measurement of Hydrodynamic Radius of Detergent Micelles.

The micelles formed by DDM and compound A1 (same concentration at 0.03%) were measured on DynaPro/Titan instrument (Wyatt Technology Corporation) equipped with a plate reader and a laser operating at 658 nm.

MsbA Preparation.

MsbA was prepared from *S. typhimurium* as described previously (Reyes, C. L.; Chang, G. *Acta Crystallograph Sect. F Struct. Biol. Cryst. Commun.* 2005, 61, 655-8). The membranes were solubilized in 20 mM detergents (β-UDM and compound A1, respectively) buffered with 20 mM Tris, 20 mM NaCl (pH 8.0). The supernatant after centrifugation at 200,000 g for 45 min was subjected to Ni-affinity column for purification. The protein extraction and purity was evaluated by SDS-PAGE. MsbA was further purified by anion-exchange chromatography and desalting column for the stability evaluation which was followed by ATPase activity measurement. MsbA (12-20 mg/mL) was stored in a pH 7.5 solution buffered with 20 mM Tris and 20 mM NaCl in the presence of 0.03% β-UDM and 0.02% compound A1, respectively.

Preparation of Isolated Nucleotide Binding Domain.

The NBD only construct (residues 330-582) was cloned into pET19b expression vector (Novagen), which contains a 23-residue fusion leader containing an N-terminal decahistidine tag to aid in purification, over-expressed in *E. coli* host BL21 (DE3) (Novagen) in 100 liter batch fermentors at 37° C. using 2 mM IPTG (Anatrace, Maumie, Ohio) as the inducer, and extracted by sonication at 4° C. Extracted NBD was purified with 10% glycerol by nickel-chelation followed by ion-exchange and gel-filtration chromatography to increase protein enrichment and purity. The protein was finally exchanged into 20 mM Tris (pH 7.5), 100 mM NaCl.

ATPase Activity.

ATPase activity was measured using an ATP-regenerating system described by Vogel and Steinhart (*Biochemistry* 1976, 15, 208-16), and modified by Urbatsch et al. (*J. Biol. Chem.* 1995, 270, 19383-90). Briefly, 1-2 µg of detergent solubilized MsbA was added to 100 µL of Linked Enzyme (LE) buffer at 37° C. containing 10 mM ATP, 12 mM $MgCl_2$, 6 mM phosphoenolpyruvate (PEP), 1 mM NADH, 10 units of lactate dehydrogenase (LDH), 10 units of pyruvate kinase (PK), and 50 mM Tris-HCl (pH 7.5). ATP hydrolysis was measured as the decrease in absorbance of NADH at 340 nm using a DXT880 multiplate spectrofluorimeter (Beckman-Coulter). ATPase activity was calculated using the following equation: $\Delta OD*\epsilon/([protein]*time)$, where $\Delta OD$ is the change in optical density and c is the extinction coefficient.

Detergent Binding Measurement Using Glycosidic Colorimetric Assay.

Figure 5:
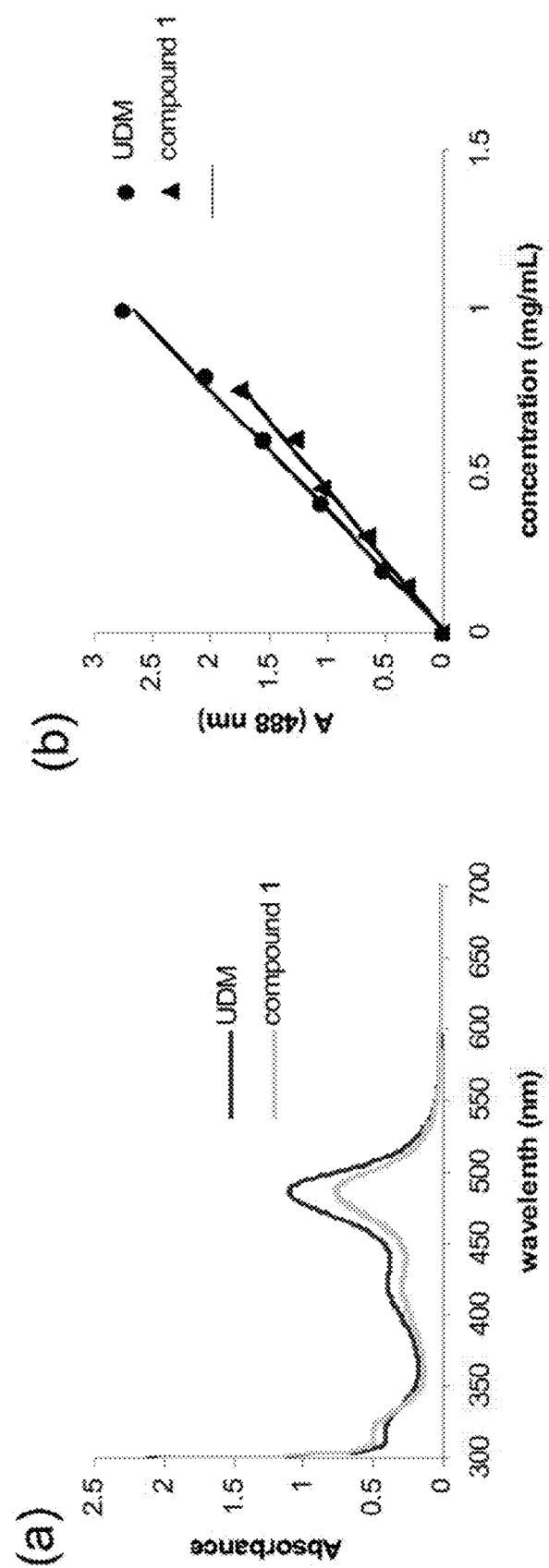
FIG. 5 illustrates (a) spectra obtained from detergents reacted with phenol and sulphuric acid; (b) standard curves from UDM (undecyl-β-D-maltoside) and compound 1 in a colorimetric assay, according to an embodiment of the invention.

The detergent binding was determined according to a literature procedure (A. Urbani, T. Warne, *Anal. Biochem.* 2005, 336, 117-124). Briefly, 50 uL detergent-containing samples were mixed with 200 uL of 5% phenol solution and 600 uL of concentrated sulfuric acid. The reaction produced orange-yellow color which had a maximal adsorption at 488 nm. A calibration curve of absorbance at 488 nm as a function of detergent concentration was first established for β-UDM and compound A1, respectively (FIG. 5). The above purified MsbA fractions in β-UDM and compound A1 from sephadex gel column without involving concentration step were used to determine the total detergent concentration. The molar ratio of detergent binding was calculated using the following equation: $[(C_{det, total} - C_{det, baseline})/[MW]_{det}]/[C_{MsbA}/128,000]$.

Preparation of Bacteriorhodopsin (BR).

BR was isolated from purple membrane of *Halobacterium halobium* (strain S9) and purified in 1.2% β-octyl-glycoside (OG) as reported in literature (Landau, E. M.; Rosenbusch, J. P. *Proc. Natl. Acad. Sci. USA* 1996, 93, 14532-5). The concentrated BR stock (13.5 mg/mL) in 1.2% OG (25 mM potassium phosphate, pH 5.6) was diluted to 0.02% compound A1 in the same buffer. After several dilution-concentration cycles, the final OG concentration was <1% of its CMC (0.53%). BR samples (0.2 mg/mL) were incubated in compound A1 (0.02%) and OG (1.2%) at RT in the dark. The UV-Vis absorption spectra of BR samples were recorded on a DXT880 multiplate spectrofluorimeter (Beckman Coulter).

Example 3

Characterization of Class a and Class B Amphiphiles

Critical micelle concentration (CMC) was measured using an ANS fluorescence assay, as described for the CMC measurement for compound A1 in Example 2 above. See also De Vendittis et al., *Anal. Biochem.* 1981, 115, 278-86.

CMC values of selected compounds of Example 3: A1, 0.01%; A2, 0.01%; B1, 0.02%; B2, 0.013%. Micelle size (hydrodynamic radius measured at 0.03% concentration in dl water on DynaPro/Titan instrument (Wyatt Technology Corporation)): A1, 3.0 nm; A2, 2.7 nm; B1, 2.2 nm.

The new facial amphiphiles had relatively small CMC values (0.01%-0.02%), in contrast to the high CMCs of known cholate-based detergents (0.4-0.6% for sodium cholate, CHAPS and CHAPSO), indicating a higher tendency for these molecules to self-assemble. Retaining the 3α-OH group was found to enhance water solubility and induce the formation of small micelles.

Biological Data

The facial detergents can be used for the preparation of membrane protein samples for functional and structural studies (x-ray crystallography, electron microscopy, NMR and small angle scattering). These molecules can be used as single amphiphiles or mixed with other commercial detergents or lipids for the above applications.

It was demonstrated that the facial amphiphiles can substantially stabilize the integral membrane proteins tested thus far, including bacteriorhodopsin, MsbA, cytochrome c oxidase ba3, and Connexin 26. A bacteriorhodopsin sample prepared in the facial amphiphile A1 had no observable UV-vis spectral change over the course of almost one year. In the case of *S. typhimurium* MsbA, the facial amphiphiles A1 and B1 afforded similar or higher ATPase activity than β-UDM, which gave the highest ATPase activity among all 24 commercial detergents tested. β-UDM was also the optimal known detergent used for crystallization of this protein.

Several facial amphiphiles were tested in the crystallization of cytochrome P450 CYP24A1, which is a 53 kD inner mitochondrial monotopic membrane protein. Extensive hybrid screening using protein purified in CHAPS with new facial amphiphiles as additives has yielded improved resolution and crystallization behavior. Data at 2.0 Å resolution were obtained for a monoclinic crystal form using CHAPS with B1. The use of CHAPS alone yielded CYP24A1 crystals of ~7 Å resolution.

The facial amphiphiles were evaluated in the crystallization of cytochrome c oxidase ba3 by detergent exchange from β-DDM. Several new crystal forms were obtained depending on which detergent was used, albeit in less than optimal diffraction quality (>6 Å). Thin layer analysis showed that the detergent exchange was incomplete and about 20% DDM was still present. However, it is remarkable that the protein is not crystallizable in pure DDM whereas numerous crystals were seen in various conditions when mixed with the facial amphiphiles. Crystals of human connexin 26 have also been obtained using the purely facial amphiphiles described herein.

The facial amphiphiles self-assemble to smaller micelles and form smaller protein-detergent complexes (PDCs) than the conventional detergents. Because of these unique properties, facial amphiphiles can be used for SAX (small-angle x-ray scattering) studies of integral membrane proteins. A major challenge for applying SAXS to membrane protein structural analysis is the need to separate the scattering signal of the PDC from that of the empty micelles. With conventional head-to-tail detergents, it is difficult to achieve this goal because of the presence of the large detergent micelles and the characteristic second peak in the scattering intensity. Remarkably, the facial amphiphiles described herein allow one to separate the scattering signal of the PDC from that of the empty micelles. Favorable results have been obtained with MsbA prepared in the presence of B1.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A compound of Formula I:

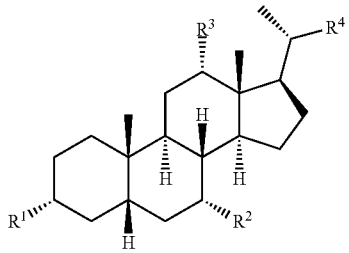

(I)

wherein
R$^1$ is H or OH, R$^2$ and R$^3$ are each independently —X—R;
wherein X is a direct bond and R is a monosaccharide or a disaccharide, and
R$^4$ is (C$_1$-C$_{20}$)alkyl, wherein the alkyl is straight, branched, cyclic, or a combination thereof; or a salt thereof.

2. The compound of claim 1 wherein the disaccharide is maltose.

3. The compound of claim 1 wherein the compound is:

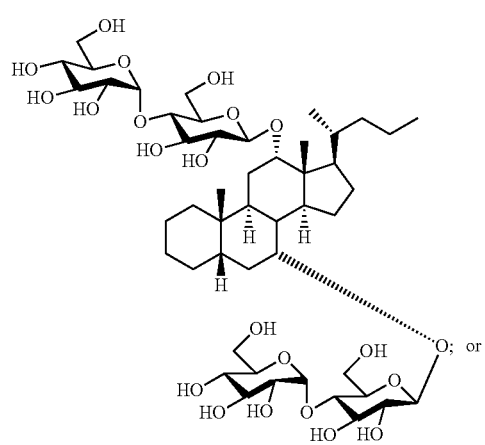

A1

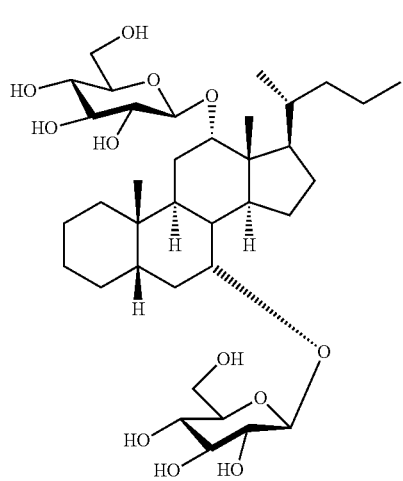

A3 or a salt thereof.

4. A compound of Formula I:

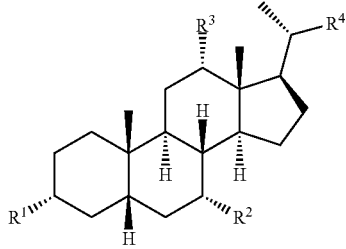

(I)

wherein
R$^1$ is H or OH, R and R are each independently —X—R;
wherein X is a direct bond and R is a group of formula —(OCH$_2$CH$_2$)$_n$—OH where n is 1 to about 20; or —X—R is —OCH$_2$CH$_2$O-monosaccharide, —OCH$_2$CH$_2$O-disaccharide, —OCH$_2$CH$_2$O—P(O)(OH)O—CH$_2$CH$_2$OH, —OCH$_2$CH$_2$O—P(O)(OH)O—CH$_2$CH$_2$—N$^+$(Me)$_3$, or —OCH$_2$CH$_2$O—P(O)(OH)O—CH$_2$CH$_2$—N$^+$(Me)$_2$O—;
and
R$^4$ is (C$_1$-C$_{20}$)alkyl, wherein the alkyl is straight, branched, cyclic, or a combination thereof;
or a salt thereof.

5. The compound of claim 4 wherein the compound is:

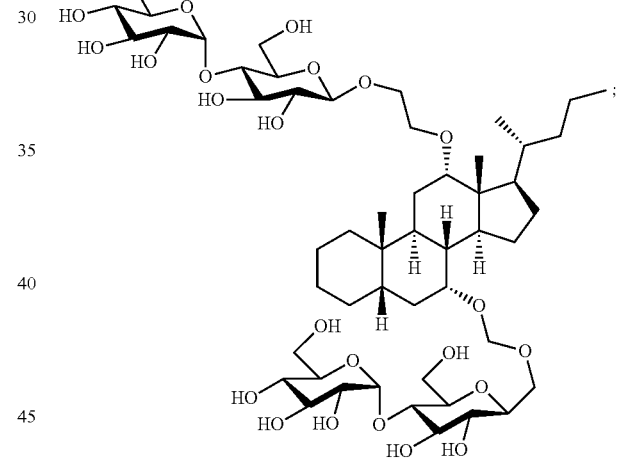

A2

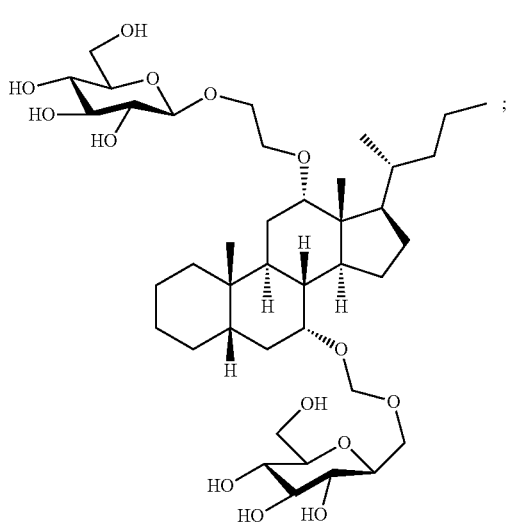

A4

A5
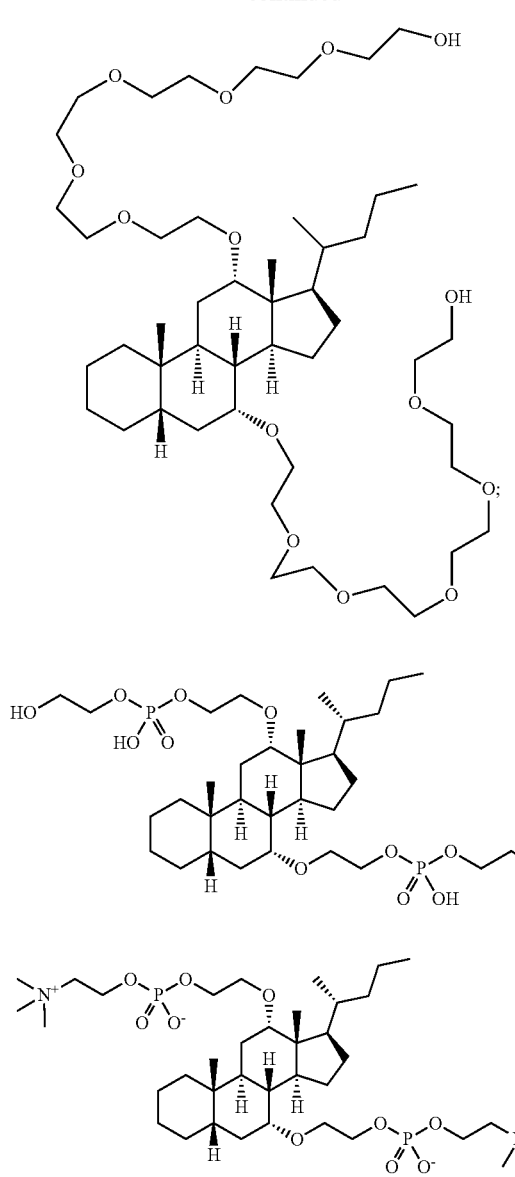
A6
A7
B1
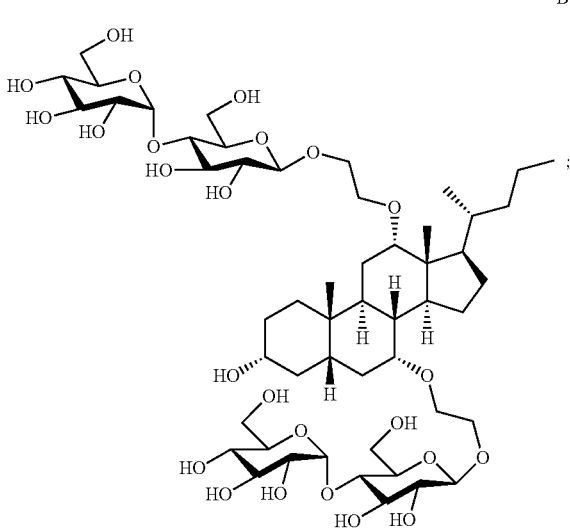
B2
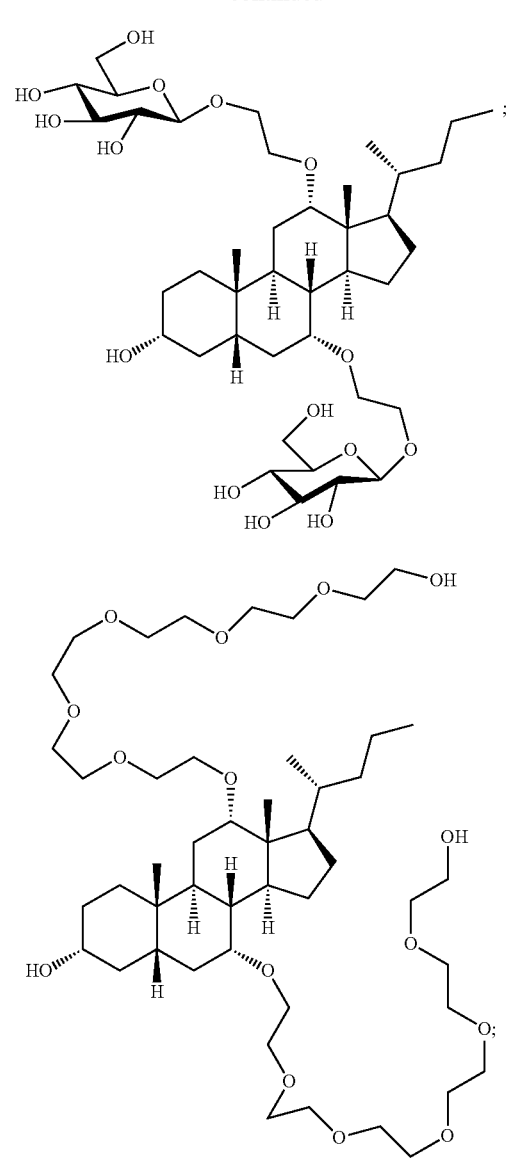
B3
B4
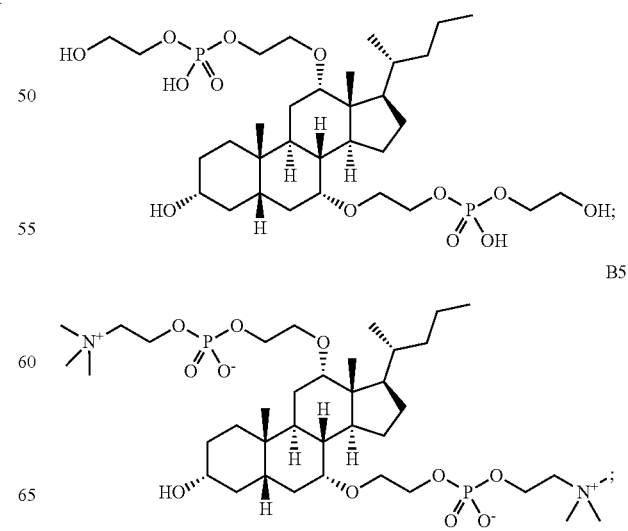
B5

77
-continued
B7
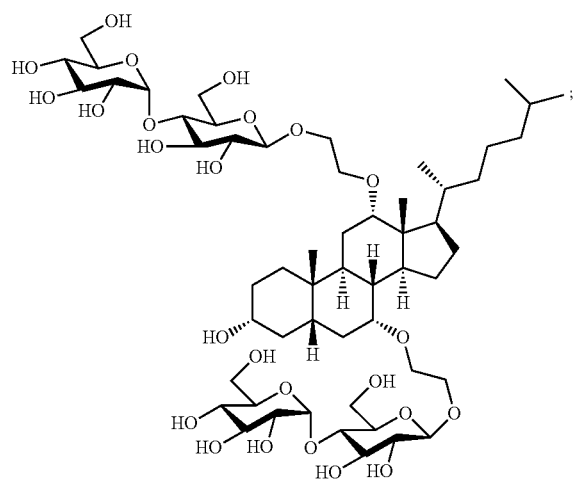
B8
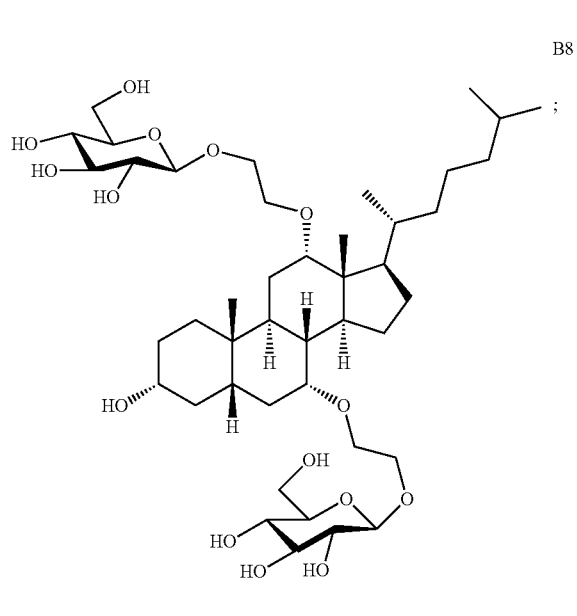
B9
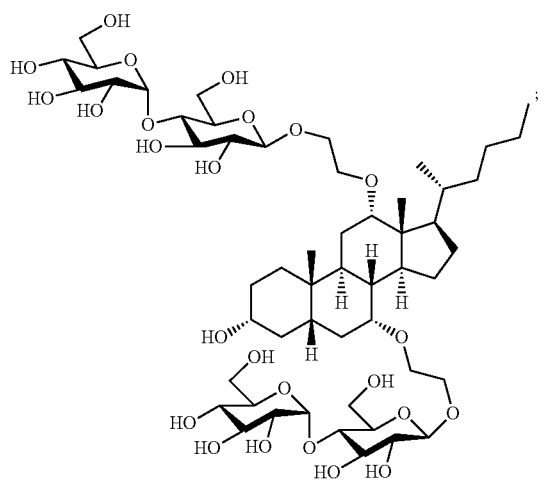
78
-continued
B10
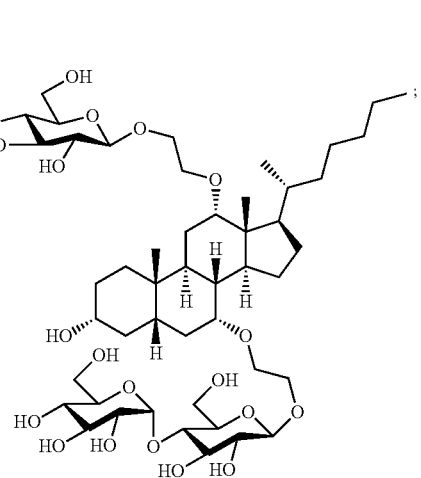
B11
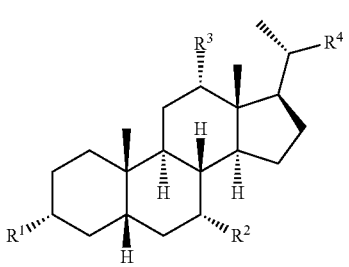
or
B12
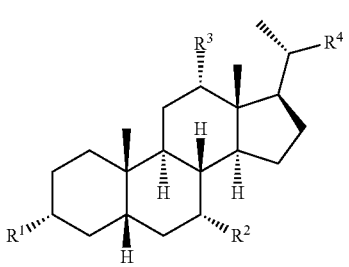
or a salt thereof.
6. A compound of Formula I:
(I)
wherein
$R^1$, $R^2$, and $R^3$ are each independently —X—R;
wherein X is a direct bond and R is a polar group selected from a group consisting of a monosaccharide, a disaccharide, and a group of formula —(OCH$_2$CH$_2$)$_n$—OH where n is 1 to about 20; or —X—R is —OCH$_2$CH$_2$O- monosaccharide, —OCH$_2$CH$_2$O-disaccharide, —OCH$_2$CH$_2$O—P(O)(OH)O—CH$_2$CH$_2$OH, —OCH$_2$CH$_2$O—P(O)(OH)O—CH$_2$CH$_2$—N$^+$(Me)$_3$, or —OCH$_2$CH$_2$O—P(O)(OH)O—CH$_2$CH$_2$—N$^+$(Me)$_2$O$^-$;
and
R$^4$ is (C$_1$-C$_{20}$)alkyl, wherein the alkyl is straight, branched, cyclic, or a combination thereof;
or a salt thereof.
7. The compound of claim 6 wherein the compound is
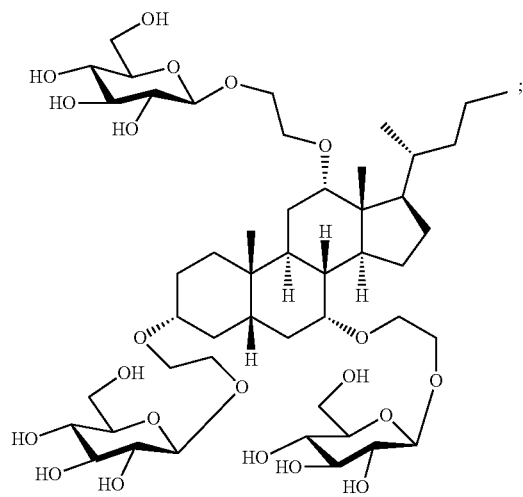
C1
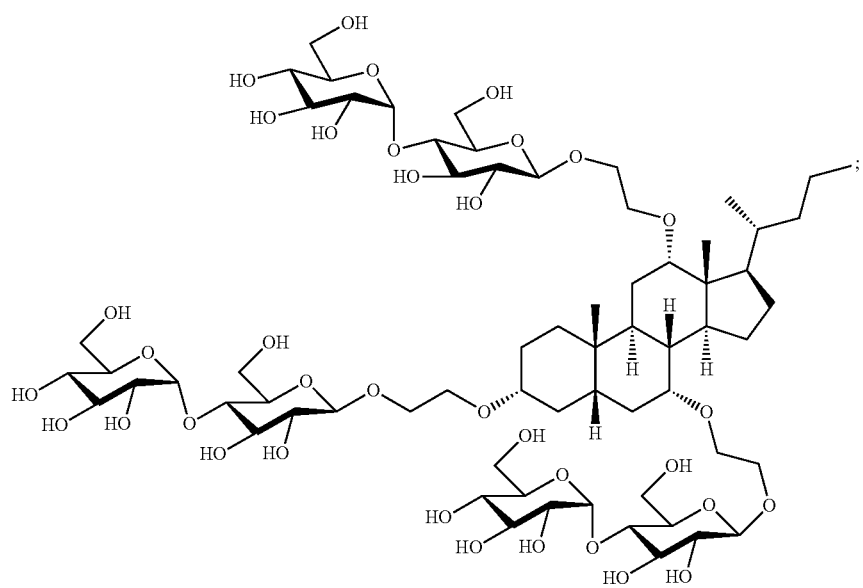
C2

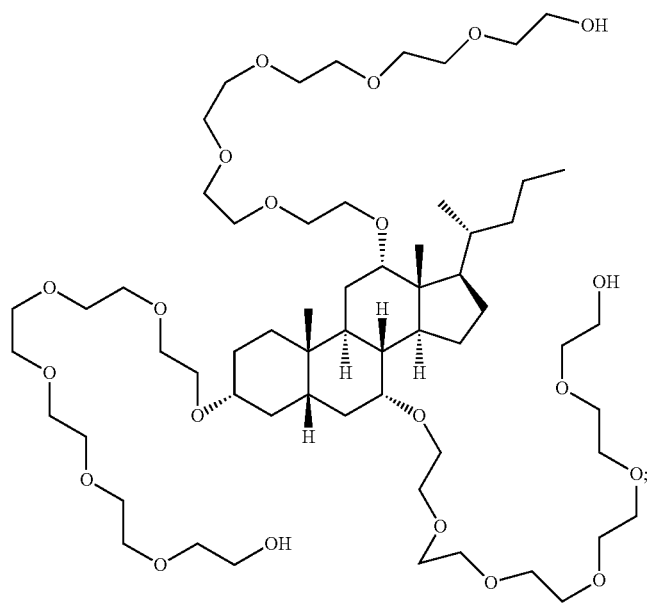
C3
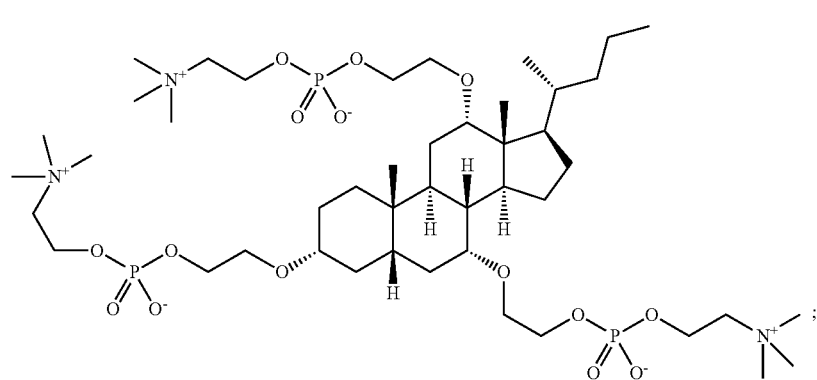
C4
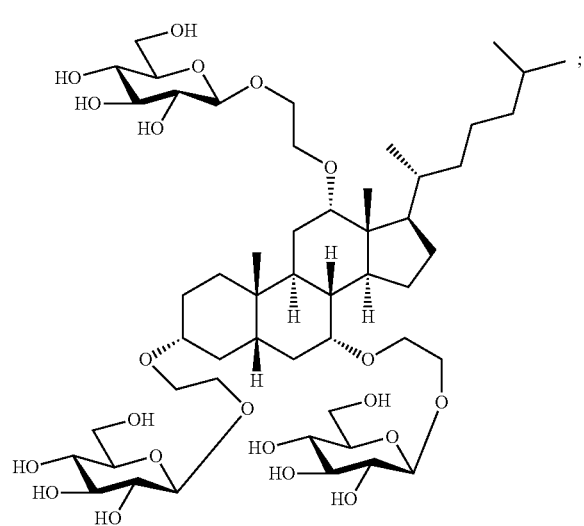
C5

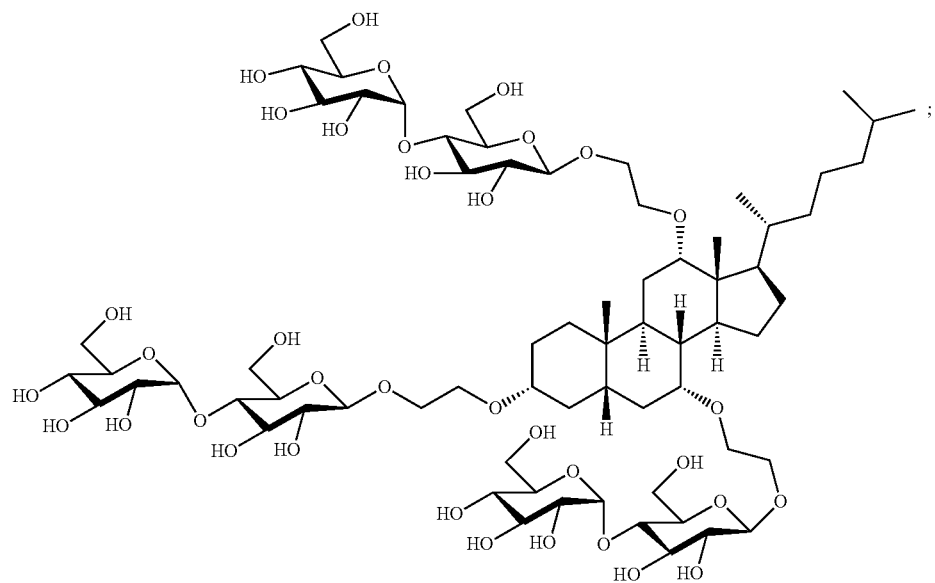
C6
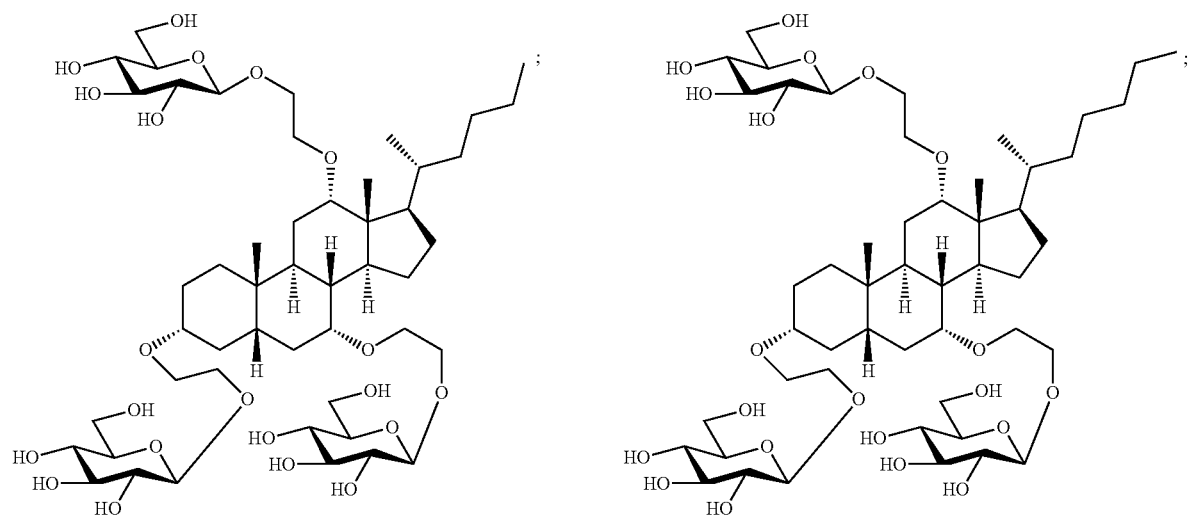
C8
C9

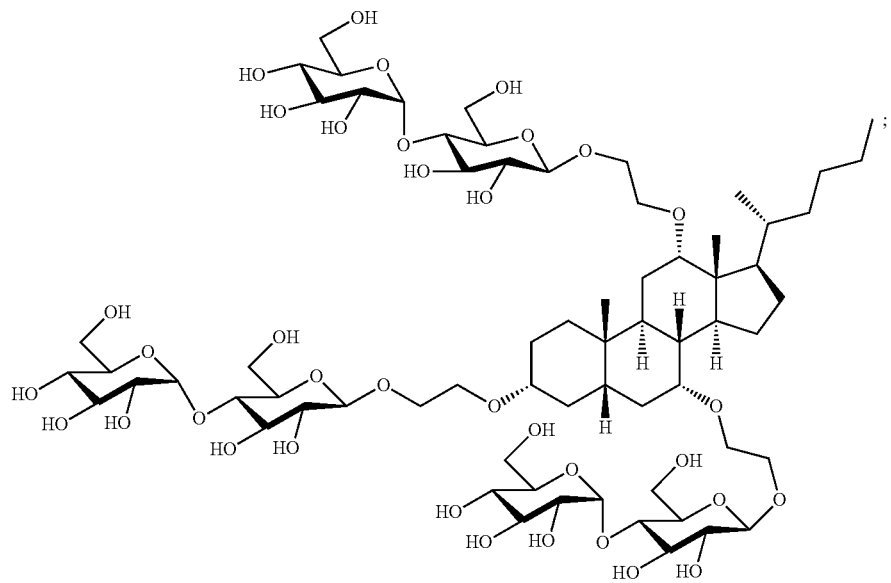
C10
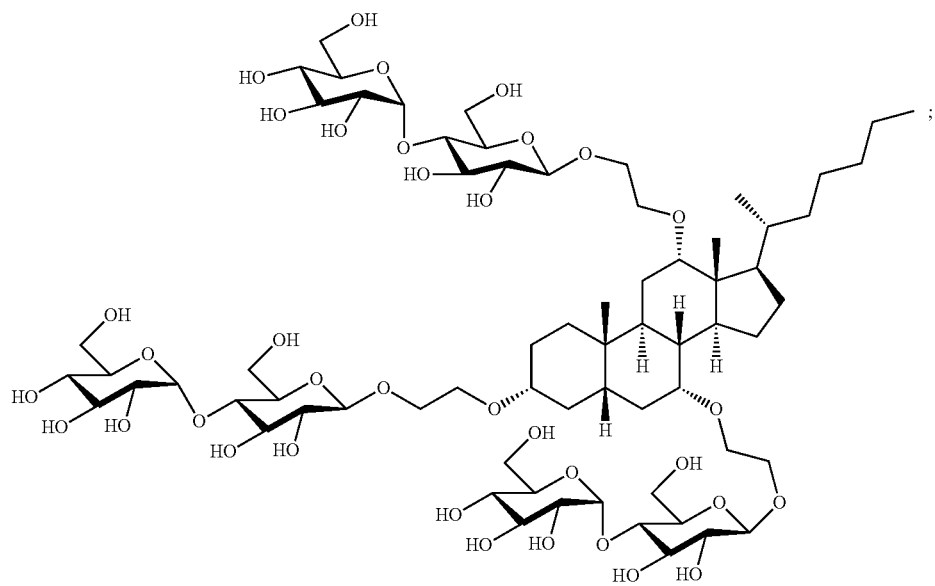
C11
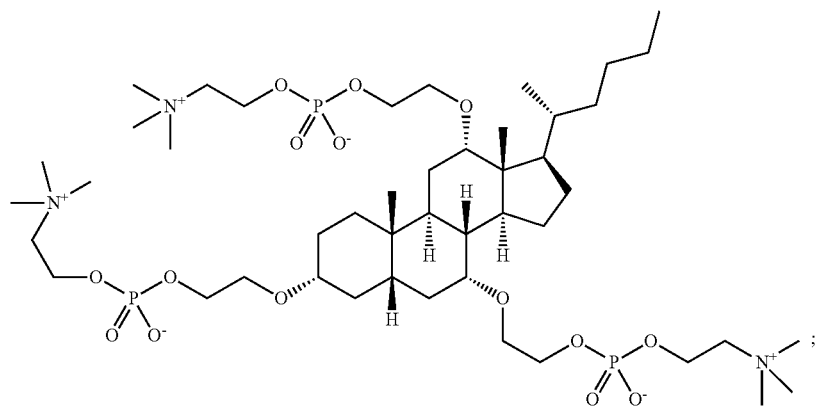
C12

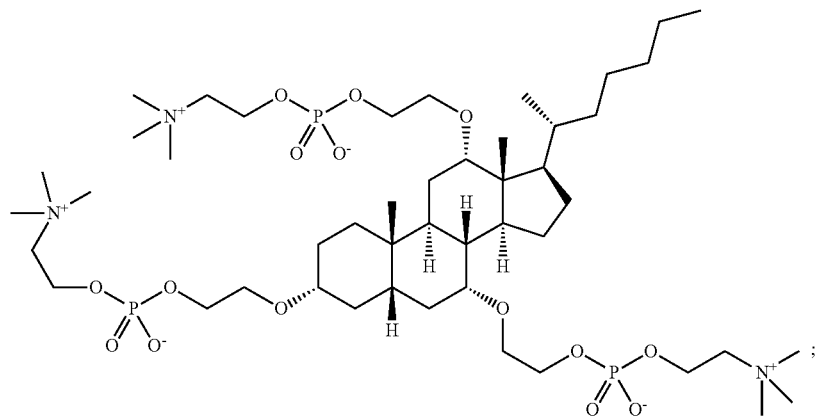
or a salt thereof.
* * * * *

UNITED STATES PATENT AND TRADEMARK OFFICE
CERTIFICATE OF CORRECTION

PATENT NO. : 9,085,602 B1
APPLICATION NO. : 12/536423
DATED : July 21, 2015
INVENTOR(S) : Zhang et al.

It is certified that error appears in the above-identified patent and that said Letters Patent is hereby corrected as shown below:

In the Specification

In column 2, line 40, delete "--$N^+(Me)_2(CH_2)$," and insert -- $-N^+(Me)_2(CH_2)_n$--, therefor In column 5, Scheme A, line 1, delete "

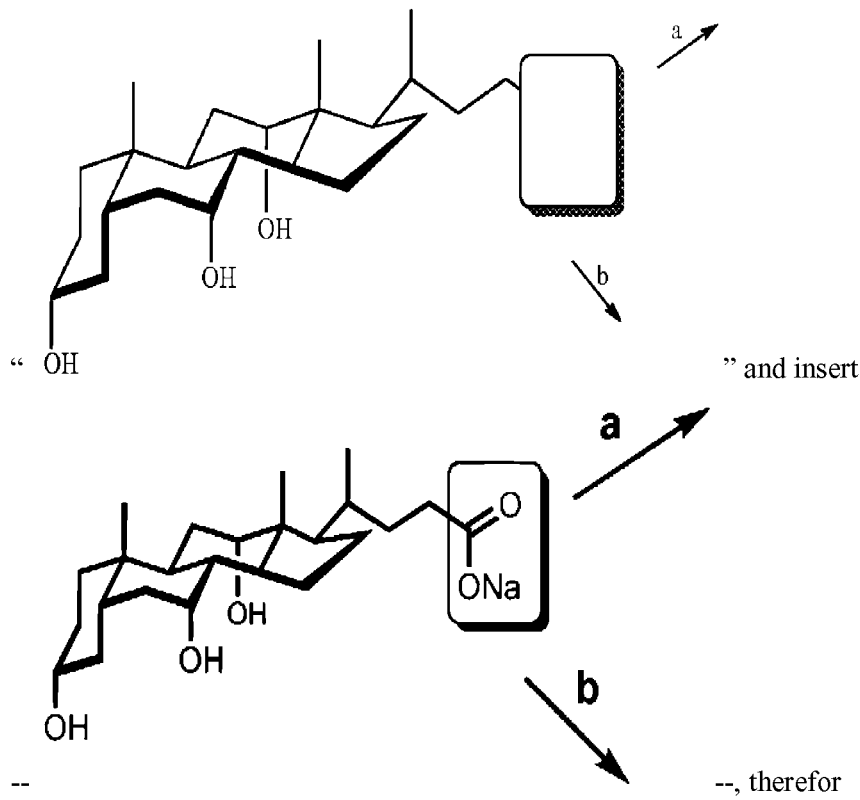

" and insert -- --, therefor

In column 6, line 54, delete "+5%," and insert --±5%,-- therefor

Signed and Sealed this
Twenty-ninth Day of December, 2015

Michelle K. Lee
*Director of the United States Patent and Trademark Office*

In column 14, after Equation A6, insert

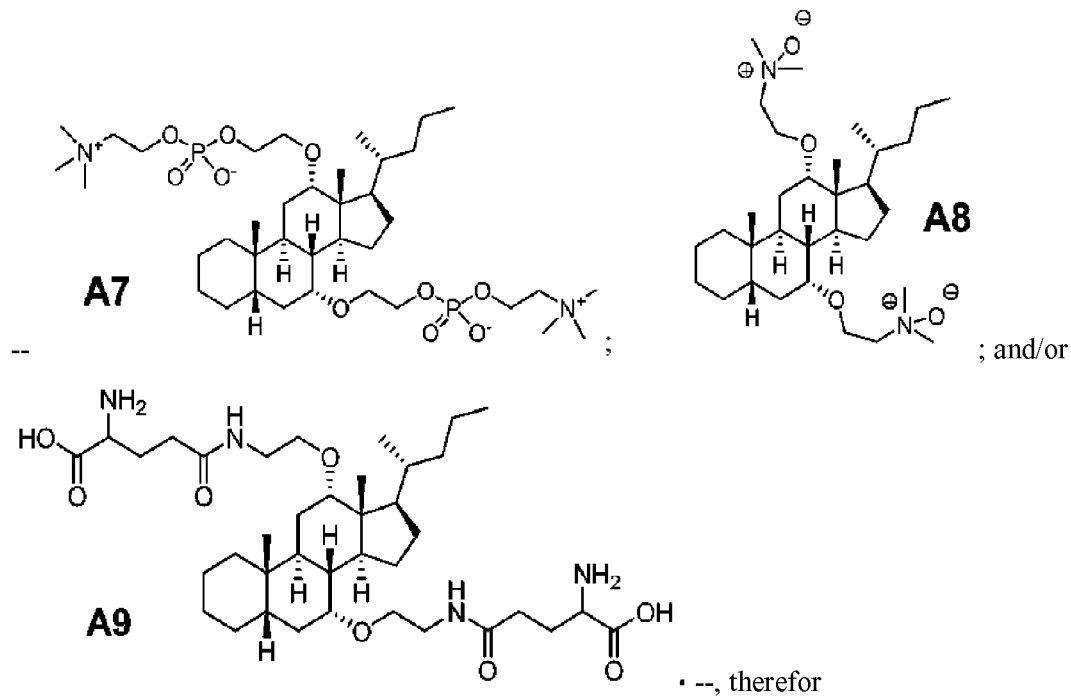

-- ; and/or  ·  --, therefor

In column 37, line 66, delete "IN" and insert --1N--, therefor
In column 38, line 65, delete "0° C." and insert --0 °C.--, therefor
In column 39, line 10-11, delete "0° C." and insert --0 °C.--, therefor
In column 39, line 15, delete "IN" and insert --1N--, therefor
In column 39, line 29, delete "385.3077." and insert --385.3077,--, therefor
In column 39, line 59, delete "(CD3OD)" and insert --(CD$_3$OD)--, therefor
In column 40, line 2, delete "1033.5190." and insert --1033.5190,--, therefor
In column 40, line 64, delete "0° C." and insert --0 °C.--, therefor
In column 41, line 53, delete "465." and insert --465,--, therefor
In column 42, line 6, delete "473." and insert --473,--, therefor
In column 44, line 17, delete "(CD3OD)" and insert --(CD$_3$OD)--, therefor
In column 45, line 14, delete "1121.5714." and insert --1121.5714,--, therefor
In column 46, line 3, delete "775.4838." and insert --775.4838,--, therefor
In column 46, line 52, delete "0° C." and insert --0 °C.--, therefor
In column 46, line 59, after "purification", insert --.--, therefor
In column 46, line 62, delete "0° C." and insert --0 °C.--, therefor
In column 47, line 5, after "steps)", insert --.--, therefor
In column 47, line 51, delete "0° C." and insert --0 °C.--, therefor
In column 47, line 60, delete "IN" and insert --1N--, therefor
In column 47, line 63, after "steps)", insert --.--, therefor In column 48, line 30, delete "0° C." and insert --0 °C.--, therefor In column 48, line 51, delete "803.4711." and insert --803.4711,--, therefor In column 49, line 27, delete "0° C." and insert --0 °C.--, therefor In column 49, line 48, delete "0° C." and insert --0 °C.--, therefor In column 49, line 66, delete "537.4626." and insert --537.4626,--, therefor In column 51, line 8, delete "IN" and insert --1N--, therefor In column 51, line 12, delete "NMR" and insert --$^1$H NMR--, therefor In column 51, line 12, delete "CDCl3)" and insert --CDCl$_3$)--, therefor In column 51, line 18, delete "0° C." and insert --0 °C.--, therefor In column 51, line 20, delete "IN" and insert --1N--, therefor In column 51, line 28, delete "0° C." and insert --0 °C.--, therefor In column 51, line 37, delete "0° C." and insert --0 °C.--, therefor In column 51, line 38, delete "IN" and insert --1N--, therefor In column 52, line 1, delete "NMR" and insert --$^1$H NMR--, therefor In column 52, line 1, delete "CDCl3)" and insert --CDCl$_3$)--, therefor In column 52, line 7, delete "0° C." and insert --0 °C.--, therefor In column 52, line 19, after "70%)", insert --.--, therefor In column 52, line 20, delete "NMR" and insert --$^1$H NMR--, therefor In column 52, line 20, delete "CDCl3)" and insert --CDCl$_3$)--, therefor In column 52, line 41, after "75%)", insert --.--, therefor In column 52, line 42, delete "NMR" and insert --$^1$H NMR--, therefor In column 52, line 42, delete "CDCl3)" and insert --CDCl$_3$)--, therefor In column 53, line 40, after "steps)", insert --.--, therefor In column 53, line 50, delete "1114.5771." and insert --1114.5771,--, therefor In column 55, line 1, delete "791.4787." and insert --791.4787,--, therefor In column 55, line 66, delete "929.6172." and insert --929.6172,--, therefor In column 57, line 11, delete "797.4841." and insert --797.4841,--, therefor In column 60, line 16, delete "NMR" and insert --$^1$H NMR--, therefor In column 60, line 16, delete "CDCl3)" and insert --CDCl$_3$)--, therefor In column 60, line 20, delete "CDCl3):" and insert --CDCl$_3$):--, therefor In column 60, line 46, delete "533.4." and insert --533.4,--, therefor In column 62, line 37, delete "1019.5397." and insert --1019.5397,--, therefor In column 63, line 47, delete "1505.6982." and insert --1505.6982,--, therefor In column 64, line 66, delete "1171.7925." and insert --1171.7925,--, therefor In column 65, line 49, delete "1006.5657." and insert --1006.5657,--, therefor

CERTIFICATE OF CORRECTION (continued)
U.S. Pat. No. 9,085,602 B1

In column 71, line 5, delete "4° C." and insert --4 °C.--, therefor

In column 71, line 23, delete "c" and insert --ε--, therefor

In column 71, line 61, delete "dl" and insert --dI--, therefor

In the Claims

In column 74, line 14, in Claim 4, delete "R" and insert --$R^2$--, therefor

In column 74, line 14, in Claim 4, delete "R" and insert --$R^3$--, therefor

In column 74, line 21, in Claim 4, delete "(Me)₂O--;" and insert --(Me)₂O⁻;--, therefor